United States Patent
Masuyama et al.

(10) Patent No.: US 9,671,692 B2
(45) Date of Patent: Jun. 6, 2017

(54) COMPOUND, RESIN AND PHOTORESIST COMPOSITION

(71) Applicant: SUMITOMO CHEMICAL COMPANY, LIMITED, Tokyo (JP)

(72) Inventors: Tatsuro Masuyama, Osaka (JP); Satoshi Yamaguchi, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/047,894

(22) Filed: Feb. 19, 2016

(65) Prior Publication Data

US 2016/0244400 A1 Aug. 25, 2016

(30) Foreign Application Priority Data

Feb. 24, 2015 (JP) .................. 2015-034214

(51) Int. Cl.
| | |
|---|---|
| G03F 7/004 | (2006.01) |
| G03F 7/039 | (2006.01) |
| G03F 7/30 | (2006.01) |
| G03F 7/32 | (2006.01) |
| G03F 7/38 | (2006.01) |
| C08F 220/68 | (2006.01) |
| C07C 69/757 | (2006.01) |
| C07C 69/653 | (2006.01) |
| C07C 69/753 | (2006.01) |

(52) U.S. Cl.
CPC .......... *G03F 7/0046* (2013.01); *C07C 69/653* (2013.01); *C07C 69/753* (2013.01); *C07C 69/757* (2013.01); *C08F 220/68* (2013.01); *G03F 7/0045* (2013.01); *G03F 7/0397* (2013.01); *G03F 7/30* (2013.01); *G03F 7/322* (2013.01); *G03F 7/325* (2013.01); *G03F 7/38* (2013.01); *C07C 2103/74* (2013.01)

(58) Field of Classification Search
None
See application file for complete search history.

(56) References Cited

U.S. PATENT DOCUMENTS

| | | | |
|---|---|---|---|
| 2012/0052443 A1 | 3/2012 | Masuyama et al. | |
| 2012/0064459 A1* | 3/2012 | Maeda ................... | C08F 20/26 430/285.1 |
| 2012/0183752 A1* | 7/2012 | Kodama ................. | B82Y 10/00 428/195.1 |
| 2012/0301828 A1* | 11/2012 | Tachibana ............. | G03F 7/0046 430/285.1 |
| 2016/0139508 A1* | 5/2016 | Masuyama ........... | G03F 7/0384 430/270.1 |
| 2016/0145186 A1* | 5/2016 | Masuyama ............. | G03F 7/038 430/270.1 |
| 2016/0147146 A1* | 5/2016 | Masuyama ............. | G03F 7/038 430/270.1 |

FOREIGN PATENT DOCUMENTS

JP 2009-271444 * 11/2009

OTHER PUBLICATIONS

JPO English abstract for JP 2009-271444 (2009).*
Machine-assisted English translation for JP 2009-271444 (2009) provided by JPO.*

* cited by examiner

*Primary Examiner* — Sin Lee
(74) *Attorney, Agent, or Firm* — Birch, Stewart, Kolasch & Birch, LLP

(57) ABSTRACT

A compound represented by formula (I):

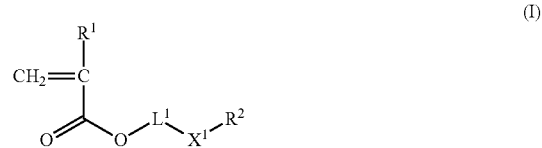

wherein $R^1$ represents a hydrogen atom, a halogen atom or a C1-C6 alkyl group where a hydrogen atom can be replaced by a halogen atom,
$L^1$ represents a C1-C8 fluorinated alkanediyl group,
$X^1$ represents *—CO—O—, *—O—CO—, *—O—CO—O— or *—O— where * represents a binding site to $L^1$, and
$R^2$ represents a C1-C18 hydrocarbon group in which a methylene group can be replaced by an oxygen atom, a carbonyl group or a sulfonyl group and in which a hydrogen atom can be replaced by a hydroxy group, or in which two hydrogen atoms can be each replaced by an oxygen atom forming one ketal structure together with a C1-C8 alkanediyl group bonded to the oxygen atom and a hydrogen atom in said ketal structure can be replaced by a fluorine atom.

2 Claims, No Drawings

COMPOUND, RESIN AND PHOTORESIST COMPOSITION

This nonprovisional application claims priority under 35 U.S.C. §119(a) on Patent Application No. 2015-034214 filed in JAPAN on Feb. 24, 2015 the entire contents of which are hereby incorporated by reference.

TECHNICAL FIELD

This disclosure relates to a compound, resin and a photoresist composition.

BACKGROUND ART

US2012/052443A1 mentions a resin obtained by polymerizing a compound of the following formula.

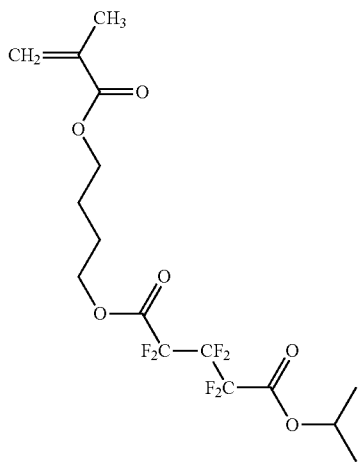 [SMILES: C=C(C)C(=O)OCCCCOC(=O)C(F)(F)C(F)(F)C(F)(F)C(=O)OC(C)C]

SUMMARY OF THE INVENTION

The invention of the disclosure relates to the followings:
<1> A compound represented by formula (I):

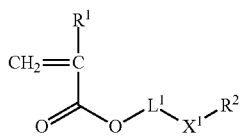
(I)

wherein $R^1$ represents a hydrogen atom, a halogen atom or a C1-C6 alkyl group where a hydrogen atom can be replaced by a halogen atom,
$L^1$ represents a C1-C8 fluorinated alkanediyl group,
$X^1$ represents *—CO—O—, *—O—CO—, *—O—CO—O— or *—O— where * represents a binding site to $L^1$, and
$R^2$ represents a C1-C18 hydrocarbon group in which a methylene group can be replaced by an oxygen atom, a carbonyl group or a sulfonyl group and in which a hydrogen atom can be replaced by a hydroxy group, or in which two hydrogen atoms can be each replaced by an oxygen atom forming one ketal structure together with a C1-C8 alkanediyl group bonded to the oxygen atom and a hydrogen atom in said ketal structure can be replaced by a fluorine atom.

<2> The compound according to <1>, wherein X' represent *—O—CO— where * represents a binding site to $L^1$.
<3> The compound according to <1> or <2>, wherein $L^1$ is represented by —$CH_2$—$(CF_2)_n$—$CH_2$— where "n" represents an integer of 1 to 6.
<4> The compound according to any one of <1> to <3>, wherein $R^2$ represents a C1-C12 aliphatic hydrocarbon group.
<5> A resin which comprises a structural unit derived from the compound according to any one of <1> to <4>.
<6> A photoresist composition which comprises
the resin according to <5>,
a resin which has an acid-labile group, and
an acid generator.
<7> A process for producing a photoresist pattern comprising the following steps (1) to (5):
  (1) a step of applying the photoresist composition according to <6> on a substrate,
  (2) a step of forming a composition film by drying the composition,
  (3) a step of exposing the composition film to radiation,
  (4) a step of baking the exposed composition film, and
  (5) a step of developing the baked composition film.

DESCRIPTION OF PREFERRED EMBODIMENTS

The invention of the disclosure will be illustrated.

In the specification, the term "(meth)acrylic monomer" means a monomer having a structure of "$CH_2$=CH—CO—" or "$CH_2$=C($CH_3$)—CO—", as well as "(meth)acrylate" and "(meth)acrylic acid" mean "an acrylate or methacrylate" and "an acrylic acid or methacrylic acid," respectively. Herein, chain structure groups include those having a linear structure and those having a branched structure.

The indefinite articles "a" and "an" are taken as the same meaning as "one or more".

The term "solid components" means components other than solvents in a photoresist composition.

<Compound>
The compound of the disclosure is represented by formula (I):

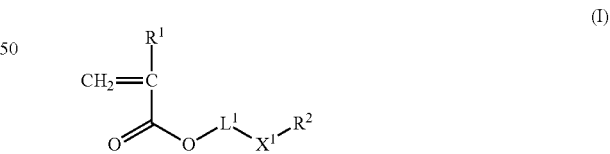
(I)

wherein $R^1$ represents a hydrogen atom, a halogen atom or a C1-C6 alkyl group where a hydrogen atom can be replaced by a halogen atom;
$L^1$ represents a C1-C8 fluorinated alkanediyl group;
$X^1$ represents *—CO—O—, *—O—CO—, *—O—CO—O— or *—O— where * represents a binding site to $L^1$, and
$R^2$ represents a C1-C18 hydrocarbon group in which a methylene group can be replaced by an oxygen atom, a carbonyl group or a sulfonyl group and in which a hydrogen atom can be replaced by a hydroxy group, or in which two hydrogen atoms can be each replaced by an oxygen atom forming one ketal structure together with a C1-C8 alkanediyl group bonded to the oxygen atom and a hydrogen atom in said ketal structure can be replaced by a fluorine atom.

For $R^1$, examples of the alkyl group include a methyl group, an ethyl group, a propyl group, an isopropyl group, an n-butyl group, a sec-butyl group, a tert-butyl group, an n-pentyl group, and an n-hexyl group, preferably a C1-C4 alkyl group, more preferably a methyl group and an ethyl group.

For $R^1$, examples of the halogen atom include a fluorine atom, a chlorine atom, a bromine atom and an iodine atom.

For $R^1$, examples of the alkyl group where a hydrogen atom has been replaced by a fluorine atom include a trifluoromethyl group, a perfluoroethyl group, a perfluoropropyl group, a perfluoroisopropyl group, a perfluorobutyl group, a perfluoro(sec-butyl) group, a perfluoro(tert-butyl) group, a perfluoropentyl group, a perfluoropropyl group, a perchloromethyl group, a perbromomethyl group, and a periodomethyl group.

$R^1$ is preferably a hydrogen atom or a methyl group.

Examples of the fluoroalkanediyl group for $L^1$ include linear fluoroalkanediyl groups such as fluoromethylene, fluoroethane-1,2-diyl, fluoropropane-1,3-diyl, fluorobutane-1,4-diyl, fluoropentane-1,5-diyl, fluorohexane-1,6-diyl, fluoroheptane-1,7-diyl, and fluorooctan-1,8-diyl groups; and branched fluoroalkanediyl groups such as what has a C1-C4 alkyl group as a branched group, including fluoroethane-1,1-diyl, fluoropropane-1,2-diyl, fluorobutane-1,3-diyl, 2-methylfluoropropane-1,3-diyl, 2-methylfluoropropane-1,2-diyl, 2-trifluoromethylfluoropropane-1,2-diyl, fluoropentane-1,4-diyl, 2-methylfluorobutane-1,4-diyl groups.

Among them, $L^1$ is preferably a fluorinated alkanediyl group other than perfluoroalkanediyl group, more preferably what has a methylene group bonded to the neighboring oxygen atom and $X^1$, and still more preferably a group represented by —$CH_2$—$(CF_2)_n$—$CH_2$— where "n" represents an integer of 1 to 6. The "n" represents preferably an integer of 1 to 4.

$X^1$ represents preferably *—O—CO—, *—O—CO—O— or *—O— where * represents a binding site to $L^1$, more preferably *—O—CO— where * represents a binding site to $L^1$.

For $R^2$, examples of the hydrocarbon group include aliphatic hydrocarbon groups such as alkyl groups and alicyclic hydrocarbon groups, aromatic hydrocarbon groups and any combinations of them.

Specific examples of the alkyl group include a methyl group, an ethyl group, a propyl group, an isopropyl group, a butyl group, a pentyl group, a hexyl group, a heptyl group, a 2-ethylhexyl group, an octyl group, a nonyl group, a decyl group, an undecyl group and a dodecyl group.

The alicyclic hydrocarbon group may be monocyclic or polycyclic. Examples of a monocyclic alicyclic hydrocarbon group include a C3-C12 cycloalkyl group such as a cyclopropyl group, a cyclobutyl group, a cyclopentyl group, a cyclohexyl group, a (methyl)cyclohexyl group, a (dimethyl)cyclohexyl group, a cycloheptyl group, a cyclooctyl group and cyclodecyl group.

Examples of a polycyclic alicyclic hydrocarbon group include a decahydronaphthyl group, an adamantyl group, a 2-alkyladamantane-2-yl group, a norbornyl group, a methylnorbornyl group, and an isobornyl group.

Examples of the aromatic hydrocarbon group include a phenyl group, and a naphthyl group.

Specific examples of the above-mentioned combination include aralkyl groups such as a benzyl group or a phenethyl group.

The hydrocarbon group represented by $R^2$ can have a ketal structure which optionally has a fluorine atom. The ketal structure is a structure which has a C1-C8 alkanediyl group bonded to two oxygen atoms and optionally fluorinated, specifically a structure represented by —O—$R^{2I}$—O— where $R^{2I}$ represents a C1-C8 alkanediyl group which optionally has a fluorine atom. In the ketal structure, two of the hydrogen atoms have been replaced by one of the oxygen atoms. The two hydrogen atoms may be bonded to the one and same carbon atom or two carbon atom different from each other respectively. The two hydrogen atoms are preferably bonded to the one and same carbon atom. The ketal structure forms preferably a 4- to 12-membered ring, and a 4- to 10-membered ring.

In $R^{2I}$, the carbon atoms bonded to an oxygen atom has preferably no fluorine atom. $R^{2I}$ is preferably one represented by —O—$CH_2$—$R^{2II}$—$CH_2$—O— where $R^{2II}$ represents a C1-C6 alkanediyl group which optionally has a fluorine atom.

Examples of the aklanediyl group for the ketal structure include a linear alkanediyl group such as a methylene group, an ethylene group, a propane-1,3-diyl group, a butane-1,4-diyl group, a pentane-1,5-diyl group and a hexane-1,6-diyl group; and a branched alkanediyl group such as an ethane-1,1-diyl group, a propane-1,2-diyl group, a butane-1,3-diyl group, a 2-methyl propane-1,3-diyl group, a 2-methyl propane-1,2-diyl group, a pentane-1,4-diyl group and 2-methyl butane-1,4-diyl group. Specific examples of the ketal structure include —O—$(CH_2)_2$—O—, —O—$(CH_2)_3$—O—, —O—$(CH_2)_4$—O—, —O—$CH_2$—$(CF_2)_2$—$CH_2$—O, —O—$CH_2$—$(CF_2)_3$—$CH_2$—O— and —O—$CH_2$—$(CF_2)_4$—$CH_2$—O—, preferably —O—$CH_2$—$(CF_2)_2$—$CH_2$—O— and —O—$CH_2$—$(CF_2)_3$—$CH_2$—O—, and still more preferably —O—$CH_2$—$(CF_2)_2$—$CH_2$—O—.

$R^2$ is preferably a C1-C12 aliphatic hydrocarbon group in which a methylene group can be replaced by an oxygen atom provided that the aliphatic hydrocarbon group has a ring structure, more preferably a C1-C12 aliphatic hydrocarbon group, still more preferably a C1-C6 alkyl group.

Specific examples of the compound represented by formula (I) include the following ones.

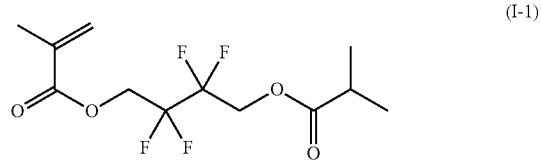

(I-1)

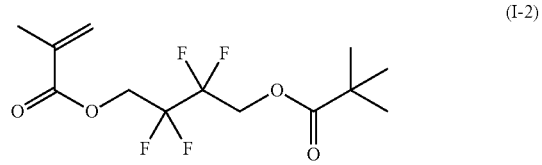

(I-2)

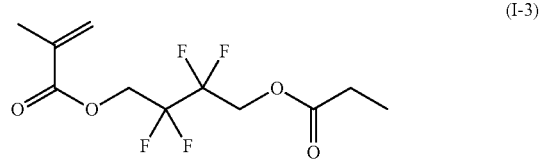

(I-3)

(I-4)
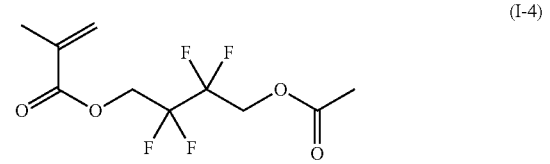

(I-5)
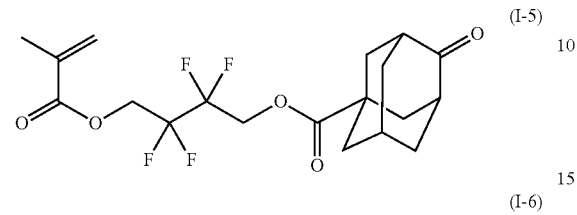

(I-6)
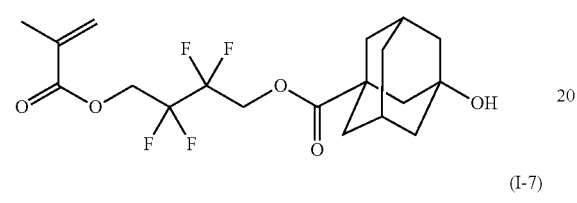

(I-7)
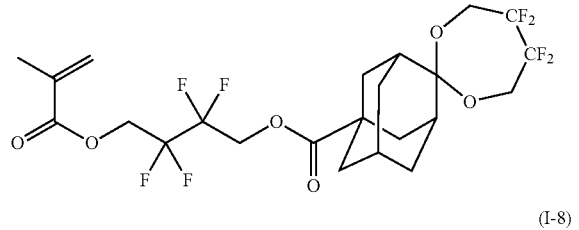

(I-8)
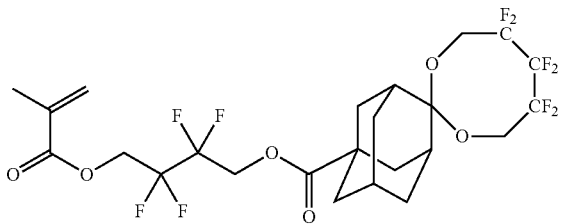

(I-9)
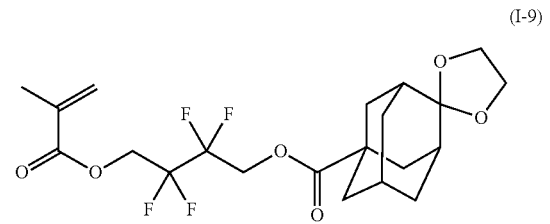

(I-10)
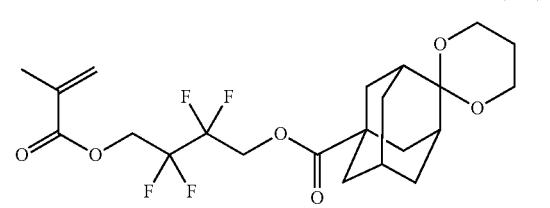

(I-11)
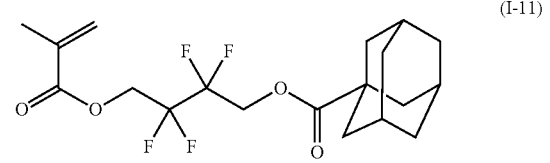

(I-12)
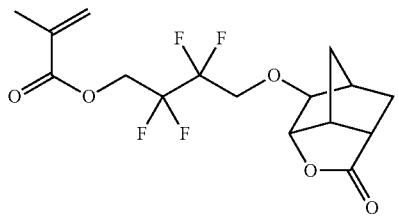

(I-13)
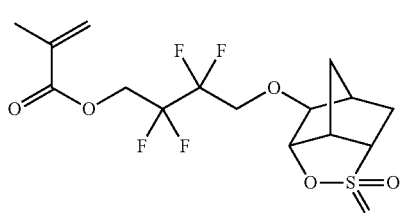

(I-14)
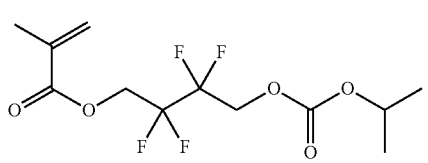

Specific examples of the compound further include those in which the methyl group corresponding to $R^1$ in each of formulae (I-1) to (I-14) has been replaced by a hydrogen atom.

The compound represented by formula (I) can be produced by reacting the compound represented by the formula (I-a) and the compound of the formula (I-b), in the presence of a basic catalyst such as pyridine or dimethylaminopyridine, in a solvent such as chloroform, tetrahydrofuran or toluene:

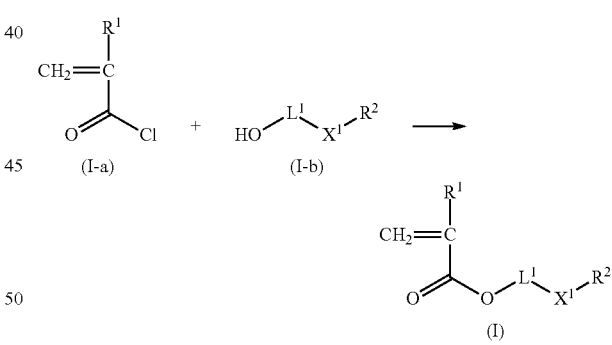

in which $R^1$, $R^2$, $X^1$ and $L^1$ are as defined above.

The reaction can be conducted at temperature of preferably −5° C. to 60° C., for 0.5 to 12 hours.

Examples of the compound of the formula (I-a) include the following one, which is available on the market.

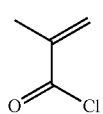

The compound represented by formula (I-b) can be produced by reacting the compound represented by the formula (I-c) and the compound of the formula (I-d), in the presence of a catalyst such as carbodiimidazole, in a solvent such as acetonitrile:

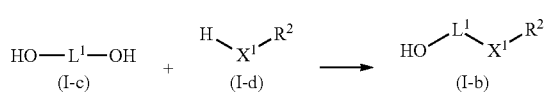

in which $R^2$, $X^1$ and $L^1$ are as defined above.

The reaction can be conducted at temperature of preferably 15° C. to 80° C., for 0.5 to 12 hours.

Examples of the compound of the formula (I-c), which is available on the market, include the following one.

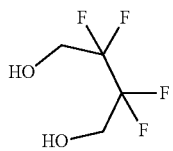

Examples of the compound of the formula (I-d), which is available on the market, include the following ones.

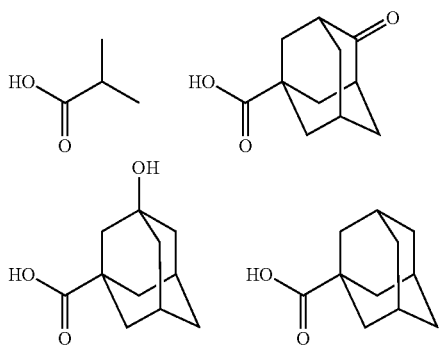

<Resin>

The resin of the disclosure has a structural unit derived from the compound represented by formula (I). The resin is sometimes referred to as "resin (X)", and the structural unit derived from the compound represented by formula (I) is sometimes referred to as "structural unit (I)"

In the resin (X), the content of the structural unit (I) is preferably 10 to 100% by mole, more preferably 20 to 100% by mole, still more preferably 30 to 100% by mole, further more preferably 50 to 100% by mole, based on all the structural units of the resin (X).

The resin (X) may have another structural unit such as a structural unit having a fluorine atom, a structural unit which has a hydrocarbon group having no acid-labile group, a structural unit having an acid-labile group, and a structural unit having no acid-labile group but having a hydroxyl group or a lactone ring.

The structural unit having a fluorine atom, the structural unit which has a hydrocarbon group having no acid-labile group and the structural unit having an acid-labile group are sometimes referred to as "structural unit (a4)", "structural unit (a5)", and "structural unit (a1)", respectively.

When the resin (X) has another structural unit than the structural unit (I), it has preferably the structural unit (a4) and/or the structural unit (a5), and more preferably the structural unit (a5). Examples of the structural unit (a4) include a structural unit represented by formula (a4-0).

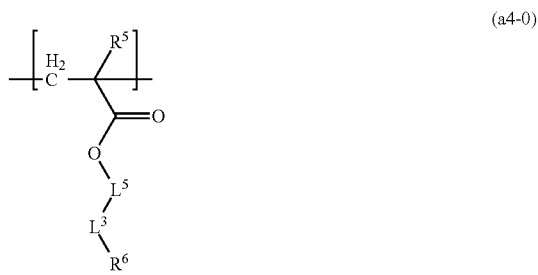

In the formula (a4-0), $R^5$ represents a hydrogen atom or a methyl group, $L^5$ represents a single bond or a C1-04 saturated aliphatic hydrocarbon group, $L^3$ represents a C1-C8 perfluoroalkanediyl group, or a C3-C12 perfluorocycloalkanediyl group, and $R^6$ represents a hydrogen atom or a fluorine atom.

Examples of the saturated aliphatic hydrocarbon group for $L^5$ include C1-C4 alkanediyl group, i.e., a linear alkanediyl group such as methylene, ethylene, propane-1,3-diyl, and butane-1,4-diyl groups; and a branched alkanediyl group such as ethane-1,1-diyl, propane-1,2-diyl, butane-1,3-diyl, 2-methylpropane-1,3-diyl and 2-methylpropane-1,2-diyl groups.

$L^5$ is preferably a single bond, methylene or ethylene group, and more preferably a single bond or methylene group.

Examples of the perfluoroalkanediyl group for $L^3$ include difluoromethylene, perfluoroethylene, perfluoro(ethylmethylene), perfluoropropane-1,3-diyl, perfluoropropane-1,2-diyl, perfluoropropane-2,2-diyl, perfluorobutane-1,4-diyl, perfluorobutane-2,2-diyl, perfluorobutane-1,2-diyl, perfluoropentane-1,5-diyl, perfluoropentane-2,2-diyl, perfluoropentane-3,3-diyl, perfluorohexane-1,6-diyl, perfluorohexane-2,2-diyl, perfluorohexane-3,3-diyl, perfluoroheptane-1,7-diyl, perfluoroheptane-2,2-diyl, perfluoroheptane-3,4-diyl, perfluoroheptane-4,4-diyl, perfluorooctan-1,8-diyl, perfluorooctan-2,2-diyl, perfluorooctan-3,3-diyl and perfluorooctan-4,4-diyl groups.

Examples of the perfluoro cycloalkanediyl group for $L^3$ include perfluorocyclohexanediyl, perfluorocyclopentanediyl, perfluorocycloheptanediyl and perfluoroadamantanediyl groups.

$L^3$ is preferably a C1-C6 perfluoroalkanediyl group, more preferably a C1-C3 perfluoroalkanediyl group.

Examples of the structural unit represented by formula (a4-0) include those as follow.

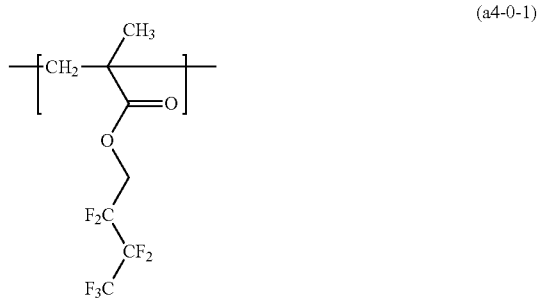

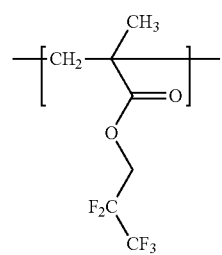
(a4-0-2)
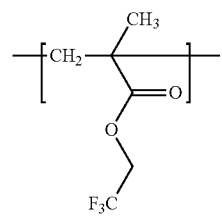
(a4-0-3)
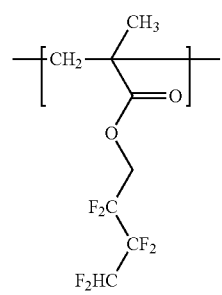
(a4-0-4)
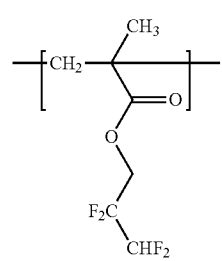
(a4-0-5)
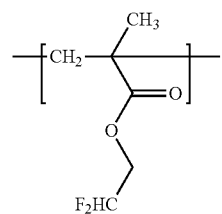
(a4-0-6)
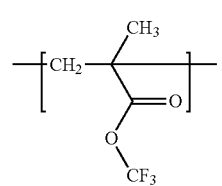
(a4-0-7)
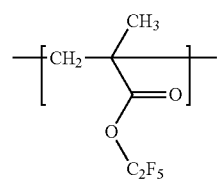
(a4-0-8)
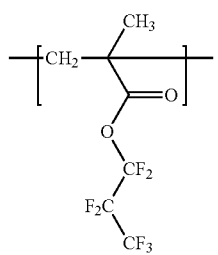
(a4-0-9)
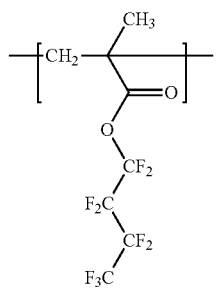
(a4-0-10)
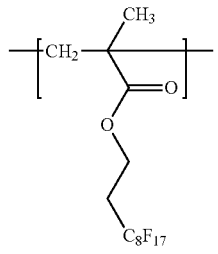
(a4-0-11)
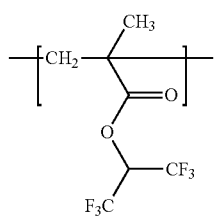
(a4-0-12)
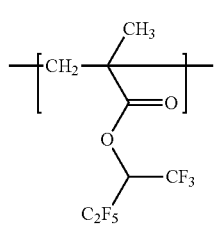
(a4-0-13)
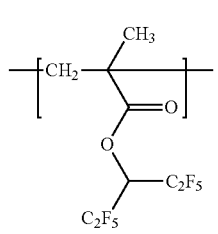
(a4-0-14)

-continued

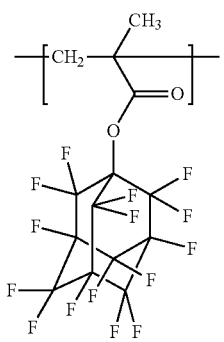
(a4-0-15)

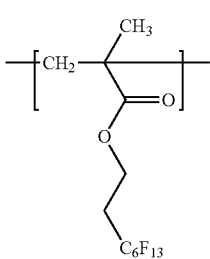
(a4-0-16)

Examples of the structural unit further include those in which the methyl group corresponding to $R^5$ in formulae (a4-0-1) to (a4-0-16) has been replaced by a hydrogen atom.

Examples of the structural unit (a4) further include those represented by formula (a4-1):

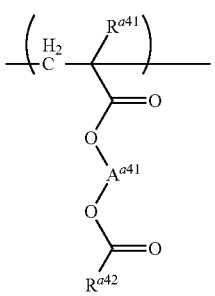
(a4-1)

wherein $R^{a41}$ represents a hydrogen atom or a methyl group, $R^{a42}$ represents an optionally substituted C1-C20 hydrocarbon group where a methylene group may be replaced by an oxygen atom or a carbonyl group, and $A^{a41}$ represents an optionally substituted C1-C6 alkanediyl group or a group represented by formula (a-g1):

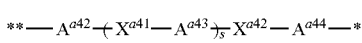
(a-g1)

wherein s represents 0 or 1, $A^{a42}$ and $A^{a44}$ each independently represent an optionally substituted C1-C5 aliphatic hydrocarbon group, $A^{a43}$ represents a single bond or an optionally substituted C1-C5 aliphatic hydrocarbon group, and $X^{a41}$ and $X^{a42}$ each independently represent —O—, —CO—, —CO—O— or —O—CO—, provided that the total number of the carbon atoms contained in the group of $A^{a42}$, $A^{a43}$, $A^{a44}$, $X^{a41}$ and $X^{a42}$ is 7 or less, at least one of $A^{a41}$ and $R^{a42}$ has a halogen atom as a substituent, and

* and ** represent a binding site, and * represents a binding site to —O—CO—$R^{a42}$.

The hydrocarbon group for $R^{a42}$ may be a chain aliphatic hydrocarbon group, a cyclic aliphatic hydrocarbon group, an aromatic hydrocarbon group, or a combination thereof.

The chain aliphatic hydrocarbon group and the cyclic aliphatic hydrocarbon group may have a carbon-carbon unsaturated bond, and is preferably a saturated aliphatic hydrocarbon group. Examples of the saturated aliphatic hydrocarbon group include a linear or branched alkyl group, a monocyclic or polycyclic alicyclic hydrocarbon group, and an aliphatic hydrocarbon group formed by combining the alkyl group and the alicyclic hydrocarbon group.

Examples of the chain aliphatic hydrocarbon group for $R^{a42}$ include an alkyl group such as methyl, ethyl, propyl, butyl, pentyl, hexyl, heptyl, octyl, decyl, and dodecyl groups.

Examples of the alicyclic hydrocarbon group for $R^{a42}$ include a cycloalkyl group such as cyclopentyl, cyclohexyl, cycloheptyl and cyclooctyl groups; and polycyclic hydrocarbon groups such as decahydronaphtyl, adamantyl and norbornyl groups, and the following group:

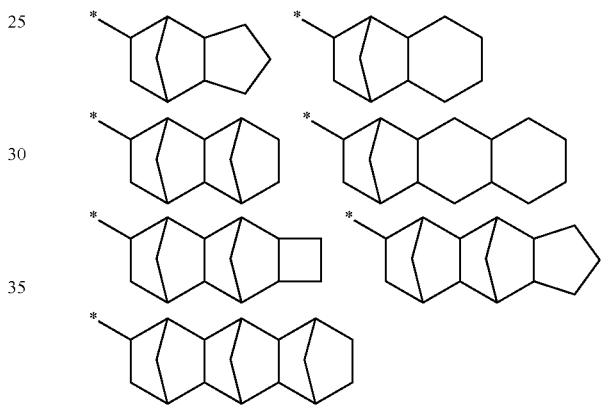

where * represents a binding site.

Examples of the aromatic hydrocarbon group for $R^{a42}$ include an aryl group such as phenyl, naphthyl, anthryl, biphenyl, phenanthryl and fluorenyl groups.

The hydrocarbon group for $R^{a42}$ is preferably a chain aliphatic hydrocarbon group, a cyclic aliphatic hydrocarbon group, and a combination thereof.

Examples of the substituent for $R^{a42}$ include a halogen atom and a group represented by formula (a-g3):

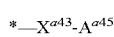
(a-g3)

wherein $X^{a43}$ represent an oxygen atom, a carbonyl group, a carbonyloxy group or an oxycarbonyl group, $A^{a45}$ represents a C1-C17 aliphatic hydrocarbon group that has a halogen atom, and

* represents a binding site.

Examples of the halogen atom for a substituent on $R^{a42}$ include fluorine, chlorine, bromine or iodine atom, and preferably a fluorine atom.

Examples of the aliphatic hydrocarbon group for $A^{a45}$ include the same ones as those for $R^{a42}$.

$R^{a42}$ is preferably an aliphatic hydrocarbon group that may have a halogen atom, and more preferably an alkyl group having a halogen atom and/or an aliphatic hydrocarbon group having the group represented by the formula (a-g3).

When $R^{a42}$ is an aliphatic hydrocarbon group having a halogen atom, an aliphatic hydrocarbon group having a fluorine atom is preferred, a perfluoroalkyl group or a perfluorocycloalkyl group are more preferred, a C1-C6 perfluoroalkyl group is still more preferred, a C1-C3 perfluoroalkyl group is particularly preferred.

Examples of the perfluoroalkyl group include perfluoromethyl, perfluoroethyl, perfluoropropyl, perfluorobutyl, perfluoropentyl, perfluorohexyl, perfluoroheptyl and perfluorooctyl groups. Examples of the perfluorocycloalkyl group include perfluorocyclohexyl group.

The aliphatic hydrocarbon group having the group represented by the formula (a-g3) is more preferably a group represented by formula (a-g2):

   (a-g2)

wherein $A^{a46}$ represents a C1-C15 aliphatic hydrocarbon group that may have a halogen atom, $X^{a44}$ represent a carbonyloxy group or an oxycarbonyl group, $A^{a47}$ represents a C1-C15 aliphatic hydrocarbon group that may have a halogen atom, provided that the total number of the carbon atoms contained in the group of $A^{a46}$, $X^{a44}$ and $A^{a47}$ is 18 or less, at least one of $A^{a46}$ and $A^{a47}$ has a halogen atom, and

* represents a binding site to a carbonyl group.

The aliphatic hydrocarbon group for $A^{a46}$ has preferably 1 to 6 carbon atoms, more preferably 1 to 3, carbon atoms.

The aliphatic hydrocarbon group for $A^{a47}$ has preferably 4 to 15 carbon atoms, more preferably 5 to 12 carbon atoms. $A^{a47}$ is more preferably a cyclohexyl group or an adamantyl group.

Preferred examples of *-$A^{a46}$-$X^{a44}$-$A^{a47}$ include the following ones.

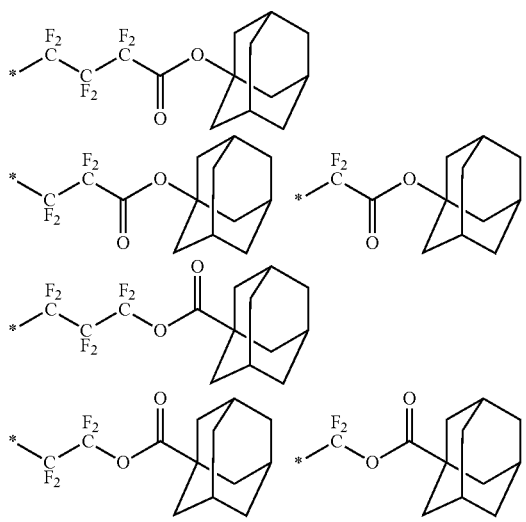

Examples of the alkanediyl group for $A^{a41}$ include a linear alkanediyl group such as methylene, ethylene, propane-1,3-diyl, butane-1,4-diyl, pentane-1, 5-diyl and hexane-1, 6-diyl groups;

a branched alkanediyl group such as propane-1,2-diyl, butan-1,3-diyl, 2-methylpropane-1,2-diyl, 1-methylbutane-1,4-diyl, 2-methylbutane-1,4-diyl groups.

Examples of the substituent on the alkanediyl group for $A^{a41}$ include a hydroxy group and a C1-C6 alkoxy group.

$A^{a41}$ is preferably a C1-C4 alkanediyl group, more preferably a C2-C4 alkanediyl group, and still more preferably ethylene group.

In the group represented by the formula (a-g1) (which is sometimes referred to as "group (a-g1)"), examples of the aliphatic hydrocarbon group for $A^{a42}$, $A^{a43}$ and $A^{a44}$ include methylene, ethylene, propane-1,3-diyl, propane-1,2-diyl, butane-1,4-diyl, 1-methylpropane-1,3-diyl, 2-methylpropane-1,3-diyl and 2-methylpropane-1,2-diyl groups.

Examples of the substituent on the aliphatic hydrocarbon group for $A^{a42}$, $A^{a43}$ and $A^{a44}$ include a hydroxy group and a C1-C6 alkoxy group.

s is preferably 0.

Examples of the group (a-g1) in which $X^{a42}$ represents an oxygen atom include the following ones. In each of the following formulae, * represent a binding site, and the * at the right side represents a binding site to —O—CO—$R^{a42}$.

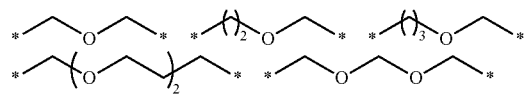

Examples of the group (a-g1) in which $X^{a42}$ represents a carbonyl group include the following ones. In each of the following formulae, * is as defined above.

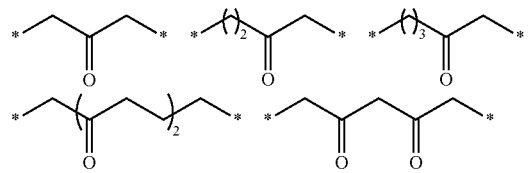

Examples of the group (a-g1) in which $X^{a42}$ represents a carbonyloxy group include the following ones. In each of the following formulae, * is as defined above.

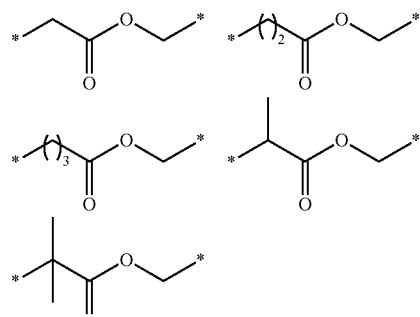

Examples of the group (a-g1) in which $X^{a42}$ represents an oxycarbonyl group include the following ones. In each of the following formulae, * is as defined above.

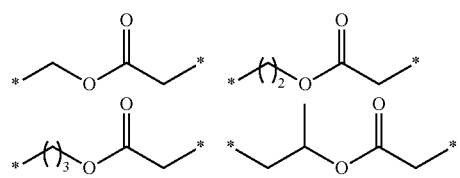

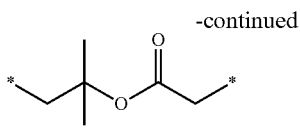

The structural unit represented by the formula (a4-1) is preferably structural units represented by formula (a4-2) and formula (a4-3):

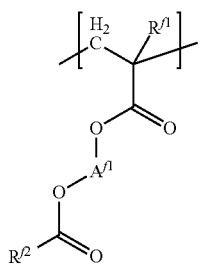
(a4-2)

wherein $R^{f1}$ represents a hydrogen atom or a methyl group, $A^{f1}$ represent a C1-C6 alkanediyl group, and $R^{f2}$ represents a C1-C10 hydrocarbon group that has a fluorine atom;

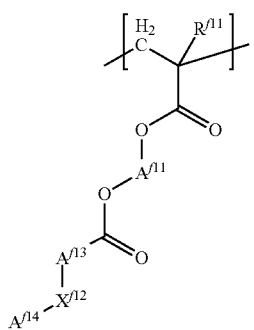
(a4-3)

where $R^{f11}$ represents a hydrogen atom or a methyl group,
$A^{f11}$ represent a C1-C6 alkanediyl group,
$A^{f13}$ represents a C1-C18 aliphatic hydrocarbon group that may have a fluorine atom,
$X^{f12}$ represents an oxycarbonyl group or a carbonyloxy group, and
$A^{f14}$ represents a C1-C17 aliphatic hydrocarbon group that may have a fluorine atom,
provided that at least one of $A^{f13}$ and $A^{f14}$ represents an aliphatic hydrocarbon group having a fluorine atom.

Examples of the alkanediyl group for $A^{f1}$ include a linear alkanediyl group such as methylene, ethylene, propane-1,3-diyl, propane-1,2-diyl, butane-1,4-diyl, pentane-1,5-diyl and hexane-1,6-diyl groups;

a branched alkanediyl group such as 1-methylpropane-1,3-diyl, 2-methylpropane-1,3-diyl, 2-methylpropane-1,2-diyl, 1-methylbutane-1,4-diyl and 2-methylbutane-1,4-diyl groups.

Examples of the hydrocarbon group for $R^{f2}$ include an aliphatic hydrocarbon group and an aromatic hydrocarbon group. The aliphatic hydrocarbon group includes chain and cyclic groups, and a combination thereof. The aliphatic hydrocarbon group is preferably an alkyl group and a cyclic aliphatic hydrocarbon group.

Examples of the alkyl group include methyl, ethyl, n-propyl, isopropyl, n-butyl, sec-butyl, tert-butyl, n-pentyl, n-hexyl, n-heptyl, n-octyl and 2-ethylhexyl groups.

Examples of the cyclic aliphatic hydrocarbon group include any of a monocyclic group and a polycyclic group. Examples of the monocyclic alicyclic hydrocarbon group include a cycloalkyl group such as cyclopropyl, cyclobutyl, cyclopentyl, cyclohexyl, methylcyclohexyl, dimethylcyclohexyl, cycloheptyl, cyclooctyl, and cyclodecyl groups. Examples of the polycyclic hydrocarbon groups includes decahydronaphthyl, adamantyl, 2-alkyladamantane-2-yl, 1-(adamantane-1-yl)alkane-1-yl, norbornyl, methylnorbornyl and isobornyl groups.

Examples of the hydrocarbon group having a fluorine atom for $R^{f2}$ include an alkyl group having a fluorine atom and an alicyclic hydrocarbon group having a fluorine atom.

Specific examples of an alkyl group having a fluorine atom include a fluorinated alkyl group such as difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,1,2,2,3,3-hexafluoropropyl, perfluoroethylmethyl, 1-(trifluoromethyl)-1,2,2,2-tetrafluoroethyl, perfluoropropyl, 1-(trifluoromethyl)-2,2,2-trifluoroethyl, perfluoropropyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoro)methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoropentyl, 1,1-bis(trifluoromethyl)2,2,3,3,3-pentafluoropropyl, 2-(perfluorobutyl)ethyl, 1,1,2,2,3,3,4,4,5,5-decafluorohexyl, 1,1,2,2,3,3,4,4,5,5,6,6-dodeca fluorohexyl, perfluoropentylmethyl and perfluorohexyl groups.

Examples of the alicyclic hydrocarbon group having a fluorine atom include a fluorinated cycloalkyl group such as perfluorocyclohexyl and perfluoroadamantyl groups.

In the formula (a4-2), $A^{f1}$ is preferably a C2-C4 alkanediyl group, and more preferably an ethylene group.

$R^{f2}$ is preferably a C1-C6 fluorinated alkyl group.

Examples of the alkanediyl group for $A^{f11}$ include the same ones as those for $A^{f1}$.

Examples of the aliphatic hydrocarbon group for $A^{f13}$ include any of a divalent chain or cyclic aliphatic hydrocarbon group, or a combination thereof. The aliphatic hydrocarbon group may have a carbon-carbon unsaturated bond, and is preferably a saturated aliphatic hydrocarbon group.

The aliphatic hydrocarbon group that may have a fluorine atom for $A^{f13}$ is preferably a saturated aliphatic hydrocarbon group that may have a fluorine atom, and more preferably perfluoroalkandiyl group.

Examples of the divalent chain aliphatic hydrocarbon that may have a fluorine atom include an alkanediyl group such as methylene, ethylene, propanediyl, butanediyl and pentanediyl groups; a perfluoroalkanediyl group such as difluoromethylene, perfluoroethylene, perfluoropropanediyl, perfluorobutanediyl and per fluoropentanediyl groups.

The divalent cyclic aliphatic hydrocarbon group that may have a fluorine atom is any of monocyclic hydrocarbon group and polycyclic hydrocarbon group.

Examples of the monocyclic aliphatic hydrocarbon group include cyclohexanediyl and perfluorocyclohexanediyl groups.

Examples of the polycyclic aliphatic hydrocarbon group include adamantanediyl, norbornanediyl and perfluoroadamantanediyl groups.

Examples of the aliphatic hydrocarbon group for $A^{f14}$ include any of a chain aliphatic hydrocarbon group, a cyclic aliphatic hydrocarbon group and a combination thereof. The aliphatic hydrocarbon group may have a carbon-carbon unsaturated bond, and is preferably a saturated aliphatic hydrocarbon group.

The aliphatic hydrocarbon group that may have a fluorine atom for $A^{f14}$ is preferably the saturated aliphatic hydrocarbon group that may have a fluorine atom.

Examples of the chain aliphatic hydrocarbon group that may have a halogen atom include difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, pentyl, hexyl, perfluorohexyl, heptyl, perfluoroheptyl, octyl and perfluorooctyl groups.

The cyclic aliphatic hydrocarbon group that may have a fluorine atom may be any of a monocyclic hydrocarbon group and a polycyclic hydrocarbon group. Examples of the group containing the monocyclic aliphatic hydrocarbon group include cyclopropylmethyl, cyclopropyl, cyclobutylmethyl, cyclopentyl, cyclohexyl and perfluorocyclohexyl groups. Examples of the group containing the polycyclic aliphatic hydrocarbon group include adamantyl, adamantylmethyl, norbornyl, norbornylmethyl, perfluoroadamantyl and perfluoroadamantylmethyl groups.

In the formula (a4-3), $A^{f11}$ is preferably an ethylene group.

The aliphatic hydrocarbon group for $A^{f13}$ is preferably a C1-C6 aliphatic hydrocarbon group, more preferably a C2-C3 aliphatic hydrocarbon group.

The aliphatic hydrocarbon group for $A^{f14}$ is preferably a C3-C12 aliphatic hydrocarbon group, more preferably a C3-C10 aliphatic hydrocarbon group. Among these, $A^{f14}$ is preferably a group containing a C3-C12 alicyclic hydrocarbon group, more preferably cyclopropylmethyl, cyclopentyl, cyclohexyl, norbornyl and adamantyl groups.

Examples of the structural unit represented by formula (a4-2) include structural units represented by formula (a4-1-1) to formula (a4-1-22).

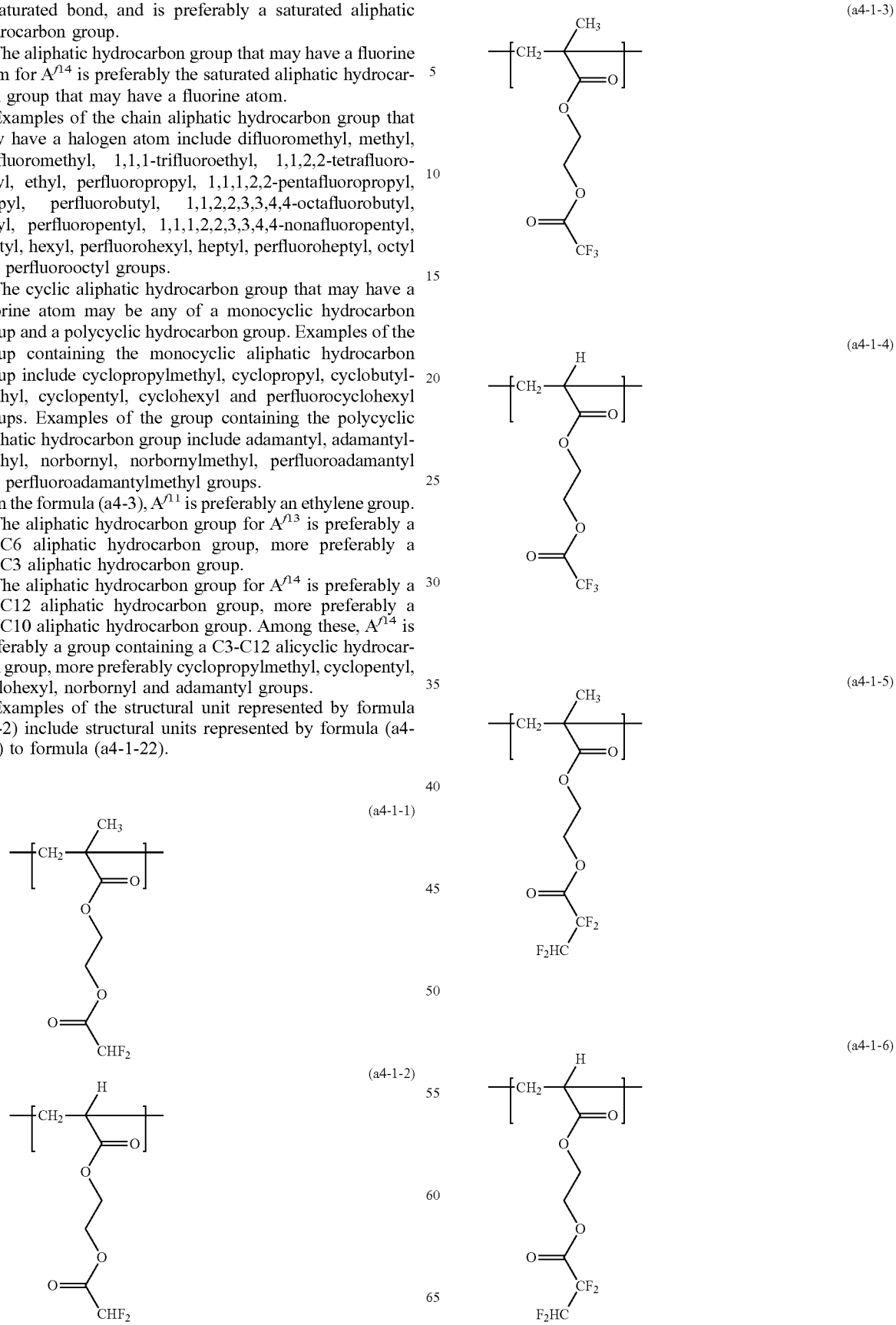

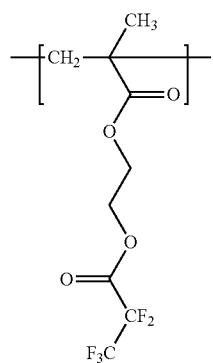 (a4-1-7)
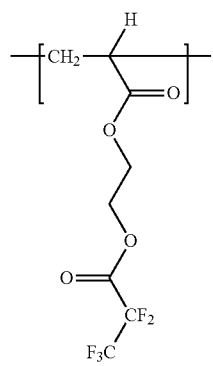 (a4-1-8)
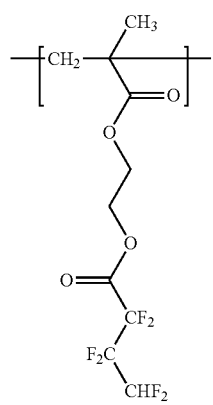 (a4-1-9)
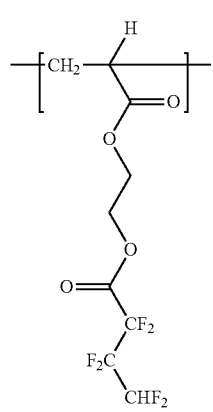 (a4-1-10)
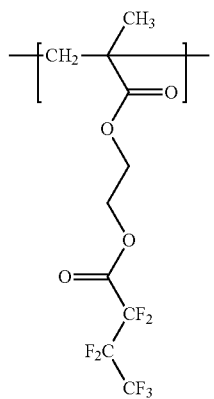 (a4-1-11)
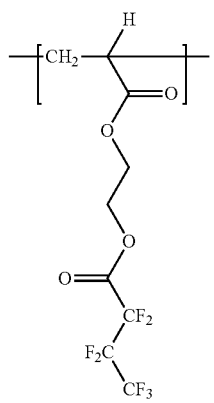 (a4-1-12)
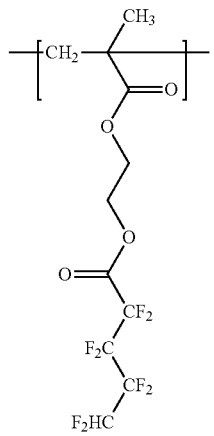 (a4-1-13)

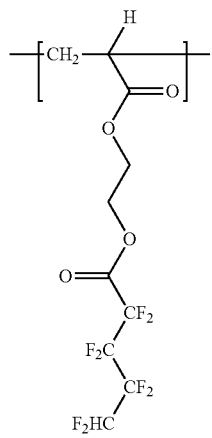
(a4-1-14)
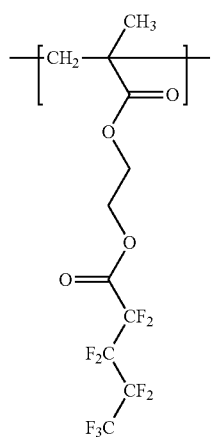
(a4-1-15)
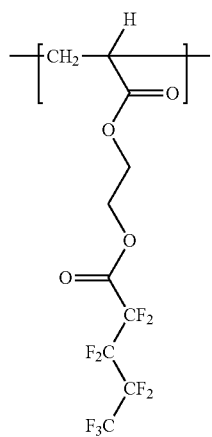
(a4-1-16)
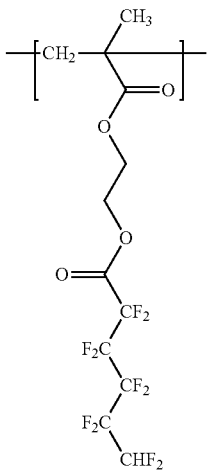
(a4-1-17)
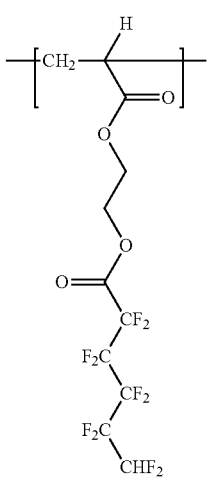
(a4-1-18)
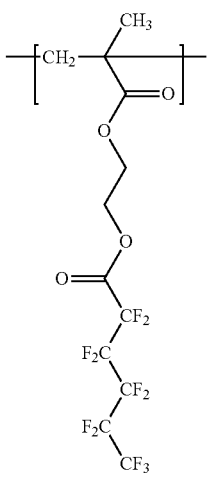
(a4-1-19)

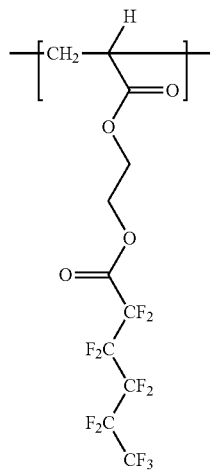
(a4-1-20)
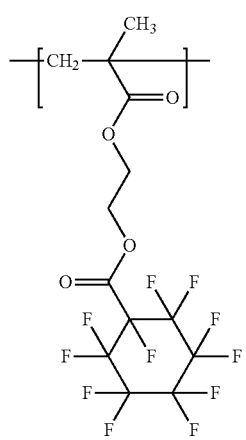
(a4-1-21)
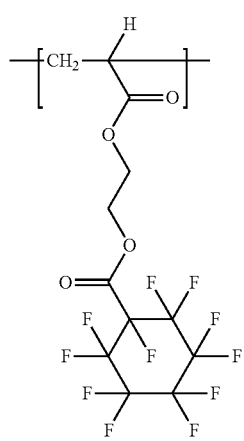
(a4-1-22)
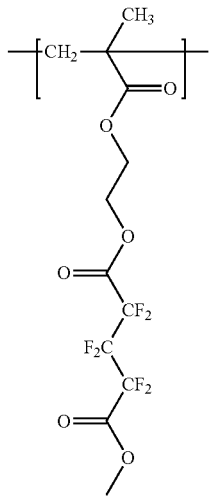
(a4-1'-1)
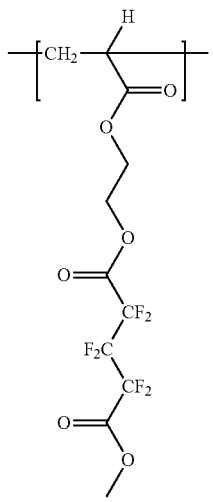
(a4-1'-2)
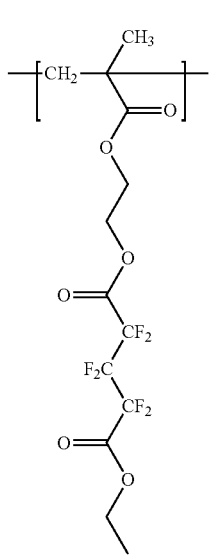
(a4-1'-3)
Examples of the structural unit represented by formula (a4-3) include structural units represented by formula (a4-1'-1) to formula (a4-1'-22).

(a4-1'-4)
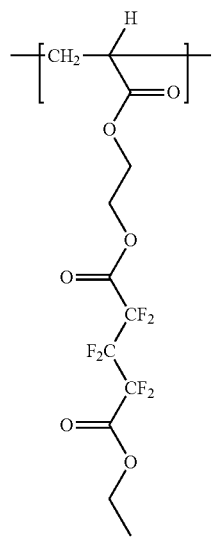
(a4-1'-5)
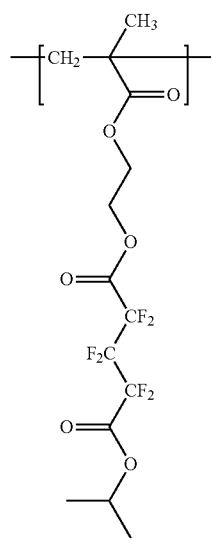
(a4-1'-6)
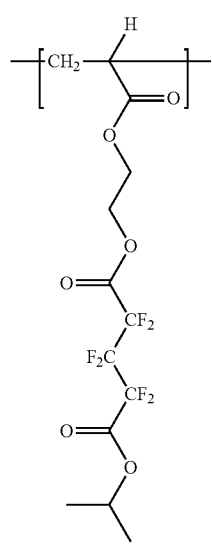
(a4-1'-7)
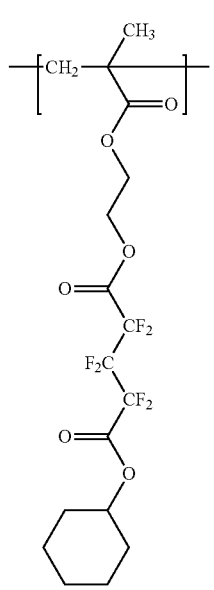
(a4-1'-8)
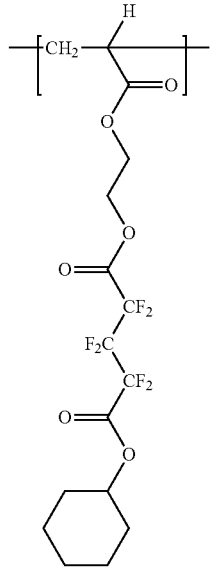

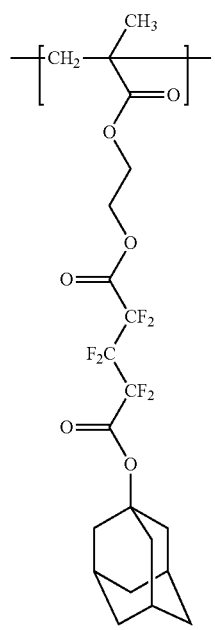 (a4-1'-9)
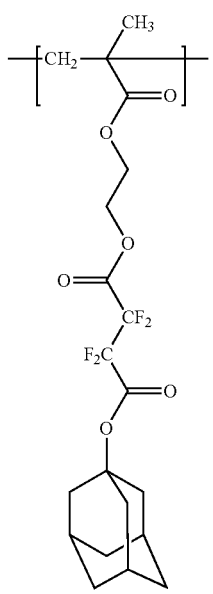 (a4-1'-11)
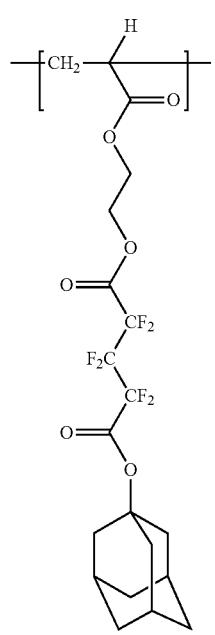 (a4-1'-10)
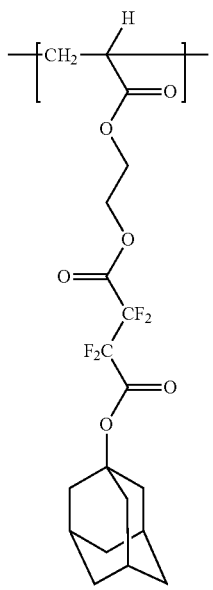 (a4-1'-12)

(a4-1'-13)
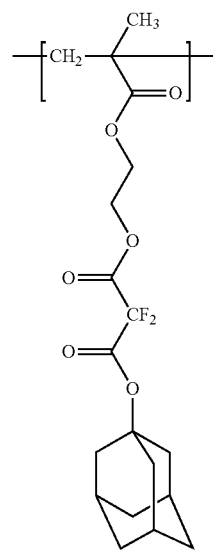
(a4-1'-15)
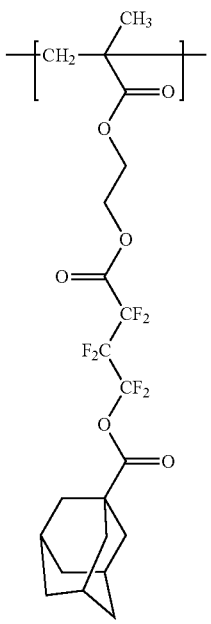
(a4-1'-14)
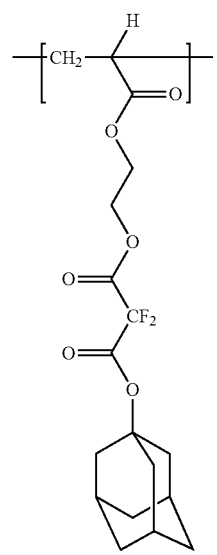
(a4-1'-16)
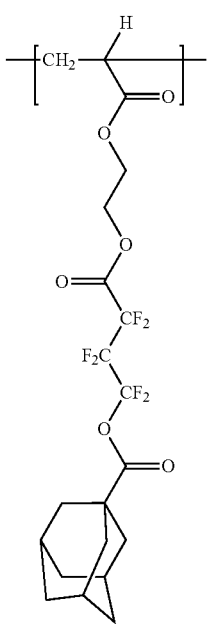

(a4-1'-17)
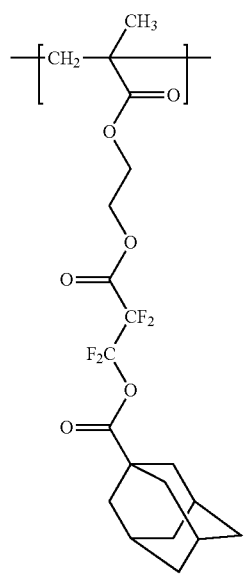
(a4-1'-18)
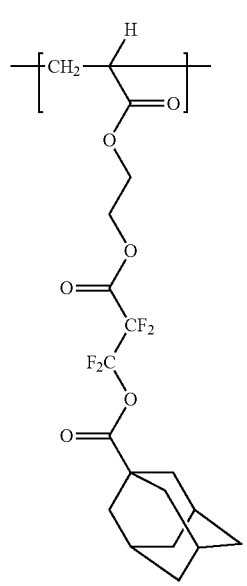
(a4-1'-19)
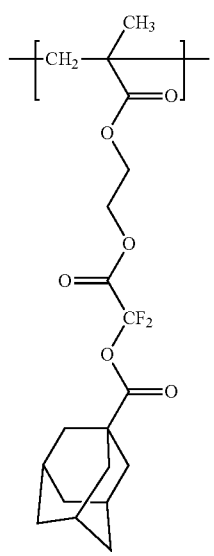
(a4-1'-20)
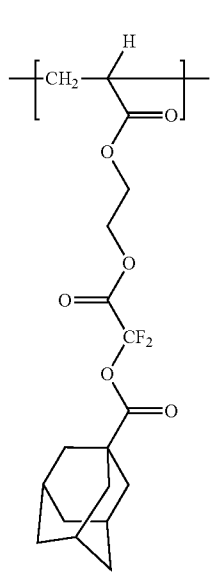
(a4-1'-21)
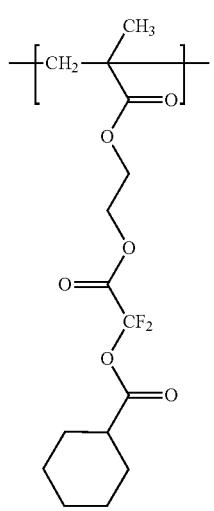

(a4-1'-22)

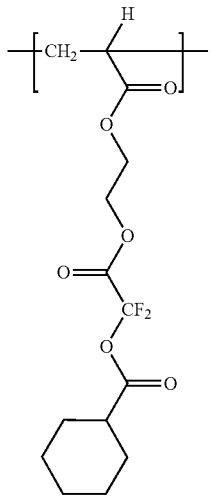

Examples of the structural unit (a4) include a structural unit represented by formula (a4-4):

(a4-4)

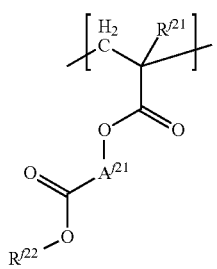

wherein $R'^{21}$ represents a hydrogen atom or a methyl group, $A'^{21}$ represents *—$(CH_2)_{j1}$—, *—$(CH_2)_{j2}$—O—$(CH_2)_{j3}$— or *—$(CH_2)_{j4}$—CO—O—$(CH_2)_{j5}$—, where * represents a binding site to an oxygen atom, j1 to j5 each independently represents an integer of 1 to 6, and $R'^{22}$ represents a C1-C10 hydrocarbon group having a fluorine atom. Examples of the hydrocarbon group having a fluorine atom for $R'^{22}$ include the same ones as those for $R^2$ in the formula (a4-2). $R'^{22}$ is preferably a C1-C10 alkyl group having a fluorine atom or a C3-C10 alicyclic hydrocarbon group having a fluorine atom, more preferably a C1-C10 alkyl group having a fluorine atom, and still more preferably a C1-C6 alkyl group having a fluorine atom.

In the formula (a4-4), $A'^{21}$ is preferably —$(CH_2)_{j1}$—, more preferably a methylene group or an ethylene group, and still more preferably a methylene group.

Examples of the structural unit represented by the formula (a4-4) include the following ones.

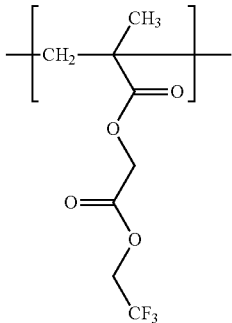 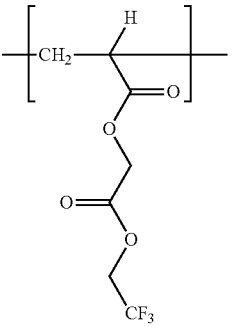

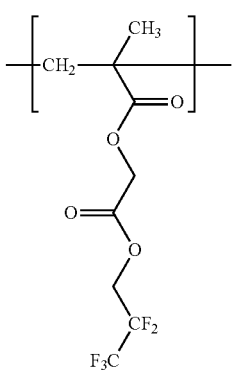 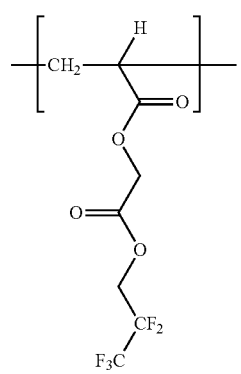

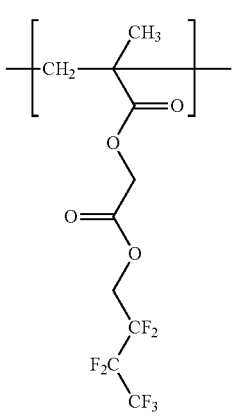 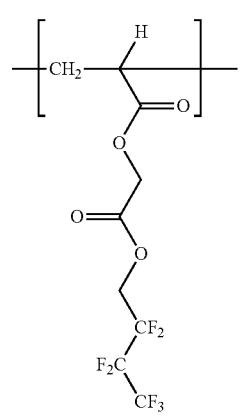

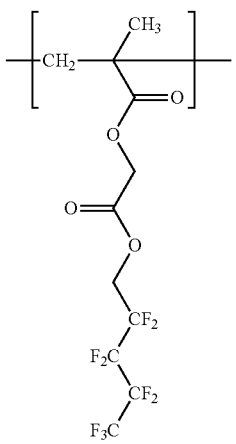 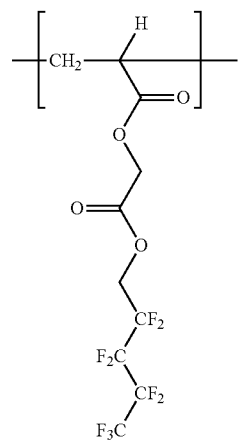

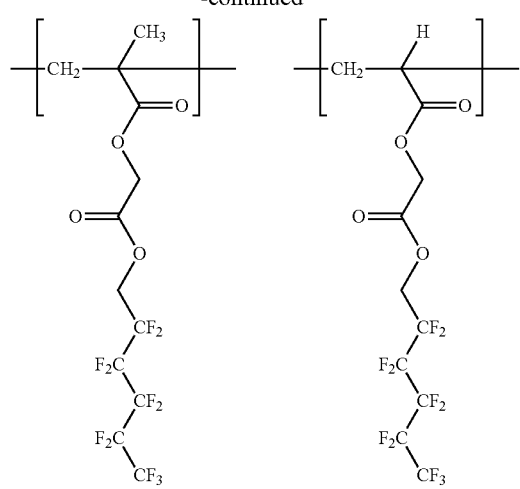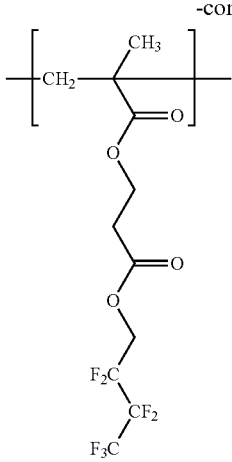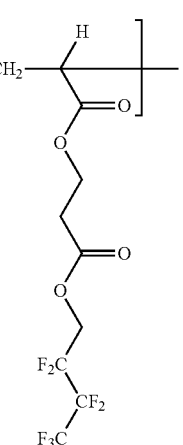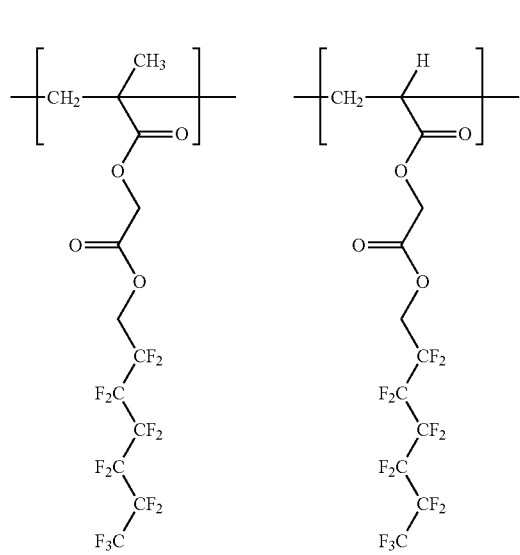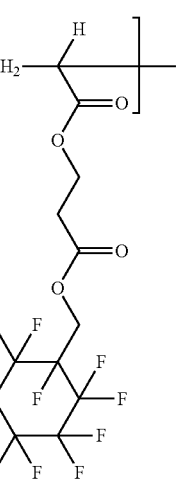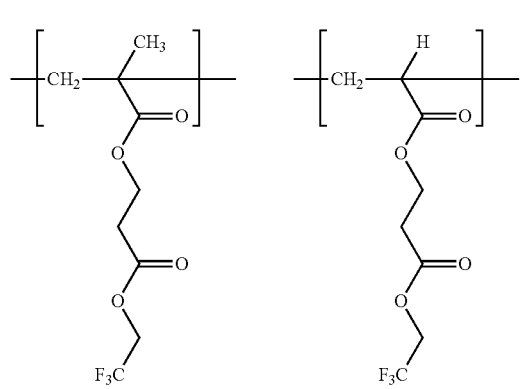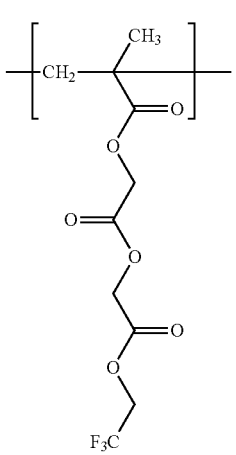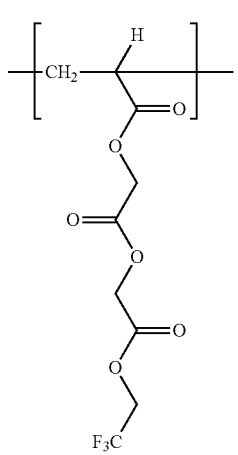

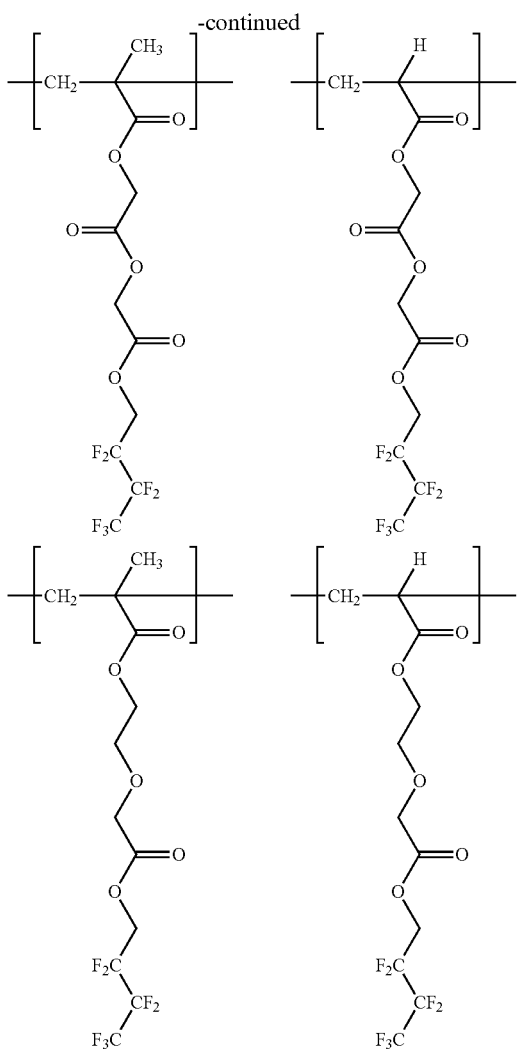

When Resin (X) has the structural unit (a4), the content thereof is usually 1 to 20% by mole, preferably 2 to 15% by mole, and more preferably 3 to 10% by mole, based on all the structural units of the resin (X).

The structural unit which has a hydrocarbon group having no acid-labile group, which is sometimes referred to as the "structural unit (a5)", may have a linear, branched or cyclic hydrocarbon group, preferably an alicyclic hydrocarbon group.

Examples of the structural unit (a5) include one represented by formula (a5-1):

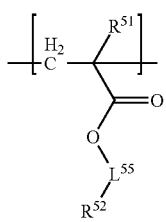

(a5-1)

where $R^{51}$ represents a hydrogen atom or a methyl group; $R^{52}$ represents a C3-C18 alicyclic hydrocarbon group where a hydrogen atom can be replaced by a C1-C8 aliphatic hydrocarbon group or a hydroxy group, provided that the alicyclic hydrocarbon group has no aliphatic hydrocarbon group on the carbon atom bonded to $L^{55}$;

and $L^{55}$ represents a single bond or a C1-C18 divalent saturated hydrocarbon group where a methylene group can be replaced by an oxygen atom or carbonyl group.

The alicyclic hydrocarbon group represented by $R^{52}$ may be monocyclic or polycyclic one. Examples of the alicyclic hydrocarbon group include a monocyclic hydrocarbon group such as a C3-C18 cycloalkyl group (e.g. a cyclopropyl group, a cyclobutyl group, a cyclopentyl group, a cyclohexyl group) and a polycyclic alicyclic hydrocarbon group such as an adamantyl group, or a norbornyl group.

Examples of the alicyclic hydrocarbon group having a substituent include a 3-hydroxyadamantyl group, and a 3-methyladamantyl group. Examples of the C1-C8 aliphatic hydrocarbon group include an alkyl group such as methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group having a substituent for $R^{52}$ include 3-hydroxyadamantyl group and 3-methyladamantyl group. $R^{52}$ is preferably an unsubstituted C3-018 alicyclic hydrocarbon group, and more preferably an adamantyl, norbornyl or cyclohexyl group.

Examples of the divalent saturated hydrocarbon group for $L^{55}$ include a divalent saturated aliphatic hydrocarbon group and a divalent saturated alicyclic hydrocarbon group, and a divalent saturated aliphatic hydrocarbon group is preferred.

Examples of the divalent saturated aliphatic hydrocarbon group include an alkanediyl group such as methylene, ethylene, propanediyl, butanediyl and pentanediyl groups.

Examples of the divalent saturated alicyclic hydrocarbon group include any of a monocyclic group and a polycyclic group. Examples of the monocyclic group include cycloalkanediyl group such as cyclopentanediyl and cyclohexanediyl groups. Examples of the polycyclic group include adamantanediyl and norbornanediyl groups.

Examples of the saturated hydrocarbon group in which a methylene group has been replaced by an oxygen atom or a carbonyl group include groups represented by formula (L1-1) to formula (L1-4). In formula (L1-1) to formula (L1-4), * represents a binding site to an oxygen atom.

  (L1-1)

  (L1-2)

  (L1-3)

  (L1-4)

In the formulae, $X^{x1}$ represents an oxycarbonyl group or a carbonyloxy group, $L^{x1}$ represents a C1-C16 divalent saturated aliphatic hydrocarbon group, and $L^{x2}$ represents a single bond or a C1-C15 divalent saturated aliphatic hydrocarbon group, provided that the total number of the carbon atoms contained in the groups of $L^{X1}$ and $L^{X2}$ is 16 or less;

$L^{X3}$ represents a single bond or a C1-C17 divalent saturated aliphatic hydrocarbon group, and $L^{X4}$ represents a single bond or a C1-C16 divalent saturated aliphatic hydrocarbon group, provided that the total number of the carbon atoms contained in the groups of $L^{X3}$ and $L^{X4}$ is 17 or less;

$L^{X5}$ represents a C1-C15 divalent saturated aliphatic hydrocarbon group, and $L^{X6}$ and $L^{X7}$ each independently represent a single bond or a C1-C14 divalent saturated aliphatic hydrocarbon group, provided that the total number of the carbon atoms contained in the groups of $L^{X5}$, $L^{X6}$ and $L^{X7}$ is 15 or less;

$L^{X8}$ and $L^{X9}$ each independently represent a single bond or a C1-C12 divalent saturated aliphatic hydrocarbon group, and $W^{X1}$ represents a C3-C15 divalent saturated alicyclic hydrocarbon group, provided that the total number of the carbon atoms contained in the groups of $L^{X8}$, $L^{X9}$ and $W^{X1}$ is 15 or less.

$L^{X1}$ is preferably a C1-C8 divalent saturated aliphatic hydrocarbon group, and more preferably a methylene group or an ethylene group.

$L^{X2}$ is preferably a single bond or a C1-C8 divalent saturated aliphatic hydrocarbon group, and more preferably a single bond.

$L^{X3}$ is preferably a C1-C8 divalent saturated aliphatic hydrocarbon group.

$L^{X4}$ is preferably a single bond or a C1-C8 divalent saturated aliphatic hydrocarbon group.

$L^{X5}$ is preferably a C1-C8 divalent saturated aliphatic hydrocarbon group, and more preferably a methylene group or an ethylene group.

$L^{X6}$ is preferably a single bond or a C1-C8 divalent saturated aliphatic hydrocarbon group, and more preferably a methylene group or an ethylene group.

$L^{X7}$ is preferably a single bond or a C1-C8 divalent saturated aliphatic hydrocarbon group.

$L^{X8}$ is preferably a single bond or a C1-C8 divalent saturated aliphatic hydrocarbon group, and more preferably a single bond or a methylene group.

$L^{X9}$ is preferably a single bond or a C1-C8 divalent saturated aliphatic hydrocarbon group, and more preferably a single bond or a methylene group.

$W^{X1}$ is preferably a C3-C10 divalent saturated alicyclic hydrocarbon group, and more preferably a cyclohexanediyl group and an adamantanediyl group.

Examples of the group represented by the formula (L1-1) include the following ones.

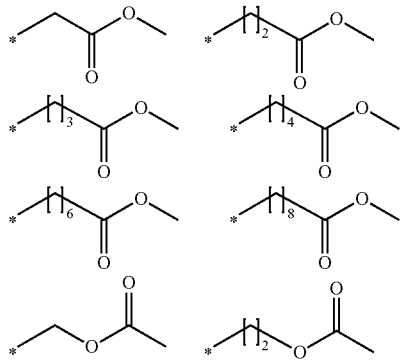

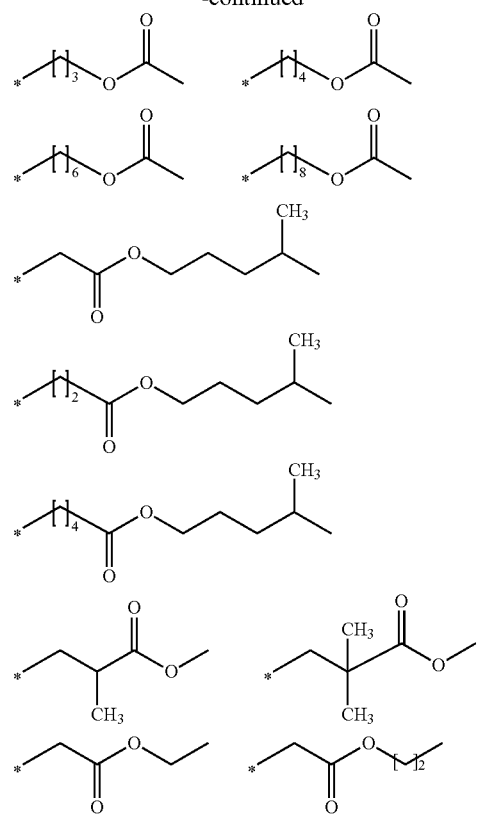

Examples of the group represented by the formula (L1-2) include the following ones.

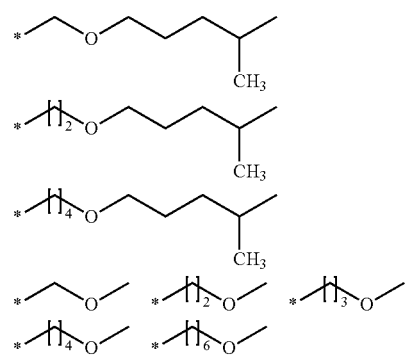

Examples of the group represented by the formula (L1-3) include the following ones.

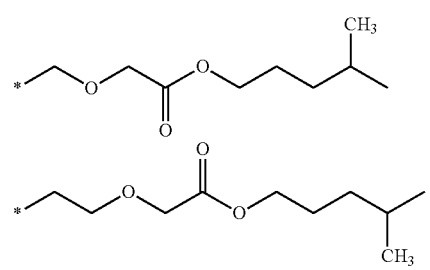

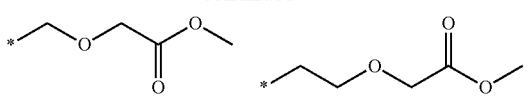
Examples of the group represented by the formula (L1-4) include the following ones.
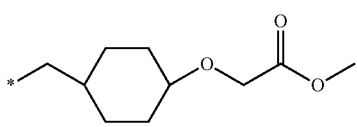
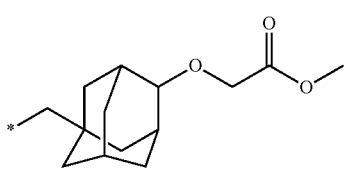
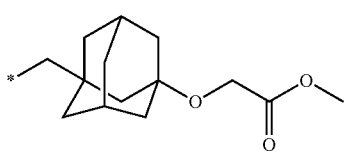
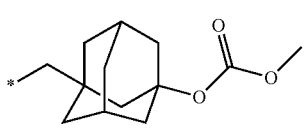
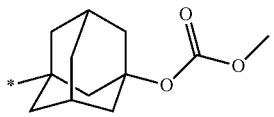
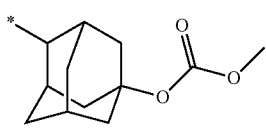
$L^{55}$ is preferably a single bond, a methylene group, an ethylene group, or the group represented by the formula (L1-1).
Examples of the structural unit represented by formula (a5-1) include the following ones.
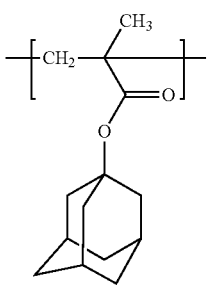
(a5-1-1)
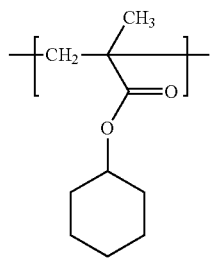
(a5-1-2)
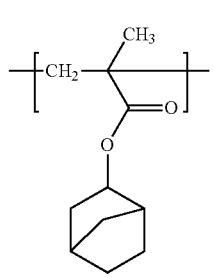
(a5-1-3)
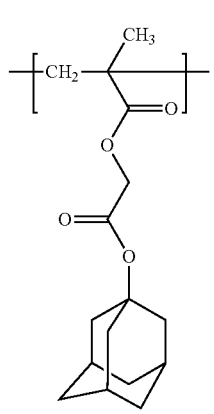
(a5-1-4)
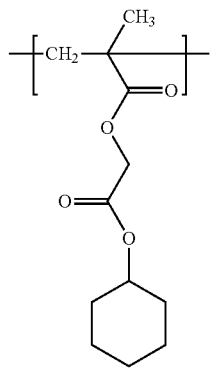
(a5-1-5)

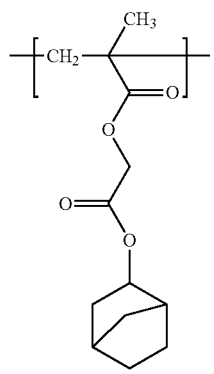 (a5-1-6)
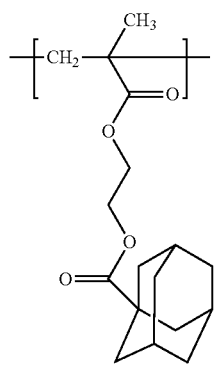 (a5-1-7)
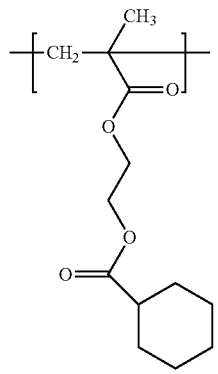 (a5-1-8)
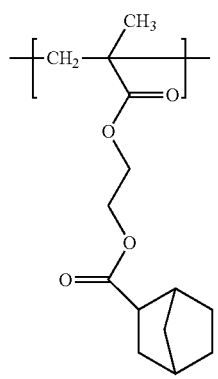 (a5-1-9)
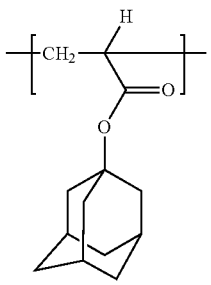 (a5-1-10)
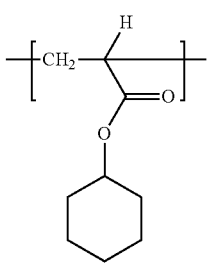 (a5-1-11)
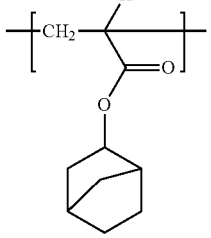 (a5-1-12)
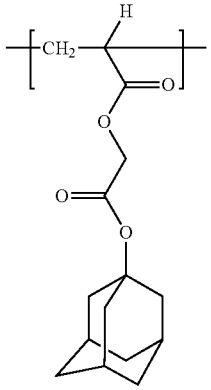 (a5-1-13)
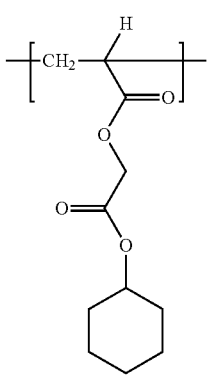 (a5-1-14)

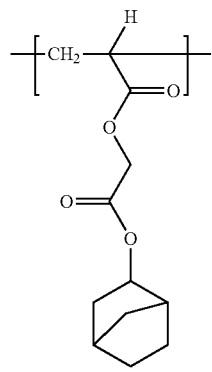 (a5-1-15)
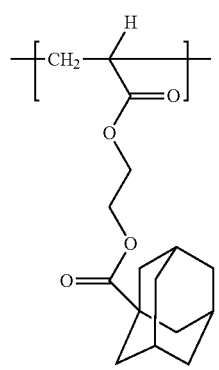 (a5-1-16)
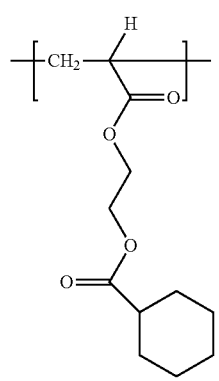 (a5-1-17)
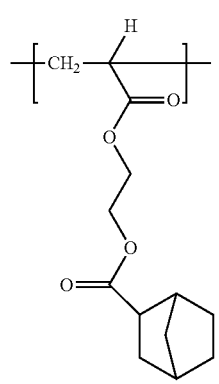 (a5-1-18)
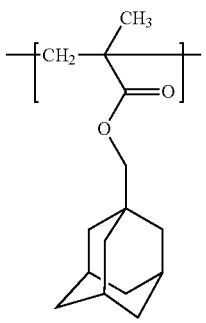 (a5-1-19)
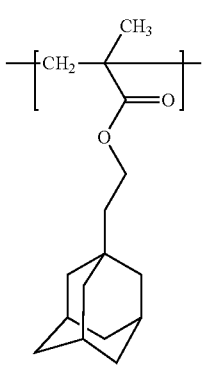 (a5-1-20)
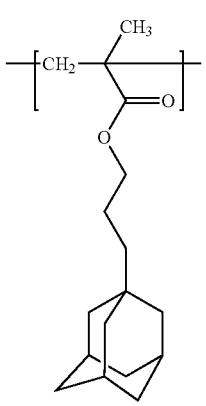 (a5-1-21)
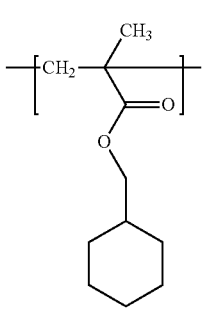 (a5-1-22)

(a5-1-23)
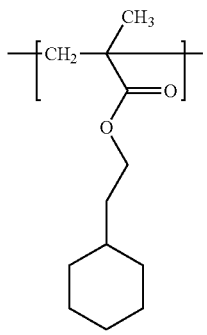

(a5-1-24)
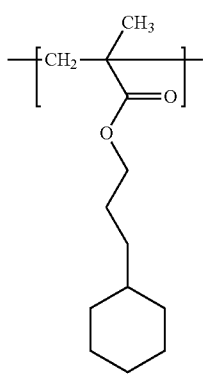

(a5-1-25)
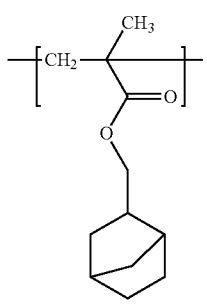

(a5-1-26)
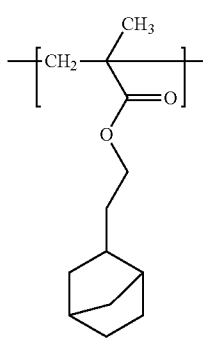

(a5-1-27)
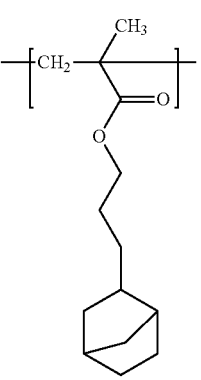

Examples of the structural units represented by formula (a5-1) include structural units represented by formulae (a5-19) to (a5-27) in which a methyl group corresponding to $R^{51}$ has been replaced by a hydrogen atom.

When the resin (X) further has the structural unit represented by formula (a5), the content thereof is preferably 1 to 70% by mole, more preferably 2 to 60% by mole, and still more preferably 3 to 50% by mole, based on all the structural units of the resin.

The resin (X) can be produced according to known polymerization methods such as radical polymerization, using the compound of formula (I) and monomers corresponding to the structural units other than the structural unit (I).

The resin (X) has usually 6000 or more of the weight-average molecular weight, preferably 7000 or more of the weight-average molecular weight, still more preferably 8000 or more of the weight-average molecular weight. The resin (X) has usually 80000 or less of the weight-average molecular weight, preferably 60000 or less of the weight-average molecular weight, still more preferably 20000 or less of the weight-average molecular weight.

<Photoresist Composition>

The photoresist composition of the disclosure has the resin (X), a resin having an acid-labile group, which resin is sometimes referred to as "resin (A)", and an acid generator.

Herein, the "acid-labile group" means a functional group having a leaving group which is removed therefrom by contacting with an acid to give a hydrophilic group such as a hydroxy group or carboxy group. The photoresist composition may further contain a quencher or a solvent. The quencher includes a salt capable of generating an acid weaker in acidity than that generated from an acid generator. The photoresist composition preferably further contains a quencher or a solvent, more preferably both of them.

The resin (A) has an acid-labile group, specifically a structural unit having an acid-labile group. The structural unit having an acid-labile group is sometimes referred to as "structural unit (a1)".

The resin (A) may further have a structural unit other than the structural units (a1) and (I). This other structural unit is described later.

The structural unit (a1) is derived from a monomer having an acid-labile group which monomer is sometimes referred to as "monomer (a1)".

Specific examples of the acid-labile group include a group represented by the formula (1):

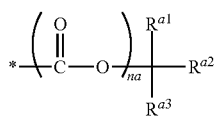
(1)

wherein $R^{a1}$, $R^{a2}$ and $R^{a3}$ each independently represent a C1-C8 alkyl group, a C3-C20 alicyclic hydrocarbon group or a combination of them, or $R^{a1}$ and $R^{a2}$ may be bonded each other to form a C3-C20 divalent alicyclic hydrocarbon group together with the carbon atom bonded to both of them, "na" represents an integer of 0 or 1, and * represents a binding site, and
a group represented by the formula (2):

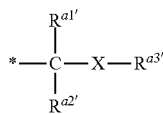
(2)

wherein $R^{a1'}$ and $R^{a2'}$ each independently represent a hydrogen atom or a C1-C12 hydrocarbon group, and $R^{a3'}$ represents a C1-C20 hydrocarbon group, or $R^{a3'}$ is bonded to $R^{a1'}$ or $R^{a2'}$ to form a C3-C20 divalent heterocyclic group with a carbon atom and X bonded thereto, a methylene group in the divalent heterocyclic group may be replaced by —O— or —S—, X represents an oxygen atom or a sulfur group, and * represents a binding site.

Specific examples of the C1-C8 alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic.

Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, and the followings.

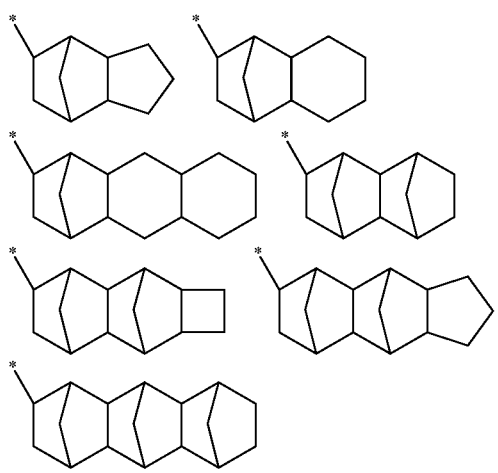

The alicyclic hydrocarbon group preferably has C3-C16 carbon atoms. The combination of alkyl group and alicyclic hydrocarbon group includes a methylcyclohexyl group, a dimethylcyclohexyl group, a methylnorbornyl group, a cyclohexylmethyl group, an adamantylmethyl group, a norbornylethyl group.

When $R^{a1}$ and $R^{a2}$ of formula (1) are bonded each other to forma C2-C20 divalent hydrocarbon group, examples of the moiety represented by —C($R^{a1}$)($R^{a2}$)($R^{a3}$) include the following groups and the ring preferably has 3 to 12 carbon atoms:

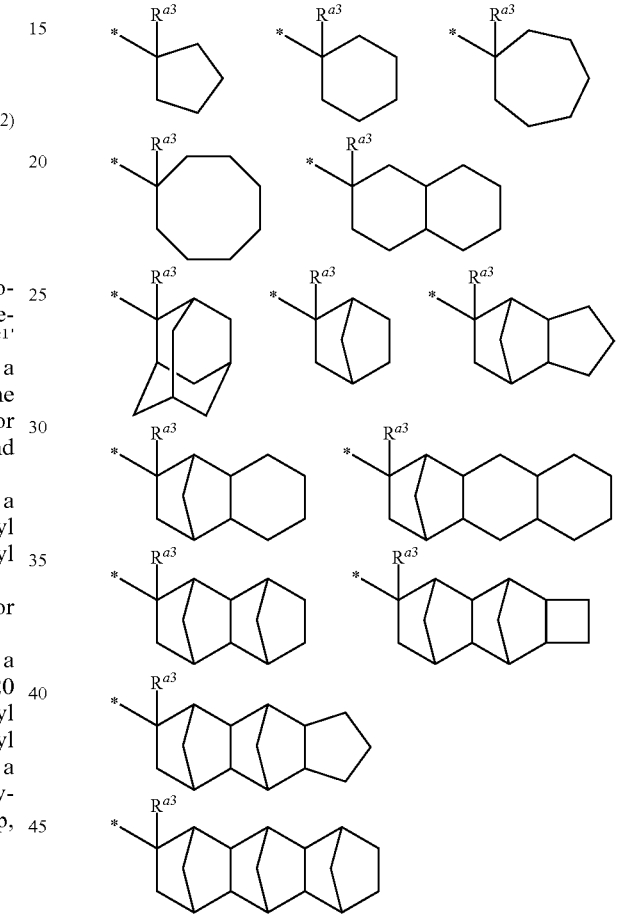

wherein $R^{a3}$ is as defined above and * represents a binding site to —O— of formula (1).

As the group represented by the formula (1), preferred are 1,1'-dialkylalkoxylcarbonyl group, i.e., the group represented by the formula (1) wherein $R^{a1}$, $R^{a2}$ and $R^{a3}$ each independently represent a C1-C8 alkyl group, preferably a tert-butyl group;

2-alkyladaman-2-tyloxycarbonyl group, i.e., the group represented by the formula (1) wherein $R^{a1}$ and $R^{a2}$ are bonded each other to form an adamantyl group and $R^{a3}$ is a C1-C8 alkyl group; and a 1-(1-adaman-1-tyl)-1-alkylalkoxycarbonyl group, i.e., the group represented by the formula (1) wherein $R^{a1}$ and $R^{a2}$ are C1-C8 alkyl groups and $R^{a3}$ is an adamantyl group.

As to formula (2), examples of the hydrocarbon group include an alkyl group, an alicyclic hydrocarbon group and an aromatic hydrocarbon group.

Examples of the alkyl group and the alicyclic hydrocarbon group include the same as described above. Examples of the aromatic hydrocarbon group include an aryl group such as a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group.

Examples of the divalent heterocyclic group formed by bonding with $R^{a2'}$ or $R^{a3'}$ with a carbon atom and X bonded thereto include the following groups.

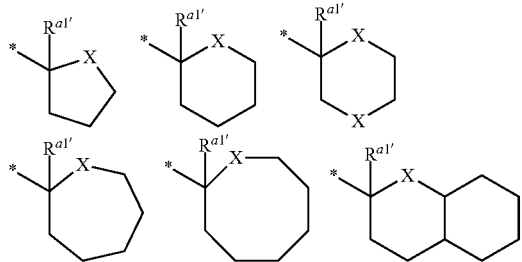

In each formula, $R^{a1'}$ and X are as defined above. Preferably, at least one of $R^{a1'}$ and $R^{a2'}$ is a hydrogen atom. Examples of the group represented by formula (2) include the following.

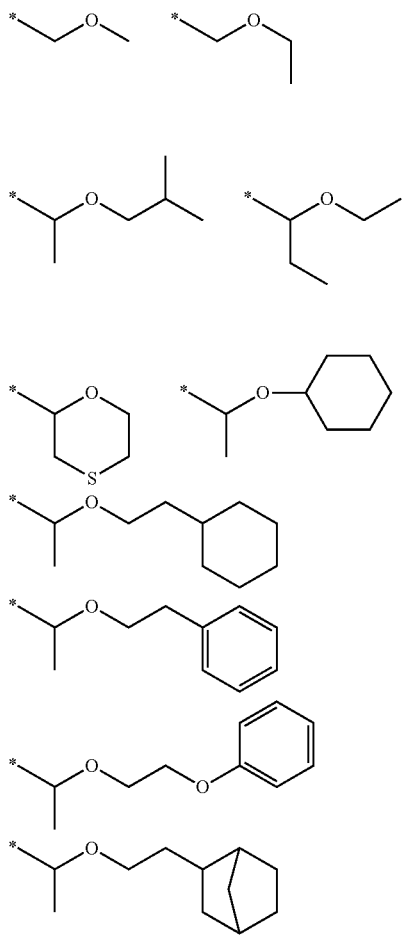

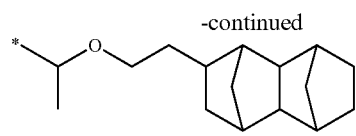

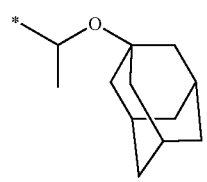

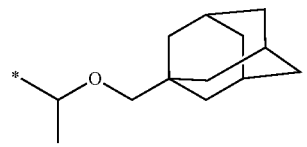

The monomer (a1) is preferably a compound having an acid-labile group and a carbon-carbon double bond, and is more preferably a (meth)acrylate compound having an acid-labile group.

Such (meth)acrylate compound preferably has a C5-C20 alicyclic hydrocarbon group. When the photoresist composition has a resin which has a structural unit with a bulky structure such as a saturated alicyclic hydrocarbon group, the photoresist composition can provide a photoresist pattern with excellent resolution.

Specific examples of the structural unit derived from the (meth)acrylate compound having a group of formula (1) include those represented by the formulae (a1-0), (a1-1) and (a1-2). The structural units represented by the formulae (a1-0), (a1-1) and (a1-2) are sometimes referred to as "structural unit (a1-0)", "structural unit (a1-1)" and "structural unit (a1-2)", respectively. The monomers from which the structural unit (a1-0), (a1-1) and (a1-2) are derived are sometimes referred to as "monomer (a1-0)", "monomer (a1-1)" and "monomer (a1-2)", respectively.

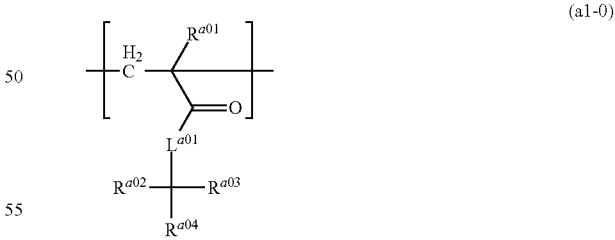

(a1-0)

In formula (a1-1), $L^{a01}$ each independently represents an oxygen atom or *—O—$(CH_2)_{k01}$—CO—O— in which * represents a binding site to —CO—, and k01 represents an integer of 1 to 7;

$R^{a01}$ each independently represent a hydrogen atom or a methyl group;

$R^{a02}$, $R^{a03}$ and $R^{a04}$ each independently represent a C1-C8 alkyl group, a C3-C18 alicyclic hydrocarbon group, or a combination of them.

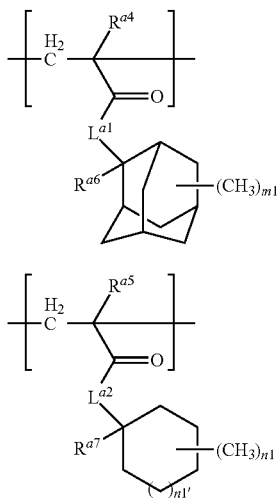

(a1-1)

(a1-2)

wherein $L^{a1}$ and $L^{a2}$ each independently represents an oxygen atom or *—O—$(CH_2)_{k1}$—CO—O— in which * represents a binding site to —CO—, and k1 represents an integer of 1 to 7;

$R^{a4}$ and $R^{a5}$ each independently represent a hydrogen atom or a methyl group;

$R^{a6}$ and $R^{a7}$ each independently represent a C1-C8 alkyl group, a C3-C18 alicyclic hydrocarbon group, or a combination of them;

"m1" represents an integer of 0 to 14; "n1" represents an integer of 0 to 10; and "n1'" represents 0 to 3.

$L^{a01}$ is preferably an oxygen atom or *—O—$(CH_2)_{f01}$—CO—O— in which * represents a binding site to —CO—, and "f01" represents an integer of 1 to 4, and is more preferably an oxygen atom.

"f01" represents preferably an integer of 1 to 4, more preferably 1.

Examples of the alkyl group, the alicyclic hydrocarbon group and the combination of them, represented by $R^{a02}$, $R^{a03}$ and $R^{a04}$, include those same as examples of those represented by $R^{a1}$, $R^{a2}$ and $R^{a3}$.

The alkyl group represented by $R^{a02}$, $R^{a03}$ or $R^{a04}$ is preferably a C1-C6 alkyl group.

The alicyclic hydrocarbon group represented by $R^{a02}$, $R^{a03}$ or $R^{a04}$ has preferably 8 or less, and more preferably 6 or less of carbon atoms. The combination of the alkyl group and the alicyclic hydrocarbon, as a group represented by $R^{a02}$, $R^{a03}$ or $R^{a04}$, has preferably 18 or less of carbon atoms. Examples of the combination include a methylcyclohexyl group, dimethylcyclohexyl group, a methylnorbornyl group, a methyladamantyl group, a (cyclohexyl)methyl group, a methyl cyclohexylmethyl group, an adamantylmethyl group, and a norbornylmethyl group.

$R^{a02}$ and $R^{a03}$ are each preferably a C1-C6 alkyl group, more preferably a methyl group or an ethyl group.

$R^{a04}$ is preferably a C1-C6 alkyl group or a C5-C12 alicyclic hydrocarbon group, more preferably a methyl group, an ethyl group, a cyclohexyl group or an adamantyl group.

$L^{a1}$ and $L^{a2}$ are preferably an oxygen atom or *—O—$(CH_2)_{f1}$—CO—O— in which * represents a binding site to —CO—, and "f1" represents an integer of 1 to 4, and is more preferably an oxygen atom.

"f1" represents preferably an integer of 1 to 4, more preferably an integer of 1.

$R^{a4}$ and $R^{a5}$ are each preferably a methyl group.

Examples of the alkyl group, the alicyclic hydrocarbon group and the combination of them, represented by $R^{a6}$ and $R^{a7}$, include those same as examples for $R^{a1}$, $R^{a2}$ and $R^{a3}$.

The alkyl group represented by $R^{a6}$ or $R^{a7}$ is preferably a C1-C6 alkyl group.

The alicyclic hydrocarbon group represented by $R^{a6}$ or $R^{a7}$ has preferably 8 or less, more preferably 6 or less of carbon atoms.

"m1" is preferably an integer of 0 to 3, and more preferably 0 or 1. "n1" is preferably an integer of 0 to 3, and more preferably 0 or 1. "n1'" is preferably 0 or 1.

The structural unit (a1-0) is preferably one represented by any one of the following formulae, and more preferably one represented by any one of formulae (a1-0-1) to (a1-0-10).

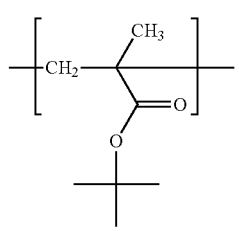

(a1-0-1)

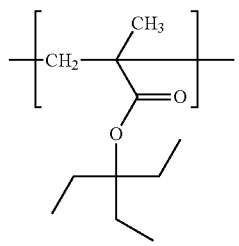

(a1-0-2)

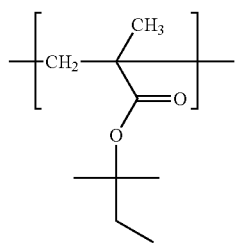

(a1-0-3)

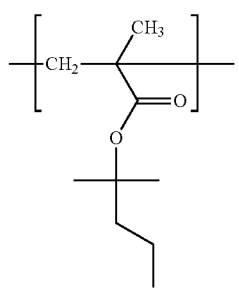

(a1-0-4)

(a1-0-5) 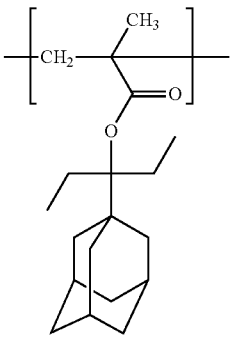

(a1-0-6) 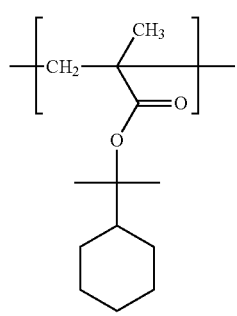

(a1-0-7) 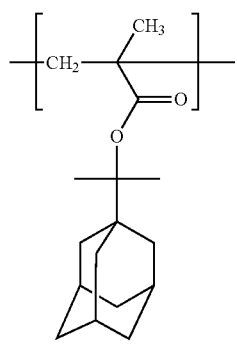

(a1-0-8) 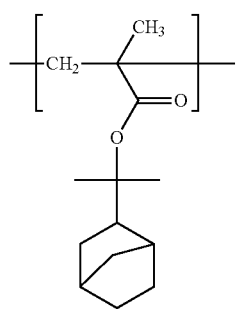

(a1-0-9) 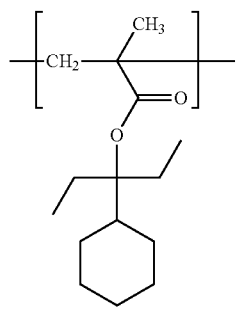

(a1-0-10) 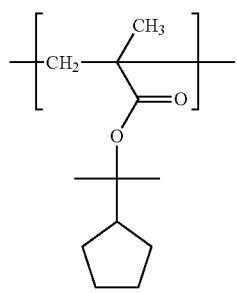

(a1-0-11) 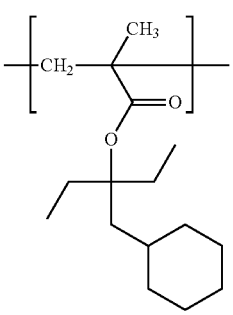

(a1-0-12) 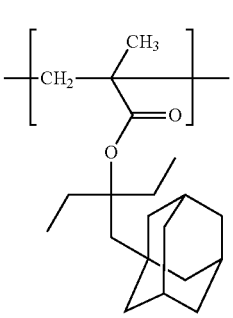

Other examples of the structural unit (a1-0) include those represented by the above-mentioned formulae in which a methyl group bonded to its main chain has been replaced by a hydrogen atom.

Examples of the monomer (a1-1) include those as recited in JP2010-204646A1. Among them, preferred are those represented by of formulae (a1-1-1) to (a1-1-8), and more preferred are those represented by of formulae (a1-1-1) to (a1-1-4).

(a1-1-1) 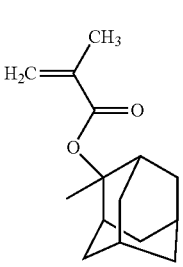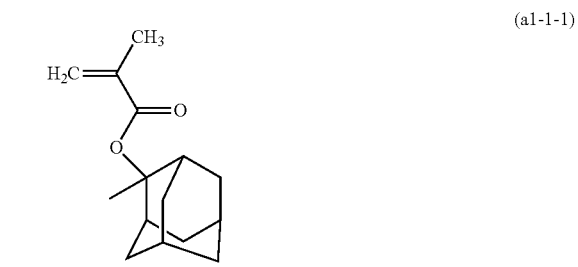

(a1-1-2) 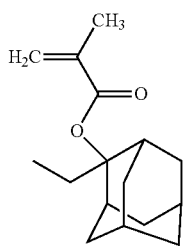

(a1-1-3) 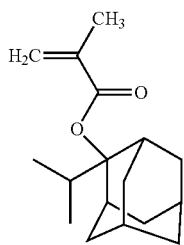

(a1-1-4) 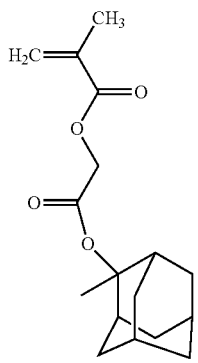

(a1-1-5) 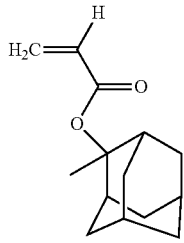

(a1-1-6) 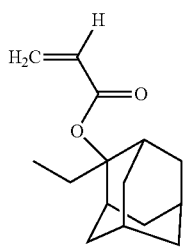

(a1-1-7) 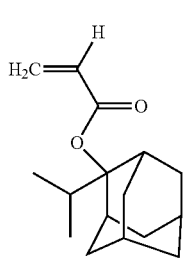

(a1-1-8) 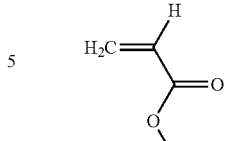

Examples of the monomer (a1-2) include 1-ethyl-cyclopentan-1-yl(meth)acrylate, 1-ethyl-cyclohexan-1-yl(meth)acrylate, 1-ethyl-cyclohept-1-yl(meth)acrylate, 1-methyl-cyclopent-1-yl(meth)acrylate, 1-methyl-cyclohex-1-yl(meth)acrylate, 1-isopropyl-cyclopent-1-yl(meth)acrylate, and 1-isopropyl-cyclohex-1-yl(meth)acrylate.

As the monomer (a1-2), preferred are those represented by formulae (a1-2-1) to (a1-2-12), more preferred are those represented by formulae (a1-2-3), (a1-2-4), (a1-2-9) and (a1-2-10), more preferred are those represented by formulae (a1-2-3) and (a1-2-9).

(a1-2-1) 

(a1-2-2) 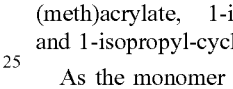

(a1-2-3) 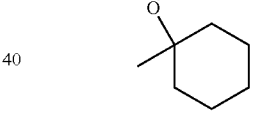

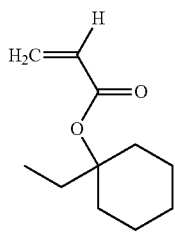
(a1-2-4)

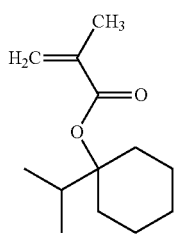
(a1-2-5)

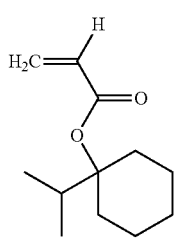
(a1-2-6)

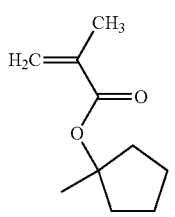
(a1-2-7)

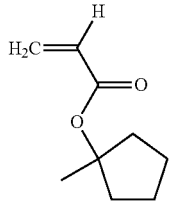
(a1-2-8)

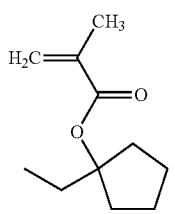
(a1-2-9)

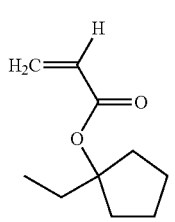
(a1-2-10)

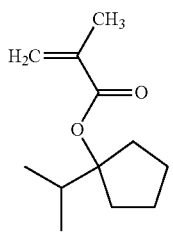
(a1-2-11)

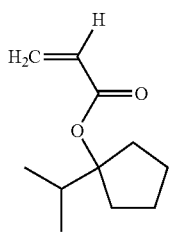
(a1-2-12)

When the resin (A) has at least one of the structural units (a1-0), (a1-1) and (a1-2), the content of the structural unit in the resin is usually 10 to 95% by mole, preferably 15 to 90% by mole, and more preferably 20 to 85% by mole based on all the structural units of the resin (A).

Examples of the structural unit (a1) having the group represented by formula (1) include a structural unit represented by formula (a1-3). The structural unit represented by formula (a1-3) is sometimes referred to as "structural unit (a1-3)". The monomer from which the structural unit (a1-3) is derived is sometimes referred to as "monomer (a1-3)".

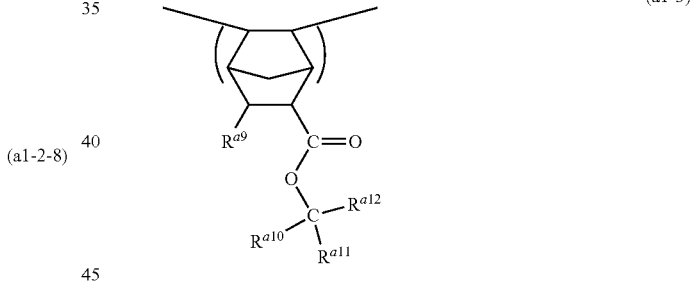
(a1-3)

In the formula, $R^{a9}$ represents a carboxy group, a cyano group, a —COOR$^{a13}$, a hydrogen atom or a C1-C3 aliphatic hydrocarbon group that may have a hydroxy group, $R^{a13}$ represents a C1-C8 aliphatic hydrocarbon group, a C3-C20 alicyclic hydrocarbon group or a group formed by combining thereof, a hydrogen atom contained in the aliphatic hydrocarbon group and the alicyclic hydrocarbon group may be replaced by a hydroxy group, a methylene group contained in the aliphatic hydrocarbon group and the alicyclic hydrocarbon group may be replaced by an oxygen atom or a carbonyl group, and $R^{a10}$, $R^{a11}$ and $R^{a12}$ each independently represent a C1-C8 alkyl group, a C3-C20 alicyclic hydrocarbon group or a group formed by combining thereof, or $R^{a10}$ and $R^{a11}$ may be bonded together with a carbon atom bonded thereto to form a C2-C20 divalent hydrocarbon group.

Here, examples of —COOR$^{a13}$ group include a group in which a carbonyl group is bonded to the alkoxy group, such as methoxycarbonyl and ethoxycarbonyl groups.

Examples of the aliphatic hydrocarbon group that may have a hydroxy group for $R^{a9}$ include methyl, ethyl, propyl, hydroxymethyl and 2-hydroxyethyl groups.

Examples of the C1-C8 aliphatic hydrocarbon group for $R^{13}$ include methyl, ethyl, propyl, isopropyl, n-butyl, sec-butyl, tert-butyl, n-pentyl, n-hexyl, n-heptyl, 2-ethylhexyl and n-octyl groups.

Examples of the C3-C20 alicyclic hydrocarbon group for $R^{a13}$ include cyclopentyl, cyclopropyl, adamantyl, adamantylmethyl, 1-(adamantyl-1-yl)-methylethyl, 2-oxo-oxolane-3-yl and 2-oxo-oxolane-4-yl groups.

Examples of the alkyl group for $R^{a10}$ to $R^{a12}$ include methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group for $R^{a10}$ and $R^{a12}$ include monocyclic groups such as a cycloalkyl group, i.e., cyclopropyl, cyclobutyl, cyclopentyl, cyclohexyl, methylcyclohexyl, dimethylcyclohexyl, cycloheptyl, cyclooctyl and cyclodecyl groups; and polycyclic groups such as decahydronaphtyl, adamantyl, 2-alkyl-2-adamantyl, 1-(adamantane-1-yl)alkane-1-yl, norbornyl, methylnorbornyl and isobornyl groups.

When $R^{a10}$ and $R^{a11}$ are bonded together with a carbon atom bonded thereto to form a divalent hydrocarbon group, examples of the group-$C(R^{a10})(R^{a11})(R^{a12})$ include the following groups.

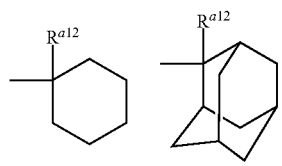

In each formula, $R^{a12}$ is as defined above.

Examples of the monomer (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantane-2-yl 5-norbornene-2-carboxylate, 2-ethyl-2-adamantane-2-yl 5-norbornene-2-carboxylate, 1-(4-methylcyclohexyl)-1-methylethyl 5-norbornene-2-carboxylate, 1-(4-hydroxycyclohexyl)-1-methylethyl 5-norbornene-2-carboxylate, 1-methyl-(4-oxo-cyclohexyl)-1-ethyl 5-norbornene-2-carboxylate, and 1-(1-adamantane-1-yl)-1-methylethyl 5-norbornene-2-carboxylate.

The resin (A) which has the structural unit (a1-3) can improve the resolution of the obtained resist composition because it has a bulky structure, and also can improve a dry-etching tolerance of the obtained photoresist composition because of incorporated a rigid norbornene ring into a main chain of the resin (A).

When the resin (A) has the structural unit (a1-3), the proportion thereof is preferably 10% by mole to 95% by mole, more preferably 15% by mole to 90% by mole, and still more preferably 20% by mole to 85% by mole, based on the all the structural units of the resin (A) (100% by mole).

Examples of the structural unit (a1) having the group represented by formula (2) include a structural unit represented by formula (a1-4). The structural unit is sometimes referred to as "structural unit (a1-4)".

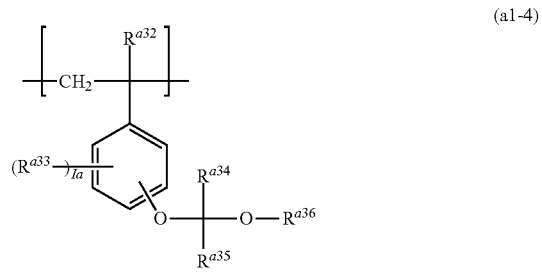

In the formula, $R^{a32}$ represents a hydrogen atom, a halogen atom or a C1-C6 alkyl group that may have a halogen atom, $R^{a33}$ in each occurrence independently represent a halogen atom, a hydroxy group, a C1-C6 alkyl group, a C1-C6 alkoxy group, a C2-C4 acyl group, a C2-C4 acyloxy group, an acryloyloxy group or methacryloyloxy group, "la" represents an integer of 0 to 4, $R^{a34}$ and $R^{a35}$ each independently represent a hydrogen atom or a C1-C12 hydrocarbon group, and $R^{a36}$ represents a C1-C20 hydrocarbon group, or $R^{a35}$ and $R^{a36}$ may be bonded together with a C—O bonded thereto to form a divalent C3-C20 heterocyclic group, and a methylene group contained in the hydrocarbon group or the divalent heterocyclic group may be replaced by an oxygen atom or a sulfur atom.

Examples of the alkyl group of $R^{a32}$ and $R^{a33}$ include methyl, ethyl, propyl, isopropyl, butyl, pentyl and hexyl groups. The alkyl group is preferably a C1-C4 alkyl group, and more preferably a methyl group or an ethyl group, and still more preferably a methyl group.

Examples of the halogen atom of $R^{a32}$ and $R^{a33}$ include a fluorine, chlorine, bromine and iodine atoms.

Examples of the alkyl group that may have a halogen atom include trifluoromethyl, difluoromethyl, methyl, perfluoroethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, n-pentyl, n-hexyl and n-perfluorohexyl groups.

Examples of an alkoxy group include methoxy, ethoxy, propoxy, butoxy, pentyloxy and hexyloxy groups. The alkoxy group is preferably a C1-C4 alkoxy group, more preferably a methoxy group or an ethoxy group, and still more preferably a methoxy group.

Examples of the acyl group include acetyl, propionyl and butyryl groups.

Examples of the acyloxy group include acetyloxy, propionyloxy and butyryloxy groups.

Examples of the hydrocarbon group for $R^{a34}$ and $R^{a35}$ are the same examples as described in $R^{a1'}$ to $R^{a2'}$ in the formula (2).

Examples of hydrocarbon group for $R^{a36}$ include a C1-C18 alkyl group, a C3-C18 alicyclic hydrocarbon group, a C6-C18 aromatic hydrocarbon group or a group formed by combining thereof.

In the formula (a1-4), $R^{a32}$ is preferably a hydrogen atom. $R^{a33}$ is preferably a C1-C4 alkoxy group, more preferably a methoxy group or an ethoxy group, and still more preferably a methoxy group.

"la" is preferably 0 or 1, and more preferably 0.

$R^{a34}$ is preferably a hydrogen atom.

$R^{a35}$ is preferably a C1-C12 hydrocarbon group, and more preferably a methyl group or an ethyl group.

The hydrocarbon group for $R^{a36}$ is preferably a C1-C18 alkyl group, a C3-C18 alicyclic hydrocarbon group, a C6-C18 aromatic hydrocarbon group or a combination thereof, and more preferably a C1-C18 alkyl group, a C3-C18 alicyclic hydrocarbon group or a C7-C18 aralkyl group. The alkyl group and the alicyclic hydrocarbon group for $R^{a36}$ are preferably unsubstituted. When the aromatic hydrocarbon group of $R^{a36}$ has a substituent, the substituent is preferably a C6-C10 aryloxy group.

Examples of the monomer from which the structural unit (a1-4) is derived include monomers described in JP2010-204646A1. Among these, the monomers are preferably the following monomers represented by formula (a1-4-1) to formula (a1-4-8), and more preferably monomers represented by formula (a1-4-1) to formula (a1-4-5), and formula (a1-4-8).

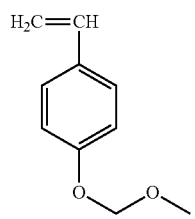
(a1-4-1)

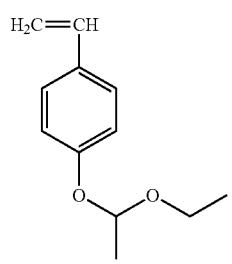
(a1-4-2)

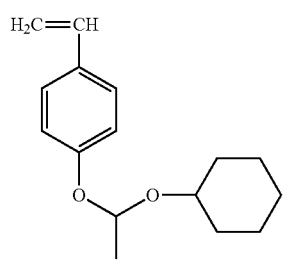
(a1-4-3)

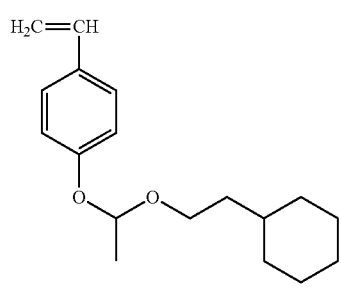
(a1-4-4)

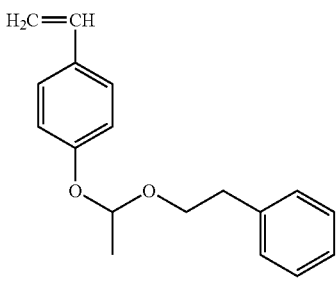
(a1-4-5)

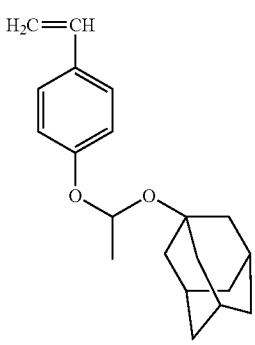
(a1-4-6)

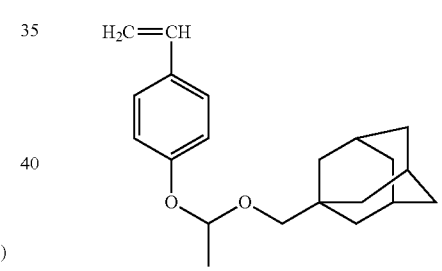
(a1-4-7)

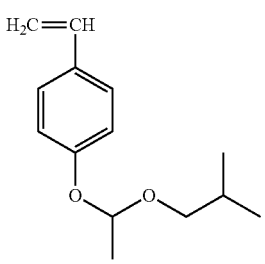
(a1-4-8)

When the resin (A) has the structural unit (a1-4), the proportion thereof is preferably 10% by mole to 95% by mole, more preferably 15% by mole to 90% by mole, and still more preferably 20% by mole to 85% by mole, based on the all the structural units of the resin (A) (100% by mole).

Another example of the structural unit (a1) includes a structural unit represented by the formula (a1-5).

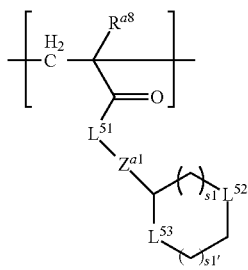

(a1-5)

In the formula (a1-5), $R^{a8}$ represents a hydrogen atom, a halogen atom or a C1-C6 alkyl group that may have a halogen atom, $Z^{a1}$ represent a single bond or *—$(CH_2)_{h3}$—CO-$L^{54}$-, where h3 represents an integer of 1 to 4, * represents a binding site to $L^{51}$, and $L^{54}$ represents —O— or —S—, $L^{51}$, $L^{52}$ and $L^{53}$ each independently represent —O— or —S—, "s1" represents an integer of 1 to 3, and "s1'" represents an integer of 0 to 3.

The structural unit represented by the formula (a1-5) is sometimes referred to as "structural unit (a1-5)".

$R^{a8}$ is preferably a hydrogen atom, a methyl group or a trifluoromethyl group.

$L^{51}$ is preferably —O—.

$L^{52}$ and $L^{53}$ are independently preferably —O— or —S—, and more preferably one is —O— and the other is —S—.

"s1" is preferably 1.

"s1'" is preferably an integer of 0 to 2.

$Z^{a1}$ is preferably a single bond or *—$CH_2$—CO—O— where * represents a binding site to $L^{51}$.

Examples of the monomer from which the structural unit (a1-5) is derived include the monomers described in JP2010-61117A1. Among these, the monomers are preferably the following monomers represented by formula (a1-5-1) to formula (a1-5-4), and more preferably monomers represented by formula (a1-5-1) and formula (a1-5-2)

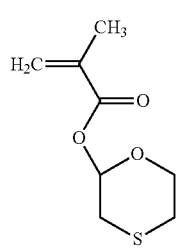

(a1-5-1)

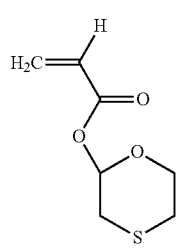

(a1-5-2)

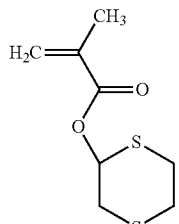

(a1-5-3)

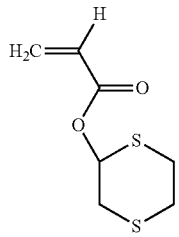

(a1-5-4)

When the resin (A) has a structural unit (a1-5), the content of the structural unit is usually 1 to 50% by mole, preferably 3 to 45% by mole and more preferably 5 to 40% by mole based on all the structural units of the resin.

The resin (A) has, as the structural unit (a1), preferably at least one, more preferably two or more structural units selected from the structural unit (a1-0), the structural unit (a1-1), the structural unit (a1-2) and the structural unit (a1-5), still more preferably a combination of the structural unit (a1-1) and the structural unit (a1-2), a combination of the structural unit (a1-1) and the structural unit (a1-5), a combination of the structural unit (a1-1) and the structural unit (a1-0), a combination of the structural unit (a1-2) and the structural unit (a1-0), a combination of the structural unit (a1-5) and the structural unit (a1-0), a combination of the structural unit (a1-0), the structural unit (a1-1) and the structural unit (a1-2), a combination of the structural unit (a1-0), the structural unit (a1-1) and the structural unit (a1-5), and further still preferably a combination of the structural unit (a1-1) and the structural unit (a1-2), and a combination of the structural unit (a1-1) and the structural unit (a1-5).

Examples of structural units other than the structural unit (a1) include a structural unit having no acid-labile group which structural unit is referred to as "structural unit (s)".

Examples of the structural unit (s) include a structural unit having no acid-labile group but a hydroxy group or a lactone ring.

The structural unit having no acid-labile group but a hydroxy group and the structural unit having no acid-labile group but a lactone ring are sometimes referred to as "structural unit (a2)" and "structural unit (a3)", respectively.

By employing the resin which contains the structural unit (a2) or (a3) to the photoresist composition of the disclosure, the photoresist composition can provide a photoresist pattern with improved resolution and adhesiveness with its substrate.

The structural unit (a2) may have a phenolic-hydroxy group or an alcoholic hydroxy group.

When KrF excimer laser (wavelength: 248 nm) lithography system, or a high energy laser such as electron beam and extreme ultraviolet is used as an exposure system, preferred is a resin which has a structural unit (a2) having a phenolic-hydroxy group.

When ArF excimer laser (wavelength: 193 nm) is used as an exposure system, preferred is a resin which has the structural unit (a2) having an alcoholic hydroxy group, and more preferred is a resin which has the structural unit represented by formula (a2-1) described later.

The resin (A) can have one or more kinds of the structural units (a2).

Preferred examples of the structural unit (a2) include a structural unit represented by the formula (a2-0), which is sometimes referred to as "structural unit (a2-0)":

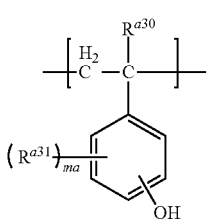
(a2-0)

wherein $R^{a30}$ represents a hydrogen atom, a halogen atom or a C1-C6 alkyl group that may have a halogen atom, $R^{a31}$ in each occurrence independently represents a halogen atom, a hydroxy group, a C1-C6 alkyl group, a C1-C6 alkoxy group, a C2-C4 acyl group, a C2-C4 acyloxy group, an acryloyloxy group or methacryloyloxy group, and "ma" represents an integer 0 to 4.

Examples of the alkyl group include methyl, ethyl, propyl, butyl, n-pentyl and n-hexyl groups.

Examples of the halogen atom include a chlorine atom, a fluorine atom and bromine atom.

Examples of the C1-C6 alkyl group that may have a halogen atom for $R^{a30}$ include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, n-pentyl, n-hexyl and n-perfluorohexyl groups.

$R^{a30}$ is preferably a hydrogen atom or a C1-C4 alkyl group, and more preferably a hydrogen atom, a methyl group or an ethyl group, and still more preferably a hydrogen atom or a methyl group.

Examples of the alkoxy group for $R^{a31}$ include methoxy, ethoxy, propoxy, butoxy, pentyloxy, and hexyloxy groups. $R^{a31}$ is preferably a C1-C4 alkoxy group, more preferably a methoxy group or an ethoxy group, and still more preferably a methoxy group.

Examples of the acyl group include acetyl, propionyl and butyryl groups.

Examples of the acyloxy group include acetyloxy, propionyloxy and butyryloxy groups.

"ma" is preferably 0, 1 or 2, more preferably 0 or 1, still more preferably 0.

Examples of a monomer from which the structural unit (a2-0) is derived include monomers described in JP2010-204634A1.

The structural unit (a2-0) is preferably any one of the structural units represented below, more preferably any one of those represented by formulae (a2-0-1) and (a2-0-2):

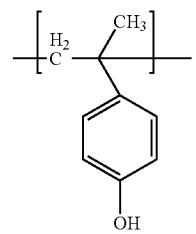
(a2-0-1)

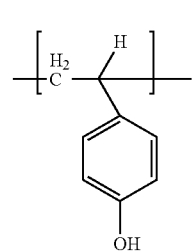
(a2-0-2)

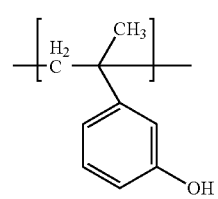
(a2-0-3)

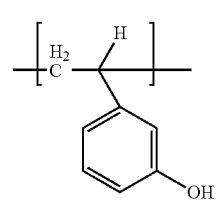
(a2-0-4)

The resin (A) which further has the structural units (a2-0) can be produced, for example, by polymerizing a monomer where its phenolic hydroxy group has been protected with a suitable protecting group, followed by deprotection. The deprotection is carried in such a manner that an acid-labile group in the structural unit (a1) is not significantly impaired. Examples of the protecting group for a phenolic hydroxy group include an acetyl group.

When the resin (A) further has the structural unit (a2) having a phenolic-hydroxy group, the proportion thereof is preferably 5 to 95% by mole, more preferably 10 to 80% by mole, and still more preferably 15 to 80% by mole, based on all the structural units of the resin (A).

Preferred examples of the structural unit (a2) having an alcoholic hydroxy group include a structural unit represented by the formula (a2-1):

(a2-1)

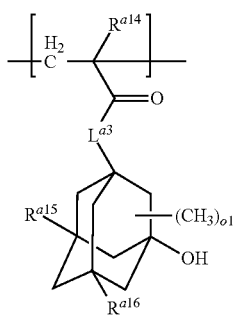

wherein $R^{a14}$ represents a hydrogen atom or a methyl group, $R^{a15}$ and $R^{a16}$ each independently represent a hydrogen atom, a methyl group or a hydroxy group, $L^{a3}$ represents an oxygen atom or *—O—$(CH_2)_{k2}$—CO—O— in which * represents a binding site to —CO—, and k2 represents an integer of 1 to 7, and o1 represents an integer of 0 to 10.

In the formula (a2-1), $L^{a3}$ is preferably an oxygen atom or *—O—$(CH_2)_{f2}$—CO—O— in which * represents a binding site to —CO—, and f2 represents an integer of 1 to 4, is more preferably an oxygen atom and *—O—$CH_2$—CO—O—, and is still more preferably an oxygen atom.

$R^{14}$ is preferably a methyl group.

$R^{a15}$ is preferably a hydrogen atom.

$R^{a16}$ is preferably a hydrogen atom or a hydroxy group.

o1 is preferably 0, 1, 2 or 3 and is more preferably 0 or 1.

Examples of the monomer from which the structural unit represented by the formula (a2-1) is derived include those mentioned in JP2010-204646A1, preferably those represented by formulae (a2-1-1), (a2-1-2), (a2-1-3), (a2-1-4), (a2-1-5) and (a2-1-6), and more preferably those represented by formulae (a2-1-1), (a2-1-2), (a2-1-3) and (a2-1-4), still more preferably those represented by formulae (a2-1-1) and (a2-1-3).

(a2-1-1)

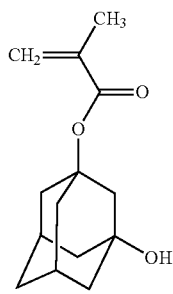

(a2-1-2)

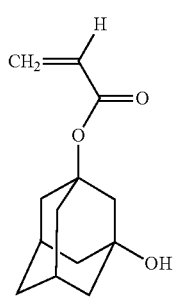

(a2-1-3)

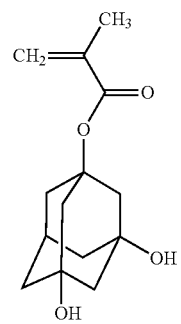

(a2-1-4)

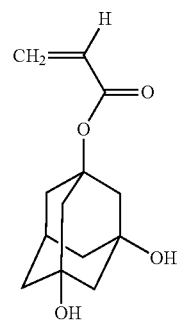

(a2-1-5)

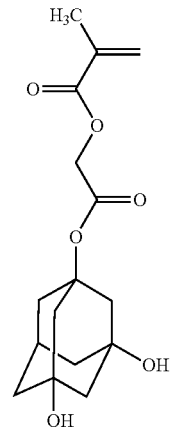

(a2-1-6)

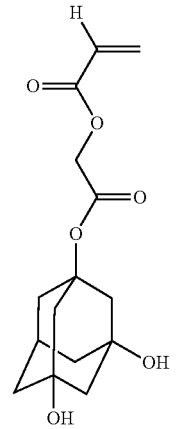

When the resin (A) further has the structural unit represented by the formula (a2-1), the content of the structural unit represented by the formula (a2-1) is usually 1 to 45% by mole and preferably 1 to 40% by mole, more preferably 1 to 35% by mole, still more preferably 2 to 20% by mole, based on all the structural units of the resin (A).

In the structural unit (a3), examples of the lactone ring include amonocyclic lactone ring such as β-propiolactone ring, γ-butyrolactone ring and δ-valerolactone ring, and a condensed ring formed from a monocyclic lactone ring and the other ring. Among them, preferred are γ-butyrolactone ring and a condensed lactone ring formed from γ-butyrolactone ring and another ring.

Preferable examples of the structural unit (a3) include those represented by the formulae (a3-1), (a3-2), (a3-3) and (a3-4):

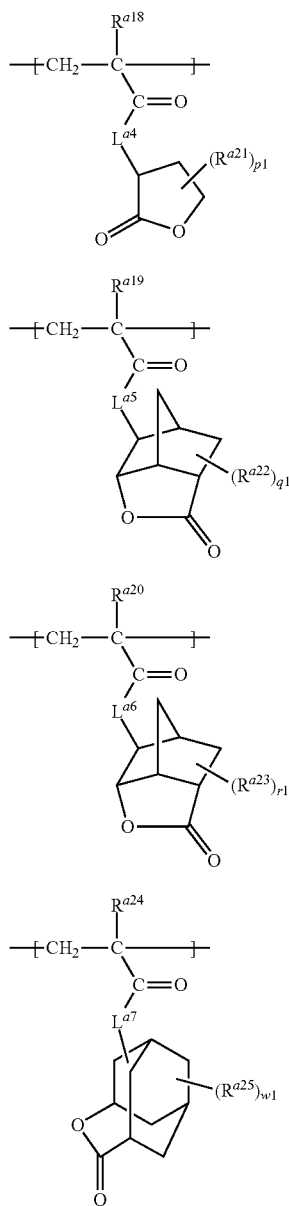

wherein $L^{a4}$, $L^{a5}$ and $L^{a6}$ each independently represent *—O— or *—O—(CH$_2$)$_{k3}$—CO—O— in which * represents a binding site to —CO— and k3 represents an integer of 1 to 7, $L^{a7}$ represents a single bond, *-$L^{a8}$-O—, -$L^{a8}$-CO—O—, *-$L^{a8}$-CO—O-$L^{a9}$-CO—O—, or *-$L^{a8}$-O—CO-$L^{a9}$-O—; * represents a binding site to a carbonyl group, $L^{a8}$ and $L^{a9}$ each represent a C1-C6 alkanediyl group, $R^{a18}$, $R^{a19}$ and $R^{a20}$ each independently represent a hydrogen atom or a methyl group, $R^{a21}$ represents a C1-C4 aliphatic hydrocarbon group, $R^{a22}$, $R^{a23}$ and $R^{a25}$ are independently in each occurrence a carboxyl group, a cyano group or a C1-C4 aliphatic hydrocarbon group, $R^{a24}$ represents a hydrogen atom, a halogen atom or a C1-C6 alkyl group optionally having a halogen atom, p1 represents an integer of 0 to 5, g1 and r1 each independently represent an integer of 0 to 3, and w1 represents an integer of 0 to 8.

Examples of the aliphatic hydrocarbon group for $R^{a21}$, $R^{a22}$, $R^{a23}$ and $R^{a25}$ include an alkyl group such as methyl, ethyl, n-propyl, isopropyl, n-butyl, sec-butyl and tert-butyl groups.

Examples of the alkanediyl group of $L^{a8}$ and $L^{a9}$ include methylene, ethylene, propane-1,3-diyl, propane-1,2-diyl, butane-1,4-diyl, pentane-1,5-diyl, hexane-1,6-diyl, butane-1,3-diyl, 2-methylpropane-1,3-diyl, 2-methylpropane-1,2-diyl, pentane-1,4-diyl and 2-methylbutane-1,4-diyl groups.

$L^{a4}$, $L^{a5}$ and $L^{a6}$ each independently represent preferably —O— or *—O—(CH$_2$)$_{d1}$—CO—O— in which * represents a binding site to —CO— and d1 represents an integer of 1 to 4, and more preferably —O— and *—O—CH$_2$—CO—O—, and still more preferably —O—.

Preferably, $R^{a18}$, $R^{a19}$ and $R^{a20}$ are independently in each occurrence a methyl group.

Preferably, $R^{a22}$ and $R^{a23}$ are independently in each occurrence a carboxyl group, a cyano group or a methyl group.

p1, q1, r1 and w1 are independently in each occurrence preferably an integer of 0 to 2, and more preferably 0 or 1.

Examples of the halogen atom for $R^{a24}$ include fluorine, chlorine, bromine and iodine atoms.

Examples of the alkyl group for $R^{a24}$ include methyl, ethyl, n-propyl, isopropyl, n-butyl, sec-butyl, tert-butyl, n-pentyl and n-hexyl groups. The alkyl group is preferably a C1-C4 alkyl group, more preferably a methyl group or an ethyl group.

Examples of the alkyl group having a halogen atom for $R^{a24}$ include trifluoromethyl, perfluoroethyl, perfluoropropyl, perfluoro-isopropyl, perfluorobutyl, perfluoro-sec-butyl, perfluoro-tert-butyl, perfluoropentyl, perfluorohexyl, trichloromethyl, tribromomethyl and triiodomethyl groups.

$R^{a24}$ is preferably a hydrogen atom or a C1-C4 alkyl group, more preferably a hydrogen atom, a methyl group or an ethyl group, and still more preferably a hydrogen atom or a methyl group.

$L^{a7}$ represents preferably a single bond or *-$L^{a8}$-CO—O—, and more preferably a single bond, *—CH$_2$—CO—O— or *—C$_2$H$_4$—CO—O—.

Examples of the monomers from which the structural unit (a3) is derived include those mentioned in JP2010-204646A1, JP2010-122294A1, and JP2010-41274A1. Examples of monomers from which the structural unit (a3) is derived include preferably those represented by the formulae (a3-1-1), (a3-1-2), (a3-1-3) and (a3-1-4), the formulae (a3-2-1), (a3-2-2), (a3-2-3) and (a3-2-4), the formulae (a3-3-1), (a3-3-2), (a3-3-3) and (a3-3-4), and the formulae (a3-4-1) to (a3-4-12), more preferably those represented by the formulae (a3-1-1), (a3-1-2), (a3-2-3), (a3-2-4), (a3-4-1) to (a3-4-12), still more preferably those represented by the formulae (a3-4-1) to (a3-4-12), and further more preferably those represented by the formulae (a3-4-1) to (a3-4-6).

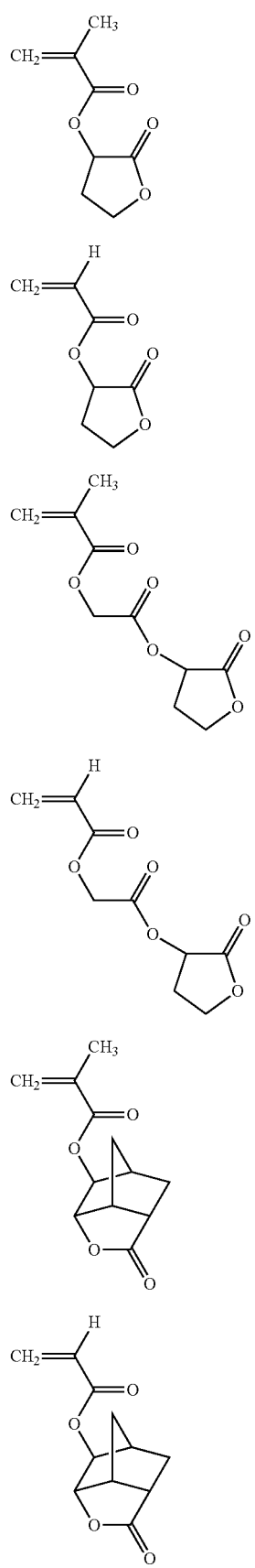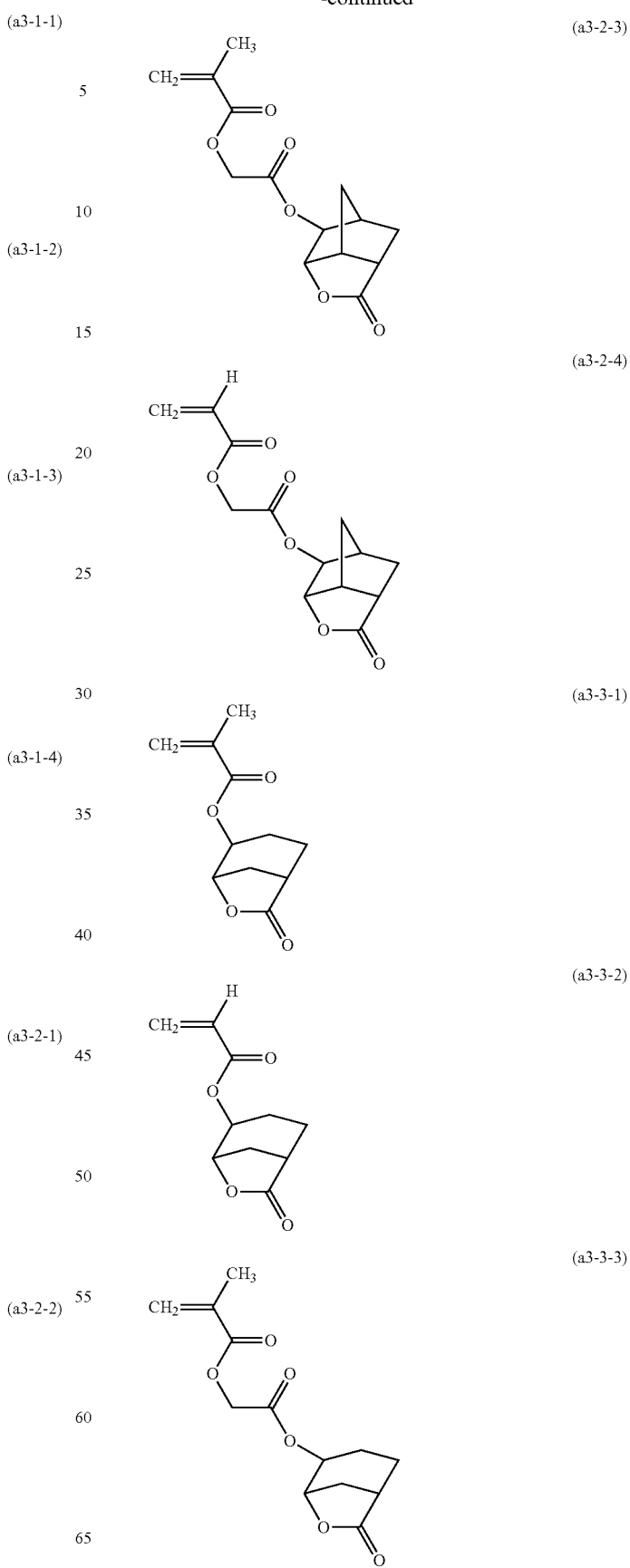

(a3-3-4)
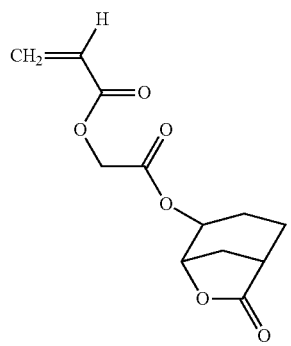
(a3-4-1)
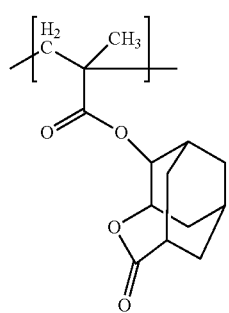
(a3-4-2)
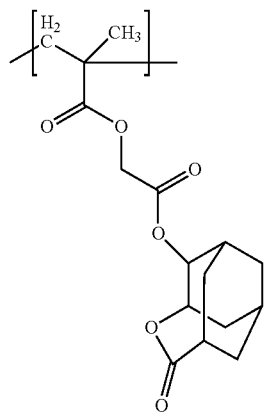
(a3-4-3)
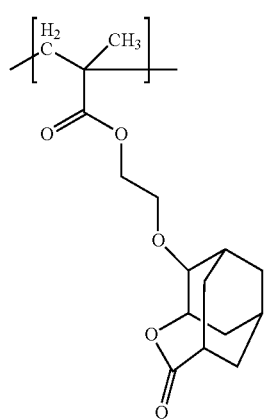
(a3-4-4)
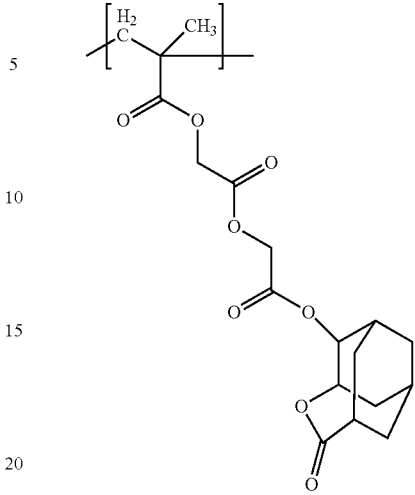
(a3-4-5)
(a3-4-6)

(a3-4-7) 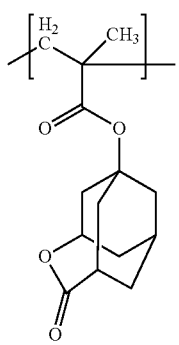
(a3-4-10) 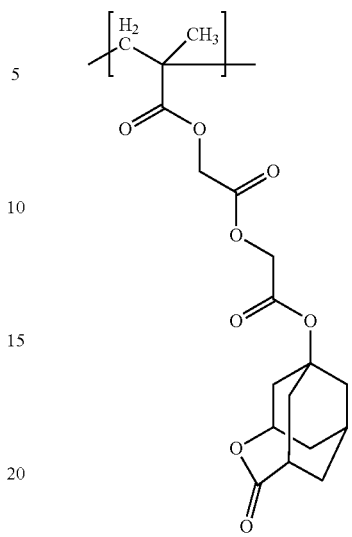
(a3-4-8)
(a3-4-11) 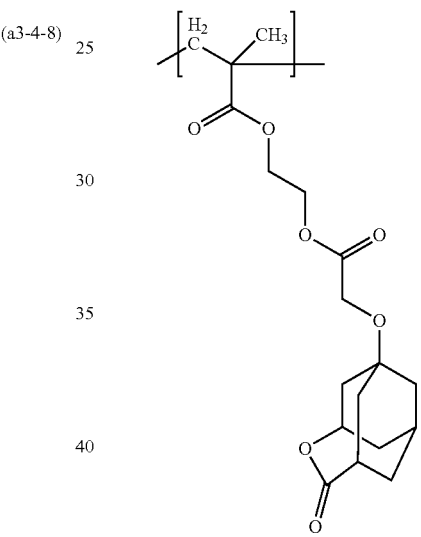
(a3-4-9) 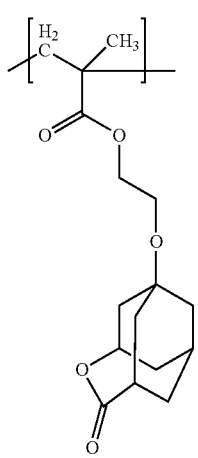
(a3-4-12) 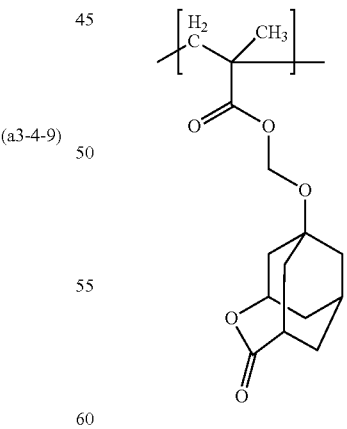
Examples of the structural unit (a3) further include those represented by formulae (a3-4-1) to (a3-4-12) in which a methyl group has been replaced by a hydrogen atom.
When the resin (A) has the structural unit (a3), the total content of the structural unit (a3) is usually 5 to 70% by mole, preferably 10 to 65% by mole, and more preferably 10 to 60% by mole, based on all the structural units of the resin (A).

When the resin (A) has the structural unit (a3-1), (a3-2), (a3-3) or (a3-4), each content of them is usually 5 to 60% by mole, preferably 5 to 50% by mole, and more preferably 10 to 50% by mole, based on all the structural units of the resin (A).

The resin (A) may further have the structural unit (a4) and/or (a5) as described above.

When the resin (A) has the structural unit (a4), the content of that is usually 1 to 20% by mole, preferably 2 to 15% by mole, and more preferably 3 to 10% by mole, based on all the structural units of the resin (A).

When the resin (A) has the structural unit (a5), the content of that is usually 1 to 30% by mole, preferably 2 to 20% by mole, and more preferably 3 to 15% by mole, based on all the structural units of the resin (A).

The resin (A) is preferably a resin which consists of the structural unit (a1) and the structural unit (s).

In the resin (A), the structural unit (a1) is preferably one selected from the structural units represented by formulae (a1-0), (a1-1), (a1-2) and (a1-5), more preferably one selected from the structural units represented by formulae (a1-1) and (a1-2). The structural unit represented by formula (a1-2) has preferably a cyclohexyl group or a cyclopentyl group.

In the resin (A), the structural unit (s) is preferably one selected from the structural units (a2) and (a3).

The structural unit (a2) is preferably one represented by formula (a2-1).

For the resin (A), the structural unit (a3) has preferably β-propiolactone ring, a fused ring having γ-butyrolactone ring or an adamantanelactone ring.

When the resin (A) has a structural unit derived from a monomer having an adamantyl group, preferably the structural unit represented by formula (a1-1), the content of the structural unit is preferably 15% or more by mole based on all of the structural units having an acid-labile group. When the photoresist composition has adamantane ring-containing structural units in larger amount, the photoresist pattern obtained therefrom can have more improved resistance to dry-etching.

The resin (A) can be produced by polymerizing a monomer (a1) optionally with a compound from which a structural unit (s) is derived in a manner of radical polymerization or a known polymerization method.

The weight-average molecular weight of the resin (A) is usually 2,000 or more, preferably 2,500 or more, and more preferably 3,000 or more, and usually 50,000 or less, preferably 30,000 or less, more preferably 15,000 or less.

The weight-average molecular weight can be measured with gel permeation chromatography (standard: polyethylene). The detailed method of measurement is described in Examples of the present specification.

The content of the resin (X) is preferably 1 weight parts or more, more preferably 2 weight parts or more, and still more preferably 3 weight parts or more, relative to 100 parts of Resin (A), and the content is preferably 60 weight parts or less, more preferably 50 weight parts or less, and further more preferably 30 weight parts or less, relative to 100 parts of Resin (A).

The total content of all of the resins in the photoresist composition is usually 80% by mass or more, and usually 99% by mass or less based on sum of the solid components.

In this specification, "solid component" means components other than solvent in the photoresist composition. The amount can be measured with a known analysis equipment such as gas or liquid chromatography.

The photoresist composition of the disclosure may further contain a resin other than the resins (A) and (X). The resin other than the resins (A) and (X) is any resin which has neither structural unit (I) nor structural unit (a1), examples of which include a resin consisting of the structural units (s).

The resin other than the resins (A) and (X) is preferably a resin having a structural unit (a4) which resin is sometimes referred to as "resin (Y)". In the resin (Y), the content of the structural unit (a4) is preferably 40% by mole or more, more preferably 45% by mole or more, still more preferably 50% by mole or more, based on all the structural units of the resin.

The resin (Y) may have a structural unit (a2), (a3) or (a5) or another known structural unit having no acid-labile group except for structural units (I) and (a4).

The resin (Y) has usually 6000 or more of the weight-average molecular weight, preferably 7000 or more of the weight-average molecular weight, still more preferably 8000 or more of the weight-average molecular weight.

The resin (Y) usually has 80,000 or less of the weight-average molecular weight, preferably has 60,000 or less of the weight-average molecular weight.

The weight-average molecular weight can be measured with known methods such as liquid chromatography or gas chromatography.

The resin (Y) can be produced according to known polymerization methods such as radical polymerization, using monomers corresponding to the structural units as mentioned above.

The content of the resin (Y) is preferably 1 to 60 weight parts, more preferably 3 to 50 weight parts, and still more preferably 5 to 40 weight parts, further more preferably 7 to 30 weight parts, relative to 100 parts of Resin (A).

The photoresist composition contains an acid generator. There is no limitation of the acid generator for the photoresist composition, examples of which include those known in the art.

The acid generator is a compound which can be decomposed by light or radiation to generate an acid. The acid generators may be either ionic or non-ionic one. The acid generator can be used singly or in combination of two or more of them.

The non-ionic acid generator includes organic halide, sulfonate esters (e.g., 2-nitrobenzylester, aromatic sulfonate, oxime sulfonate, N-sulfonyloxyimide, sulfonyl oxyketone, diazonaphthoquinone 4-sulfonate) and sulfone (e.g., disulfone, ketosulfone, sulfonyldiazomethane). The ionic acid generator includes an onium salt comprising an onium cation (e.g., a diazonium salt, a phosphonium salt, a sulfonium salt, an iodonium salt). Anions of the onium salts include a sulfonic acid anion, a sulfonylimide anion and a sulfonylmethide anion.

The acid generator includes compounds which generate an acid upon radiation, which are described in JP63-26653A1, JP55-164824A1, JP62-69263A1, JP63-146038A1, JP63-163452A1, JP62-153853A1, JP63-146029A1, U.S. Pat. No. 3,779,778, U.S. Pat. No. 3,849,137, German patent No. 3914407 and European patent No. 126712.

The acid generator is preferably a fluorine-containing acid generator, more preferably a salt represented by formula (B1):

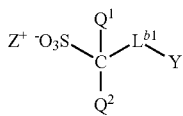

(B1)

wherein $Q^1$ and $Q^2$ each independently represent a fluorine atom or a C1-C6 perfluoroalkyl group,
$L^{b1}$ represents a single bond or a C1-C24 divalent saturated hydrocarbon group where a methylene group can be replaced by an oxygen atom or a carbonyl group and where a hydrogen atom can be replaced by an fluorine atom or a hydroxy group,
Y represents a methyl group where a hydrogen atom can be replaced by a substituent, or a C3-C18 alicyclic hydrocarbon group where a methylene group can be replaced by an oxygen atom, a sulfonyl group or a carbonyl group and where a hydrogen atom can be replaced by a substituent, and $Z^+$ represents an organic cation.

Examples of the perfluoroalkyl group represented by $Q^1$ and $Q^2$ include a trifluoromethyl group, a pentafluoroethyl group, a heptafluoropropyl group, a nonafluorobutyl group, an undecafluoropentyl group and a tridecafluorohexyl group. It is preferred that $Q^1$ and $Q^2$ each independently represent a fluorine atom or a trifluoromethyl group, and it is more preferred that $Q^1$ and $Q^2$ are fluorine atoms.

Examples of the divalent saturated hydrocarbon group represented by $L^{b1}$ include linear alkanediyl groups, branched chain alkanediyl groups, a monocyclic divalent alicyclic hydrocarbon group, a polycyclic divalent alicyclic hydrocarbon group and combinations of them.

Specific examples of them include
linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group;
branched chain alkanediyl groups including a group formed by attaching a side chain to a linear alkanediyl group, such as a butan-1,3-diyl group, a 2-methylpropane-1,3-diyl group, a 2-methylpropane-1,2-diyl group, a pentane-1,4-diyl group, and a 2-methylbutane-1,4-diyl group; a monocyclic divalent alicyclic hydrocarbon group such as a cyclobutan-1,3-diyl group, cyclopentane-1,3-diyl group, a cyclohexane-1,2-diyl group, a 1-methylcyclohexane-1,2-diyl group, cyclohexane-1,4-diyl group, cyclooctane-1,2-diyl group, and a cyclooctane-1,5-diyl group; and
a polycyclic divalent alicyclic hydrocarbon group such as a norbornane-2,3-diyl group, norbornane-1,4-diyl group, a norbornane-2,5-diyl group, an adamantane-1,2-diyl group, an adamantane-1,5-diyl group and an adamantane-1,6-diyl group.

When $L^{b1}$ represents a divalent saturated hydrocarbon group in which a methylene group has been replaced by an oxygen atom or a carbonyl group, examples of $L^{b1}$ include the moiety represented by any one of formulae (b1-1) to (b1-3) as follow;

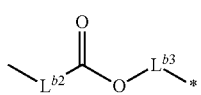

(b1-1)

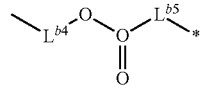

(b1-2)

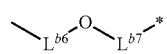

(b1-3)

wherein $L^{b2}$ represents a single bond or a C1-C22 divalent saturated hydrocarbon group in which a hydrogen atom can be replaced by a fluorine atom, and
$L^{b3}$ represents a single bond or a C1-C22 divalent saturated hydrocarbon group in which a hydrogen atom can be replaced by a fluorine atom or a hydroxyl group and in which a methylene group can be replaced by an oxygen atom or a carbonyl group, provided that the total number of the carbon atoms in $L^{b2}$ and $L^{b3}$ is up to 22;
$L^{b4}$ represents a single bond or a C1-C22 divalent saturated hydrocarbon group in which a hydrogen atom can be replaced by a fluorine atom, and $L^{b5}$ represents a single bond or a C1-C22 divalent saturated hydrocarbon group in which a hydrogen atom can be replaced by a fluorine atom or a hydroxyl group and in which a methylene group can be replaced by an oxygen atom or a carbonyl group, provided that the total number of the carbon atoms in $L^{b4}$ and $L^{b5}$ is up to 22;
$L^{b6}$ represents a C1-C15 divalent saturated hydrocarbon group in which a hydrogen atom can be replaced by a fluorine atom or a hydroxyl group, and $L^{b7}$ represents a single bond or a C1-C15 divalent saturated hydrocarbon group in which a hydrogen atom can be replaced by a fluorine atom or a hydroxyl group and in which a methylene group can be replaced by an oxygen atom or a carbonyl group, provided that the total number of the carbon atoms in $L^{b6}$ and $L^{b7}$ is up to 23; and * represents a binding site to Y.

In formula (b1-1) to formula (b1-3), when a methylene group has been replaced by an oxygen atom or a carbonyl group, the carbon number of the saturated hydrocarbon group corresponds to the number of the carbon atom before replacement.

Examples of the divalent saturated hydrocarbon group are the same examples as the divalent saturated hydrocarbon group of $L^{b1}$.

$L^{b2}$ is preferably a single bond.
$L^{b3}$ is preferably a C1-C4 divalent saturated hydrocarbon group.
$L^{b4}$ is preferably a C1-C8 divalent saturated hydrocarbon group where a hydrogen atom may be replaced by a fluorine atom.
$L^{b5}$ is preferably a single bond or a C1-C8 divalent saturated hydrocarbon group.
$L^{b6}$ is preferably a single bond or a C1-C4 divalent saturated hydrocarbon group where a hydrogen atom may be replaced by a fluorine atom.
$L^{b7}$ is preferably a single bond or a C1-C18 divalent saturated hydrocarbon group where a hydrogen atom may be replaced by a fluorine atom or a hydroxy group, and where a methylene group may be replaced by an oxygen atom or a carbonyl group.

Among these, the group represented by the formula (b1-1) or the formula (b1-3) is preferred.

Examples of the divalent group represented by the formula (b1-1) include the following groups represented by formula (b1-4) to formula (b1-8):

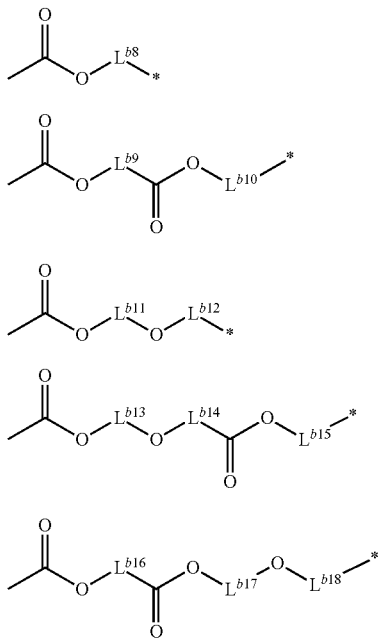

(b1-4)

(b1-5)

(b1-6)

(b1-7)

(b1-8)

wherein $L^{b8}$ represents a single bond or a C1-C22 divalent saturated hydrocarbon group where a hydrogen atom may be replaced by a fluorine atom or a hydroxy group;
$L^{b9}$ represents a C1-C20 divalent saturated hydrocarbon group, and
$L^{b10}$ represents a single bond or a C1-C19 divalent saturated hydrocarbon group where a hydrogen atom may be replaced by a fluorine atom or a hydroxy group, provided that the total number of carbon atoms contained in the group of $L^{b9}$ and $L^{b10}$ is 20 or less;
$L^{b11}$ represents a C1-C21 divalent saturated hydrocarbon group, and $L^{b12}$ represents a single bond or a C1-C20 divalent saturated hydrocarbon group where a hydrogen atom may be replaced by a fluorine atom or a hydroxy group, provided that the total number of carbon atoms contained in the group of $L^{b11}$ and $L^{b12}$ is 21 or less;
$L^{b13}$ represents a C1-C19 divalent saturated hydrocarbon group, $L^{b14}$ represents a single bond or a C1-C18 divalent saturated hydrocarbon group, and $L^{b15}$ represents a single bond or a C1-C18 divalent saturated hydrocarbon group where a hydrogen atom may be replaced by a fluorine atom or a hydroxy group, provided that the total number of carbon atoms contained in the group of $L^{b13}$, $L^{b14}$ and $L^{b15}$ is 19 or less;
$L^{b16}$ represents a C1-C18 divalent saturated hydrocarbon group, $L^{b17}$ represents a C1-C18 divalent saturated hydrocarbon group, and $L^{b18}$ represents a single bond or a C1-C17 divalent saturated hydrocarbon group where a hydrogen atom may be replaced by a fluorine atom or a hydroxy group, provided that the total number of carbon atoms contained in the group of $L^{b16}$, $L^{b17}$ and $L^{b18}$ is 19 or less; and * represents a binding site to Y.
$L^{b8}$ is preferably a C1-C4 divalent saturated hydrocarbon group.
$L^{b9}$ is preferably a C1-C8 divalent saturated hydrocarbon group.
$L^{b10}$ is preferably a single bond or a C1-C19 divalent saturated hydrocarbon group, and more preferably a single bond or a C1-C8 divalent saturated hydrocarbon group.

$L^{b11}$ is preferably a C1-C8 divalent saturated hydrocarbon group.
$L^{b12}$ is preferably a single bond or a C1-C8 divalent saturated hydrocarbon group.
$L^{b13}$ is preferably a C1-C12 divalent saturated hydrocarbon group.
$L^{b14}$ is preferably a single bond or a C1-C6 divalent saturated hydrocarbon group.
$L^{b15}$ is preferably a single bond or a C1-C18 divalent saturated hydrocarbon group, and more preferably a single bond or a C1-C8 divalent saturated hydrocarbon group.
$L^{b16}$ is preferably a C1-C12 divalent saturated hydrocarbon group.
$L^{b17}$ is preferably a C1-C6 divalent saturated hydrocarbon group.
$L^{b18}$ is preferably a single bond or a C1-C17 divalent saturated hydrocarbon group, and more preferably a single bond or a C1-C4 divalent saturated hydrocarbon group.

Examples of the divalent group represented by the formula (b1-3) include the following groups represented by formula (b1-9) to formula (b1-11):

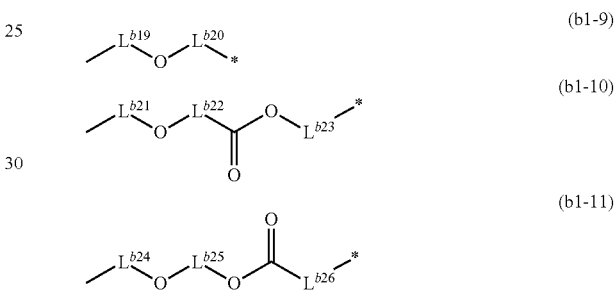

(b1-9)

(b1-10)

(b1-11)

wherein $L^{b19}$ represents a single bond or a C1-C23 divalent saturated hydrocarbon group where a hydrogen atom may be replaced by a fluorine atom, and $L^{b20}$ represent a single bond or a C1-C23 divalent saturated hydrocarbon group where a hydrogen atom may be replaced by a fluorine atom, a hydroxy group or an acyloxy group, and a methylene group contained in an acyloxy group may be replaced by an oxygen atom or a carbonyl group, and a hydrogen atom contained in an acyloxy group may be replaced by a hydroxy group, provided that the total number of carbon atoms contained in the group of $L^{b19}$ and $L^{b20}$ is 23 or less;
$L^{b21}$ represents a single bond or a C1-C21 divalent saturated hydrocarbon group where a hydrogen atom may be replaced by a fluorine atom, $L^{b22}$ represents a single bond or a C1-C21 divalent saturated hydrocarbon group, and $L^{b23}$ represents a single bond or a C1-C21 divalent saturated hydrocarbon group where a hydrogen atom may be replaced by a fluorine atom, a hydroxy group or an acyloxy group, and a methylene group contained in an acyloxy group may be replaced by an oxygen atom or a carbonyl group, and a hydrogen atom contained in an acyloxy group may be replaced by a hydroxy group, provided that the total number of carbon atoms contained in the group of $L^{b21}$, $L^{b22}$ and $L^{b23}$ is 21 or less;
$L^{b24}$ represents a single bond or a C1-C$_{20}$ divalent saturated hydrocarbon group where a hydrogen atom may be replaced by a fluorine atom, $L^{b25}$ represents a single bond or a C1-C21 divalent saturated hydrocarbon group, and $L^{b26}$ represents a single bond or a C1-C20 divalent saturated hydrocarbon group where a hydrogen atom may be replaced by a fluorine atom, a hydroxy group or an acyloxy group, and a methylene group contained in an acyloxy group may be replaced by an oxygen atom or a carbonyl group, and a hydrogen atom contained in an acyloxy group may be replaced by a hydroxy group, provided that the total number of carbon atoms contained in the group of $L^{b24}$, $L^{b25}$ and $L^{b26}$ is 21 or less; and

* represents a binding site to Y.

In formula (b1-9) to formula (b1-11), when a hydrogen atom has been replaced by an acyloxy group, the carbon number of the saturated hydrocarbon group corresponds to the number of the carbon atom, CO and O in addition to the carbon number of the saturated hydrocarbon group.

Examples of the acyloxy group include acetyloxy, propionyloxy, butyryloxy, cyclohexyl carbonyloxy and adamantyl carbonyloxy groups.

Examples of the acyloxy group having a substituent include oxoadamantyl carbonyloxy, hydroxyadamantyl carbonyloxy, oxocyclohexyl carbonyloxy and hydroxycyclohexyl carbonyloxy groups.

Examples of the group represented by the formula (b1-4) include the following ones:

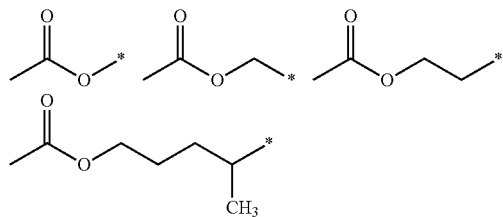

where * represents a binding site to Y.

Examples of the group represented by the formula (b1-5) include the following ones:

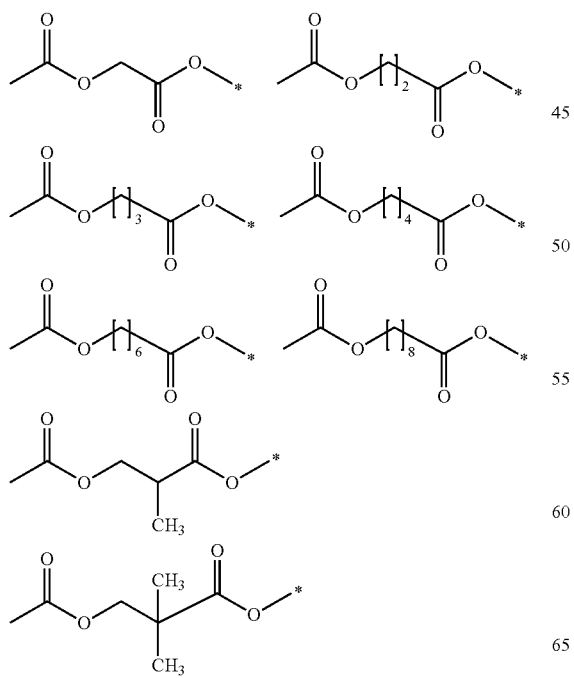

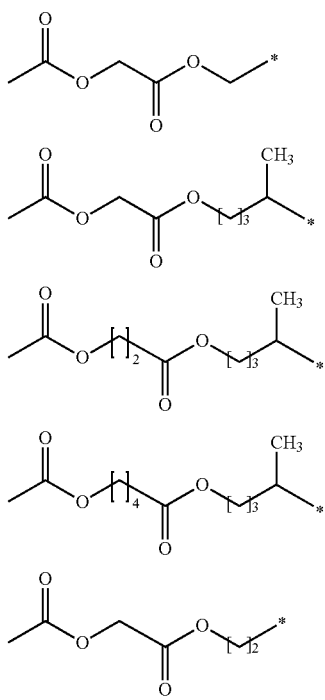

where * represents a binding site to Y.

Examples of the group represented by the formula (b1-6) include the following ones:

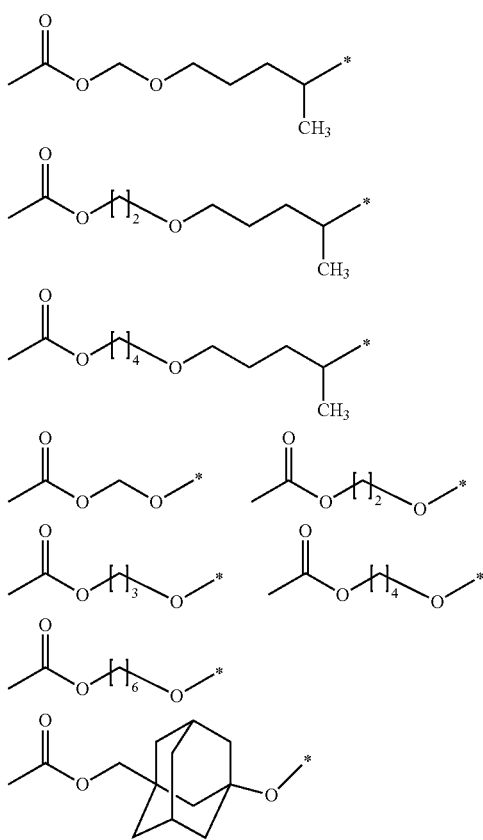

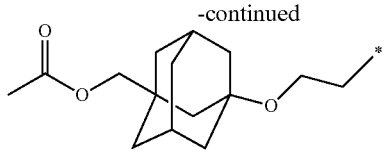

where * represents a binding site to Y.

Examples of the group represented by the formula (b1-7) include the following ones:

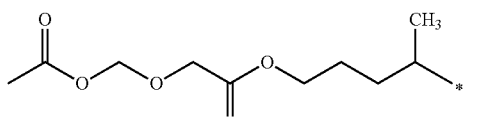
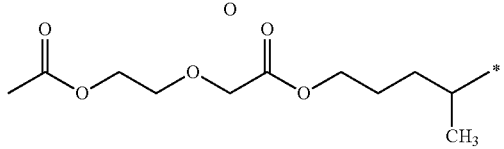
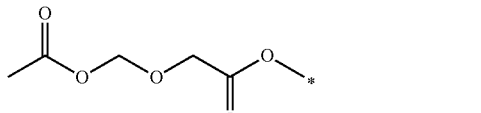
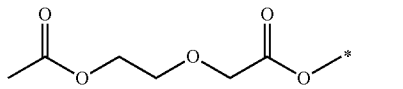
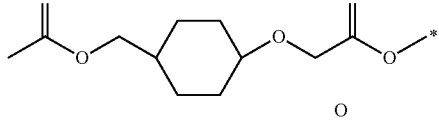
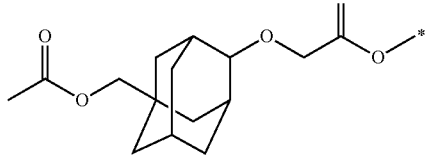
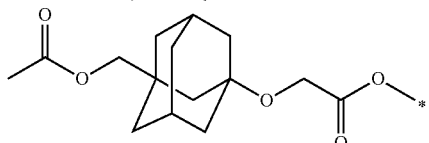
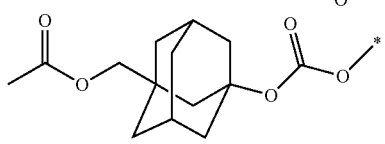
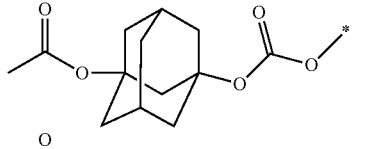
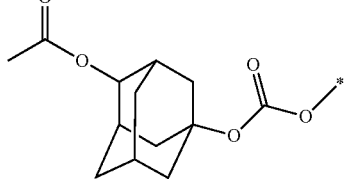

where * represents a binding site to Y.

Examples of the group represented by the formula (b1-8) include the following ones:

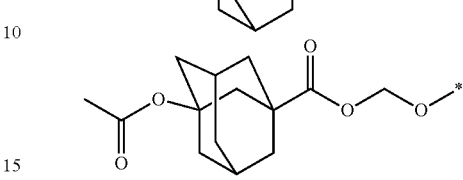

where * represents a binding site to Y.

Examples of the group represented by the formula (b1-2) include the following ones:

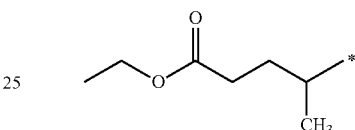
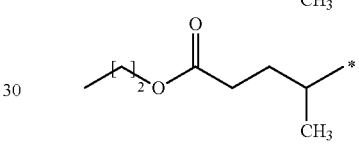
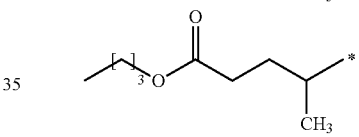
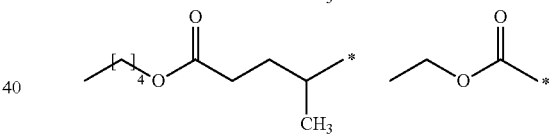
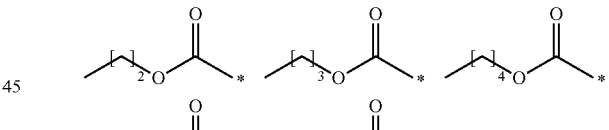
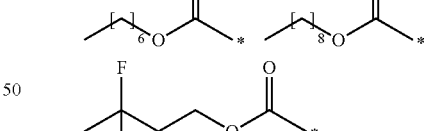
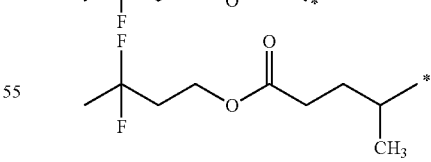

where * represents a binding site to Y.

Examples of the group represented by the formula (b1-9) include the following ones:

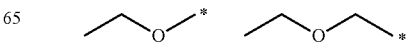
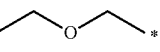

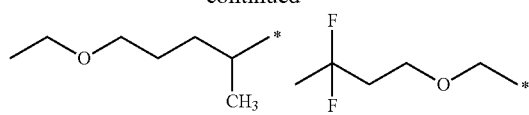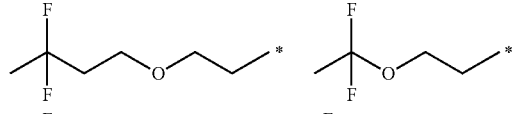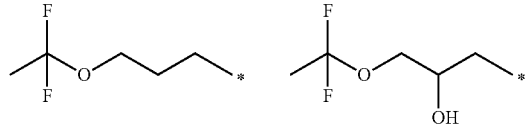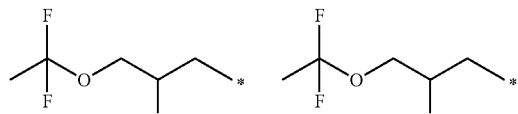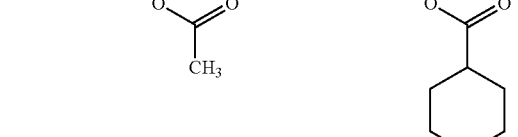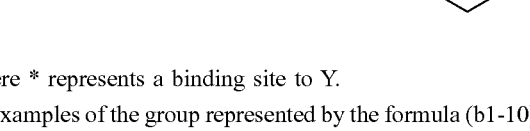
where * represents a binding site to Y.
Examples of the group represented by the formula (b1-10) include the following ones:
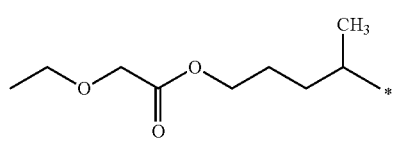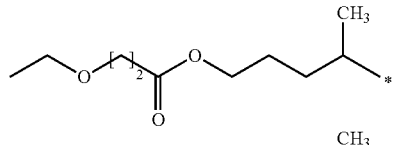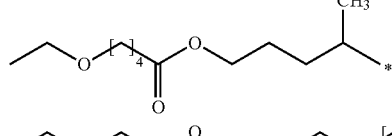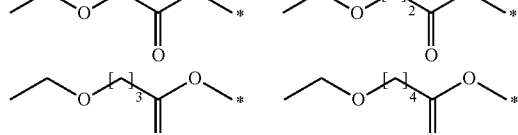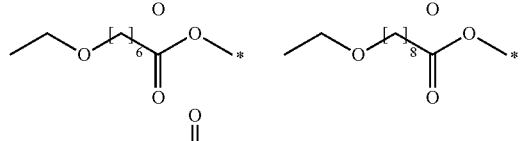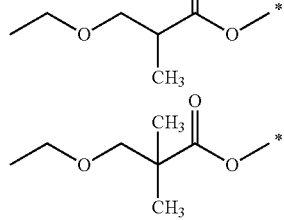
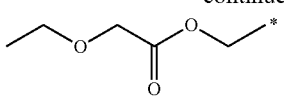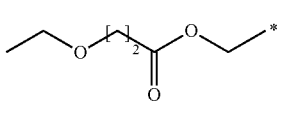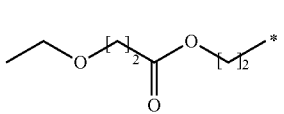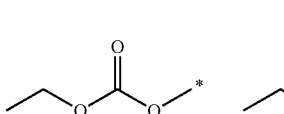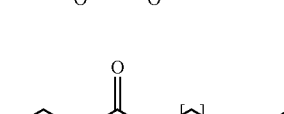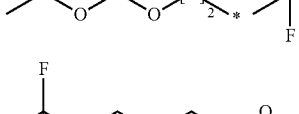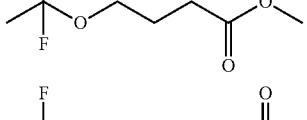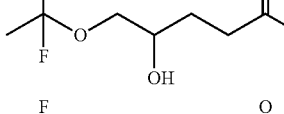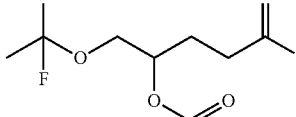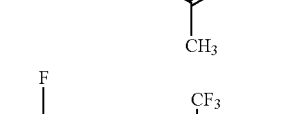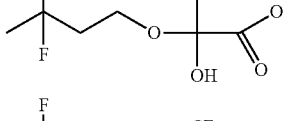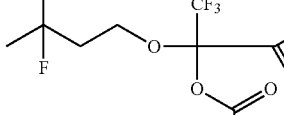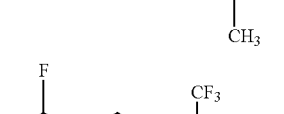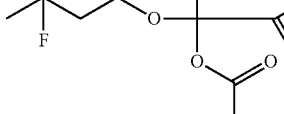

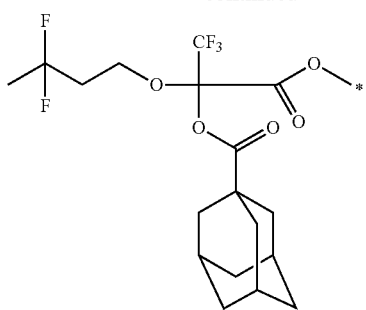
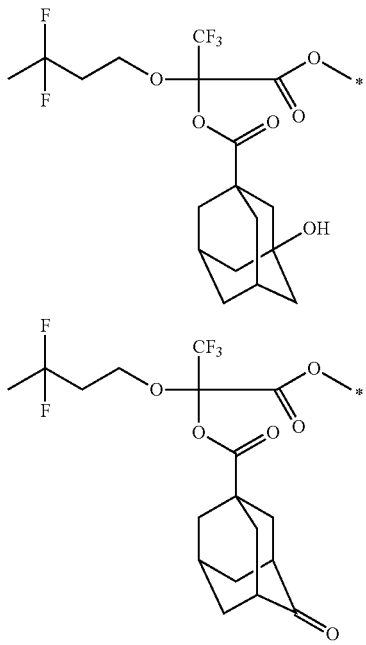
where * represents a binding site to Y.
Examples of the group represented by the formula (b1-11) include the following ones:
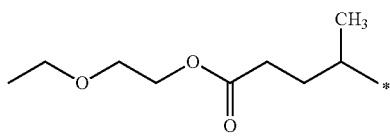
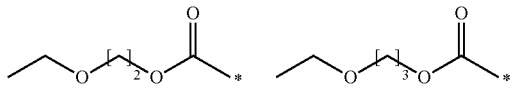
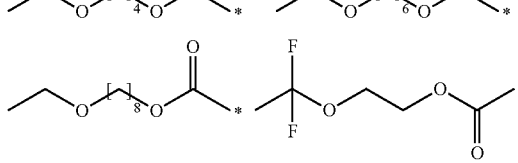
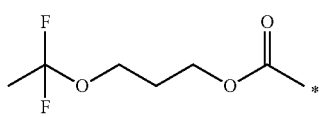
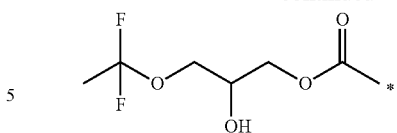
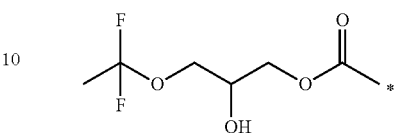
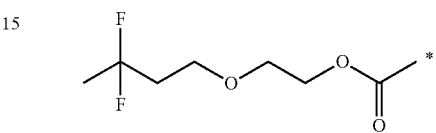
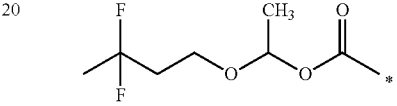
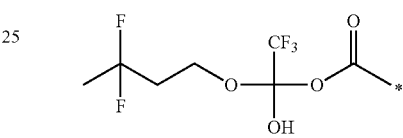
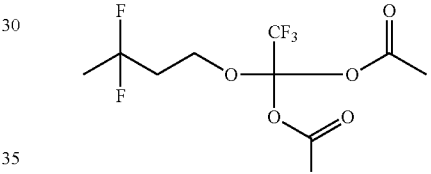
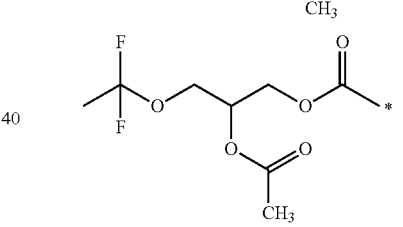
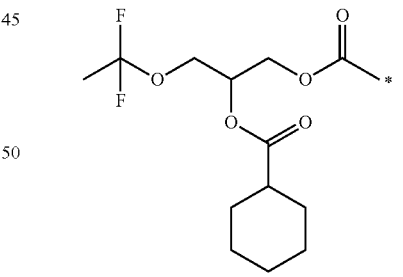
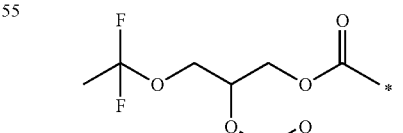
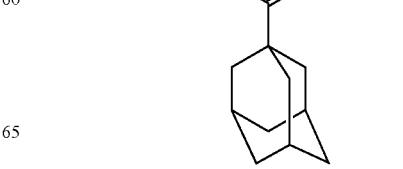

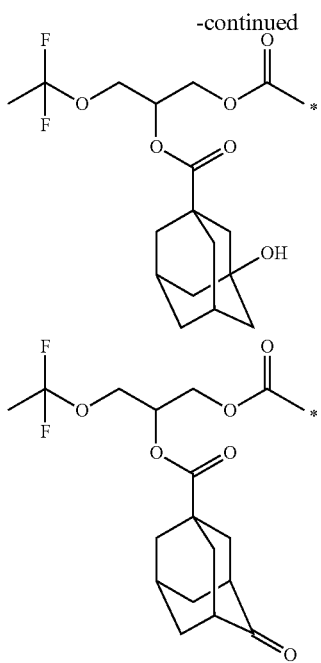
where * represents a binding site to Y.
Examples of the alicyclic hydrocarbon group represented by Y include those represented by formulae (Y1) to (Y11).
Examples of the alicyclic hydrocarbon group represented by Y, in which a methylene group can be replaced by an oxygen atom, a sulfonyl group or a carbonyl group, include those represented by formulae (Y12) to (Y27).
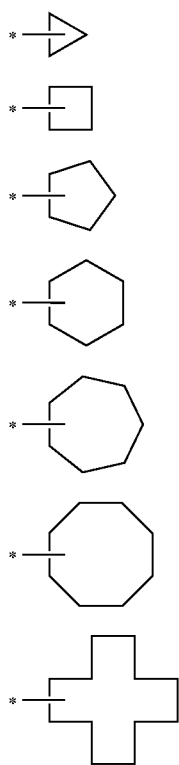
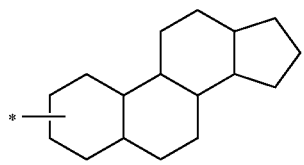
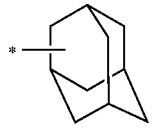
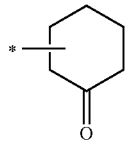
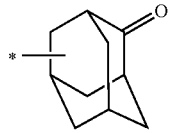
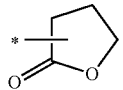
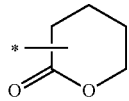
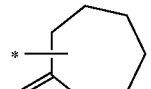
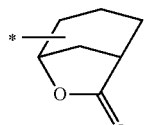
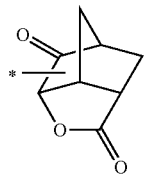

-continued

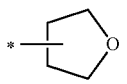
(Y20)

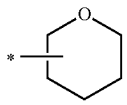
(Y21)

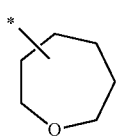
(Y22)

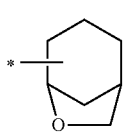
(Y23)

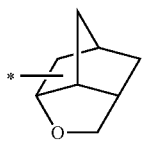
(Y24)

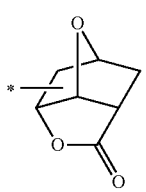
(Y25)

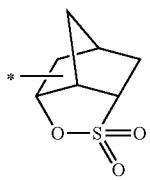
(Y26)

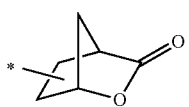
(Y27)

Among them, preferred are those represented by formulae (Y1) to (Y19), more preferred are those represented by formulae (Y11), (Y14), (Y15) and (Y19), and still more preferred are those represented by formulae (Y11) and (Y14).

Examples of the substituents for the methyl group represented by Y include a halogen atom, a hydroxy group, an oxo group, a C1-C12 alkyl group, a C3-C16 alicyclic hydrocarbon group, a C6-C18 aromatic hydrocarbon group, a glycidyloxy group, or —(CH$_2$)$_{ja}$—O—CO—R$^{b1}$ where R$^{b1}$ represents a C1-C16 alkyl group, a C3-C16 alicyclic hydrocarbon group, or a C6-C18 aromatic hydrocarbon group optionally substituted with a C1-C4 alkyl group. The "ja" represents an integer of 0 to 4.

Examples of the substituents for the alicyclic hydrocarbon group represented by Y include a halogen atom, a hydroxy group, an oxo group, a C1-C12 alkyl group, a C1-C12 hydroxy-containing alkyl group, a C3-C16 alicyclic hydrocarbon group, a C1-C12 alkoxy group, a C6-C18 aromatic hydrocarbon group optionally substituted with a C1-C4 alkyl group, a C7-C21 aralkyl group, a C2-C4 acyl group, a glycidyloxy group, or —(CH$_2$)$_{j2}$—O—CO—R$_{b1}$ where R$_{b1}$ represents a C1-C16 alkyl group, a C3-C16 alicyclic hydrocarbon group, or a C6-C18 aromatic hydrocarbon group optionally substituted with a C1-C4 alkyl group. The "j2" represents an integer of 0 to 4.

Examples of the halogen atom include a fluorine atom, a chlorine atom, a bromine atom and an iodine atom.

Examples of the hydroxyl-containing methyl group include a hydroxymethyl group and a hydroxyethyl group.

Examples of alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of an aromatic hydrocarbon group include aryl groups such as a phenyl group, a naphthyl group, an antolyl group, a p-methylphenyl group, p-tert-butylphenyl group, p-adamantylphenyl group, a tolyl group, a xylyl group, a cumenyl group, a mesityl group, a biphenyl group, a phenanthryl group, a 2,6-diethylphenyl group, 2-methyl-6-ethylphenyl group.

Examples of an aralkyl group include a benzyl group, a phenethyl group, a phenylpropyl group, a naphthylmethyl group and a naphthylethyl group.

Examples of an acyl group include an acetyl group, a propionyl group and a butyryl group.

Examples of the group represented by Y include the following ones.

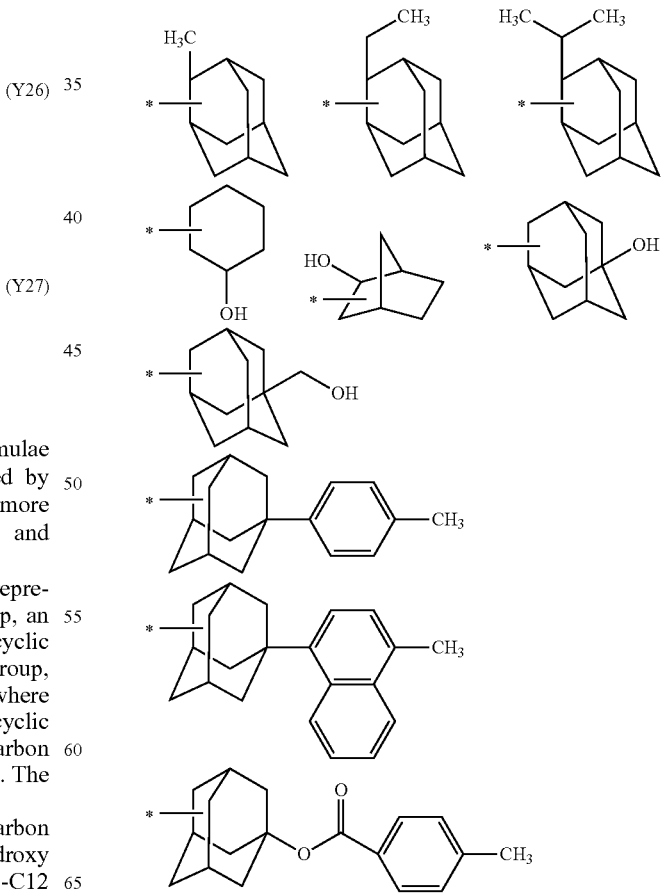

Y is preferably a C3-C18 alicyclic hydrocarbon group where a methylene group can be replaced by an oxygen atom, a sulfonyl group or a carbonyl group and where a hydrogen atom can be replaced by a substituent, more preferably an adamantyl group which can have a substituent such as an oxo group or a hydroxyl group, more preferably an adamantyl group, a hydroxyadamantyl group, or an oxoadamantyl group.

Examples of the sulfonic acid anion of the salt represented by formula (B1) include an anion represented by formulae (B1-A-1) to (B1-A-33), and more preferably an anions represented by formula (B1-A-1) to formula (B1-A-4), formula (B1-A-9), formula (B1-A-10), formula (B1-A-24) to formula (B1-A-33).

(B1-A-1)

(B1-A-2)

(B1-A-3)

(B1-A-4)

(B1-A-5)

(B1-A-6)

(B1-A-7)

(B1-A-8)

(B1-A-9)

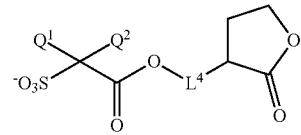

(B1-A-10)

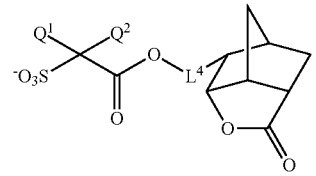

(B1-A-11)

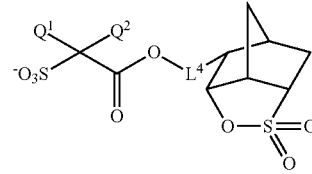

(B1-A-12)

(B1-A-13)

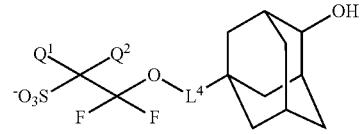

(B1-A-14)

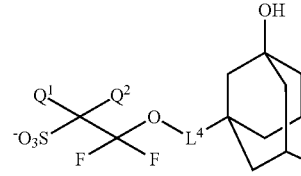

(B1-A-15)

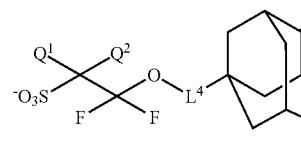

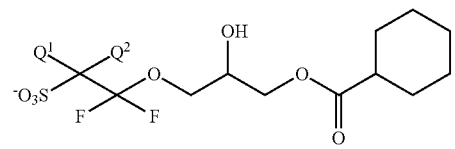

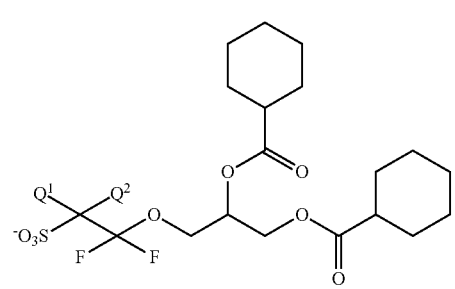

(B1-A-16)
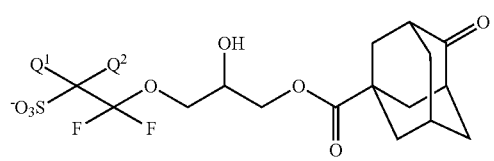
(B1-A-17)
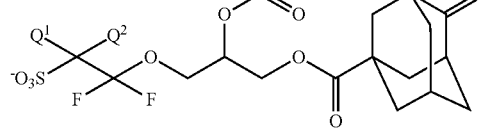
(B1-A-18)
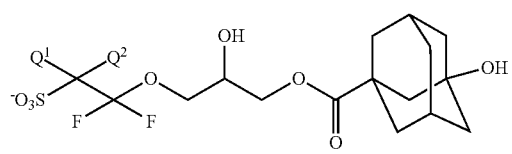
(B1-A-19)
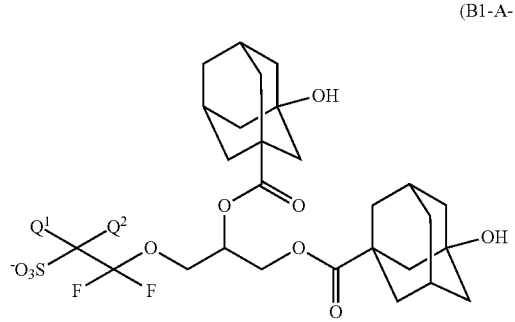
(B1-A-20)
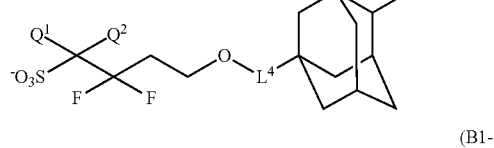
(B1-A-21)
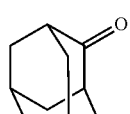
(B1-A-22)
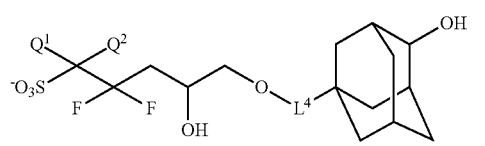
(B1-A-23)
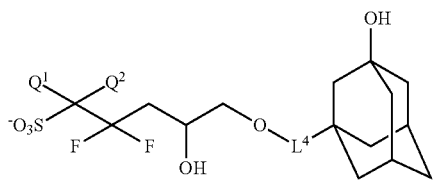
(B1-A-24)
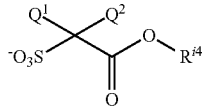
(B1-A-25)
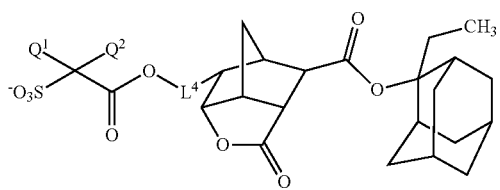
(B1-A-26)
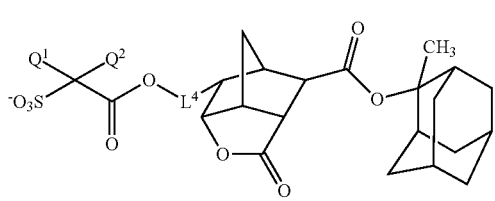
(B1-A-27)
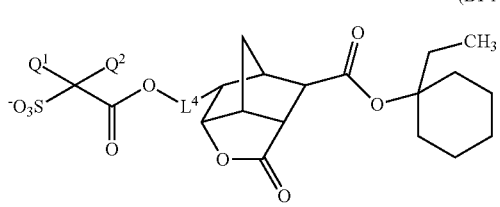
(B1-A-28)
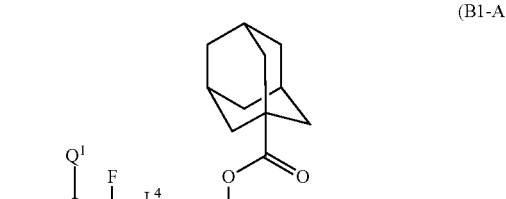
(B1-A-29)
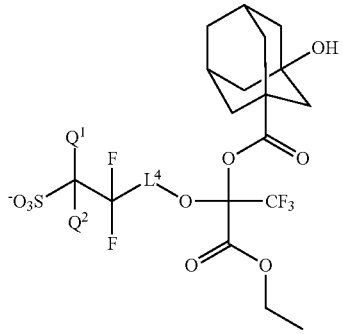

(B1-A-30)
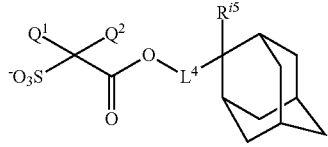

(B1-A-31)
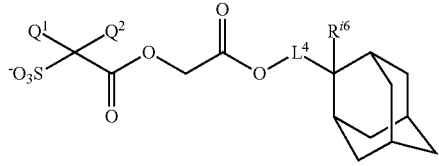

(B1-A-32)
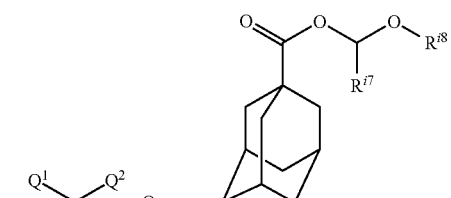

(B1-A-33)
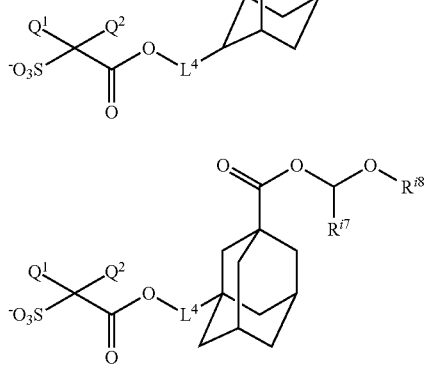

In formula (B1-A-1) to formula (B1-A-33), $R^{i2}$ to $R^{i7}$ each independently represent a C1-C4 alkyl group, and preferably a methyl group or an ethyl group, $R^{i8}$ represent a C1-C12 aliphatic hydrocarbon group, preferably a C1-C4 alkyl group, a C5-C12 monovalent alicyclic hydrocarbon group or a group composed of the alkyl group and the alicyclic hydrocarbon group, more preferably a methyl group, an ethyl group, a cyclohexyl group or an adamantyl group. $L^4$ represents a single bond or a C1-C4 alkanediyl group. $Q^1$ and $Q^2$ represent the same meaning as defined above.

Specific examples of the anion for the salt represented by formula (B1) include those as mentioned in JP2010-204646A1.

Among these, preferred examples of the sulfonic acid anion for the salt represented by the formula (B1) include anions represented by formulae (B1a-1) to (B1a-15).

(B1a-1)
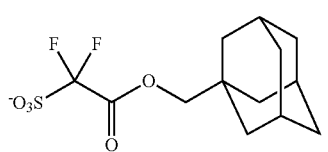

(B1a-2)
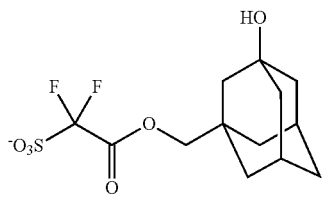

(B1a-3)
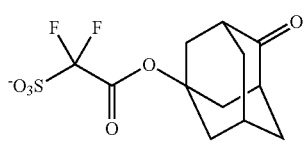

(B1a-4)
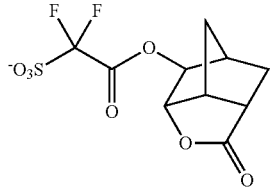

(B1a-5)
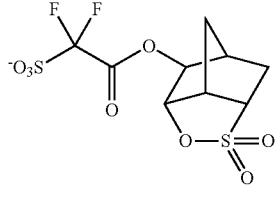

(B1a-6)
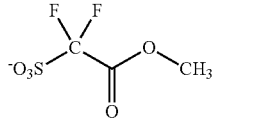

(B1a-7)
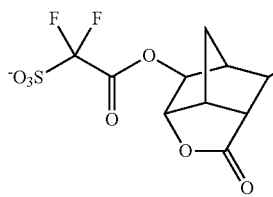

(B1a-8)
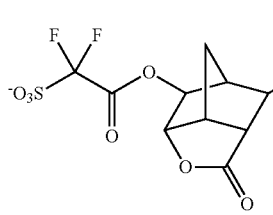

(B1a-9)
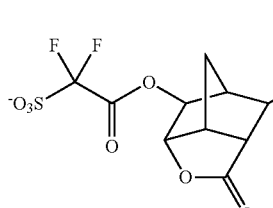

(B1a-10)
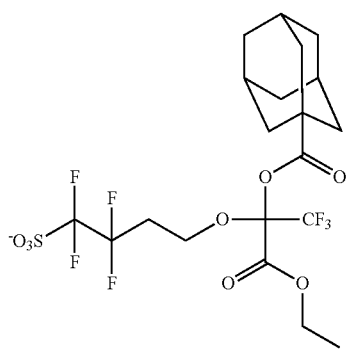

(B1a-11)
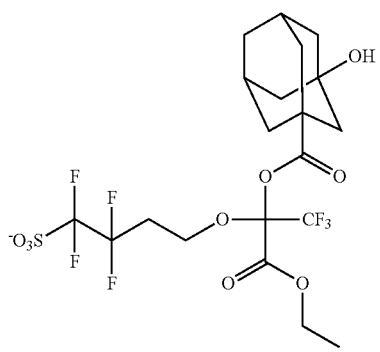

(B1a-12)
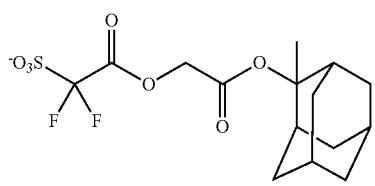

(B1a-13)
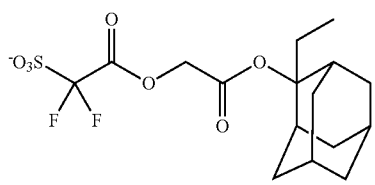

(B1a-14)
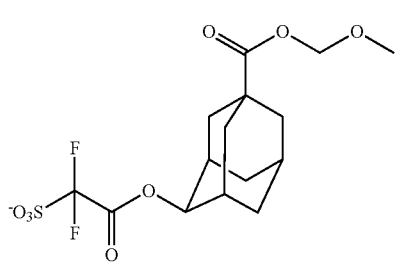

(B1a-15)
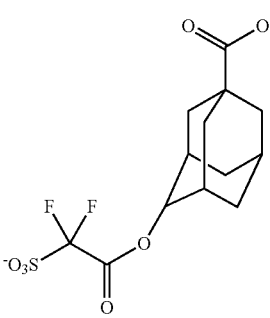

Preferred examples of the sulfonic acid anion include anions represented by the formulae (B1a-1) to (B1a-3) and (B1a-7) to (B1a-15). Examples of the organic cation represented by $Z^+$ include an organic onium cation such as an organic sulfonium cation, an organic iodonium cation, an organic ammonium cation, a benzothiazolium cation and an organic phosphonium cation. As $Z^+$, an organic sulfonium cation and an organic iodonium cation are preferred, and an arylsulfonium cation is more preferred. Herein, the arylsulfonium includes those having one, two or three aryl groups.

Preferable examples of the organic cation represented by $Z^+$ include the organic cations represented by the formulae (b2-1) to (b2-4):

(b2-1)

$$R^{b5}-\underset{R^{b6}}{\overset{R^{b4}}{S+}}$$

(b2-2)
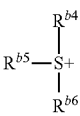

(b2-3)

$$\underset{R^{b10}}{\overset{R^{b9}}{S}}{}^+-\underset{R^{b11}}{\overset{}{CH}}-\overset{O}{\underset{}{C}}-R^{b12}$$

(b2-4)
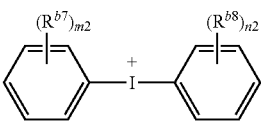

wherein $R^{b4}$, $R^{b5}$ and $R^{b6}$ independently represent a C1-C30 aliphatic hydrocarbon group in which a hydrogen atom can be replaced by a hydroxy group, a C1-C12 alkoxy group or a C6-C18 alicyclic hydrocarbon group, a C3-C36 alicyclic hydrocarbon group in which a hydrogen atom can be replaced by a halogen atom, a C2-C4 acyl group or a glycidyloxy group, and a C6-C36 aromatic hydrocarbon group in which a hydrogen atom can be replaced by a halogen atom, a hydroxy group, or C1-C12 alkoxy group; and $R^{b4}$ and $R^{b5}$, $R^{b4}$ and $R^{b6}$, or $R^{b5}$ and $R^{b6}$ can be bonded each other to form a ring containing $S^+$;

$R^{b7}$ and $R^{b8}$ are independently in each occurrence a hydroxy group, a C1-C12 alkyl group or a C1-C12 alkoxy group;

m2 and n2 independently represents an integer of 0 to 5;

$R^{b9}$ and $R^{b10}$ independently represent a C1-C36 aliphatic hydrocarbon group or a C3-C36 alicyclic hydrocarbon group, or $R^{b9}$ and $R^{b10}$ are bonded each other to form a ring together with the adjacent —$S^+$—, and one or more —$CH_2$— in the ring may be replaced by an oxygen atom, sulfur atom or carbonyl group; and $R^{b11}$ represents a hydrogen atom, a C1-C36 aliphatic hydrocarbon group, a C3-C36 alicyclic hydrocarbon group, or a C6-C18 aromatic hydrocarbon group, and $R^{b12}$ represents a C1-C12 aliphatic hydrocarbon group where a hydrogen atom can be replaced by a C6-C18 aromatic hydrocarbon group, a C3-C18 alicyclic hydrocarbon group, and a C6-C18 aromatic hydrocarbon group optionally substituted with C1-C12 alkoxy group or C1-C12 alkylcarbonyloxy group; or $R^{b11}$ and $R^{b12}$ are bonded each other to form a C1-C10 divalent alicyclic hydrocarbon group which forms a 2-oxo-cycloalkyl group together with the adjacent —CHCO—, and one or more —$CH_2$— in the group may be replaced by an oxygen atom, sulfur atom or carbonyl group; and $R^{b13}$, $R^{b14}$, $R^{b15}$, $R^{b16}$, $R^{b17}$ and $R^{b18}$ independently represent a hydroxy group, a C1-C12 alkyl group or a C1-C12 alkoxy group;

$L^{b31}$ represents —S— or —O—; and o2, p2, s2 and t2 each independently represents an integer of 0 to 5;

q2 and r2 each independently represents an integer of 0 to 4; and u2 represents 0 or 1.

Examples of the aliphatic hydrocarbon group represented by each substituent include an alkyl group such as a methyl group, an ethyl group, a propyl group, an isopropyl group, a butyl group, a sec-butyl group, a tert-butyl group, a pentyl group, a hexyl group, an octyl group, and a 2-ethylhexyl group. The aliphatic hydrocarbon group represented by $R^{b9}$ to $R^{b12}$ is preferably a C1-C18 alkyl group, more preferably a C1-C12 alkyl group.

Examples of the alkyl group where a hydrogen atom has been replaced by an alicyclic hydrocarbon group include 1-(adamantane-1-yl) alkane-1-yl group.

The alicyclic hydrocarbon group represented by each substituent may be monocyclic or polycyclic, a hydrogen atom of which can be replaced by an alkyl group. When a hydrogen atom of it has been replaced by an alkyl group, the total number of carbon atoms is 30 or less. Examples of the monocyclic alicyclic hydrocarbon group include a cycloalkyl group such as a cyclopropyl group, a cyclobutyl group, a cyclopentyl group, a cyclohexyl group, a cycloheptyl group, a cyclodecyl group.

Examples of the polycyclic alicyclic hydrocarbon group include a decahydronaphtyl group, an adamantyl group, a norbornyl group, and the following ones.

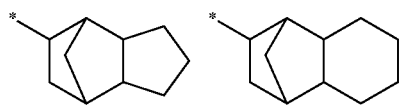

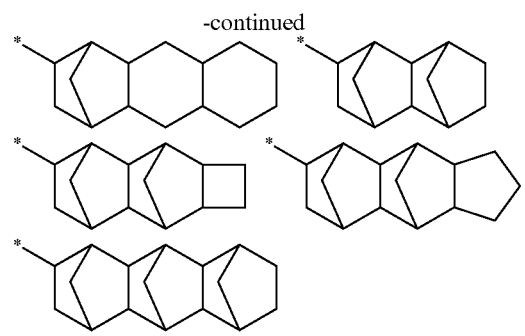

The alicyclic hydrocarbon group represented by $R^{b9}$ to $R^{b12}$ has preferably 3 to 18, more preferably 4 to 12, carbon atoms.

Examples of the alicyclic hydrocarbon group where a hydrogen atom has been replaced by an alkyl group include a methylcyclohexyl group, a 2-alkyladamantane-2-yl group, a methylnorbornyl group, and an isobornyl group.

Preferable examples of the aromatic hydrocarbon group include substituted or unsubstituted phenyl group such as a phenyl group, a tolyl group, a xylyl group, a cumenyl group, a mesityl group, a 4-ethylphenyl group, 4-tert-butylphenyl group, 4-cyclohexylphenyl group, a 4-adamantylphenyl group, a 2, 6-diethylphenyl group, a 2-methyl-6-ethylphenyl group; a biphenyl group, a naphtyl group, a phenanthryl group.

Preferable examples of the aromatic hydrocarbon group where a hydrogen atom has been replaced by an alkoxy group include 4-methoxyphenyl group.

Preferable examples of the alkyl group where a hydrogen atom has been replaced by an aromatic hydrocarbon group, i.e., an aralkyl group, include a benzyl group, a phenethyl group, a phenylpropyl group, a trityl group, a naphthylmethyl group and a naphthylethyl group.

When the aromatic hydrocarbon group has an alkyl group or an alicyclic hydrocarbon group as a substituent, the substituent is preferably a C1-C12 alkyl group or a C3-C18 alicyclic hydrocarbon group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the C2-C4 acyl group include an acetyl group, a propionyl group and a butyryl group.

Examples of the halogen atom include a fluorine atom, a chlorine atom, a bromine atom and an iodine atom.

Preferable examples of the alkylcarbonyloxy group include a methylcarbonyloxy group, an ethylcarbonyloxy group, n-propylcarbonyloxy group, an isopropylcarbonyloxy group, n-butylcarbonyloxy group, sec-butylcarbonyloxy group, a tert-butylcarbonyloxy group, a pentylcarbonyloxy group, a hexylcarbonyloxy group, an octylcarbonyloxy group and 2-ethyl hexylcarbonyloxy group.

The ring containing $S^+$ formed by bonding $R^{b4}$ and $R^{b5}$, $R^{b4}$ and $R^{b6}$, or $R^{b5}$ and $R^{b6}$ each other may be a monocyclic ring, a polycyclic ring, an aromatic ring, a non-aromatic ring, a saturated ring or a unsaturated ring. The ring can contain a sulfur atom or oxygen atom in addition to S. The ring preferably has 3 to 18 carbon atoms, and more preferably has 4 to 13 carbon atoms. Examples of such ring include, 3 to 12-membered rings, preferably 3 to 7-membered rings, specifically the following ones.

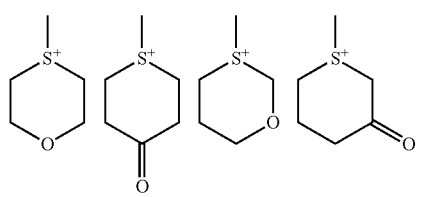

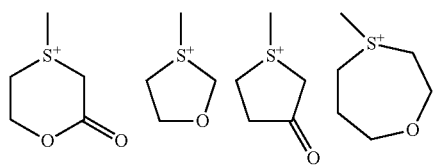

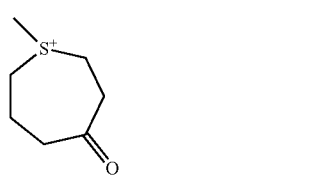

Examples of the ring group formed by bonding $R^{b9}$ and $R^{b10}$ together with the adjacent $S^+$ and the divalent alicyclic hydrocarbon group include, 3 to 12-membered rings, preferably 3 to 7-membered rings, specifically a thiolan-1-ium ring (tetrahydrothiophenium ring), a thian-1-ium ring and a 1,4-oxathian-4-ium ring.

Examples of the ring group formed by bonding $R^{b11}$ and $R^{b12}$ include 3 to 12-membered rings, preferably 3 to 7-membered rings, specifically oxocyclopentane ring, oxocyclohexane ring, oxonorbornane ring and oxoadamantane ring.

Among the above-mentioned cations, preferred is the cation represented by the formula (b2-1).

Examples of the cation represented by the formula (b2-1) include the following ones.

(b2-c-1)

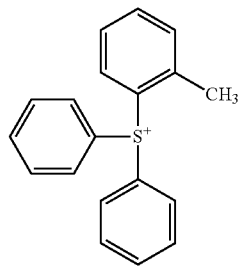

(b2-c-2)

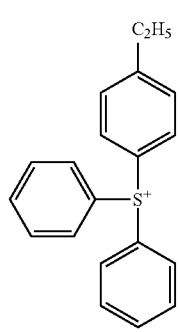

(b2-c-3)

(b2-c-4)

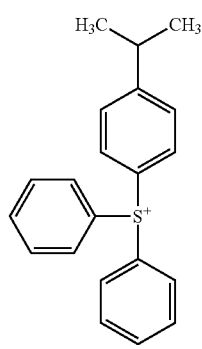

(b2-c-5)

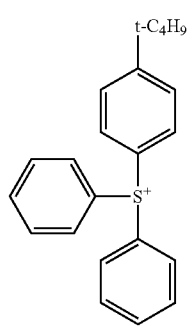

(b2-c-6)

(b2-c-7)

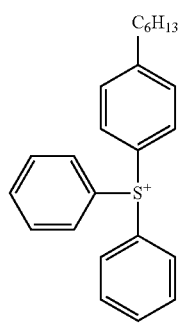

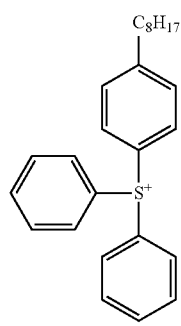 (b2-c-8)
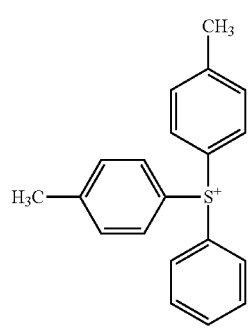 (b2-c-9)
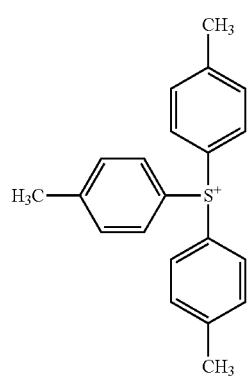 (b2-c-10)
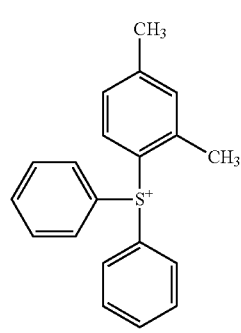 (b2-c-11)
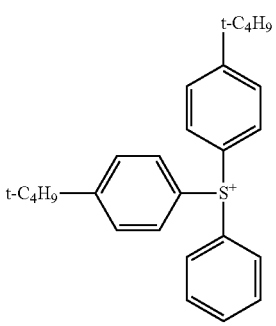 (b2-c-12)
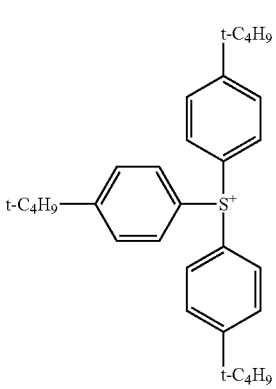 (b2-c-13)
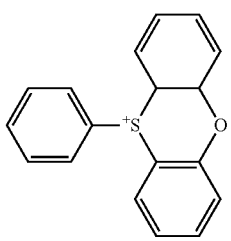 (b2-c-14)
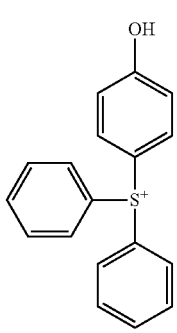 (b2-c-15)
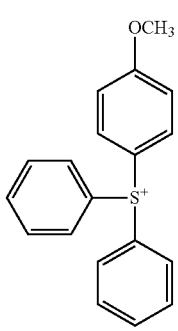 (b2-c-16)

(b2-c-17) 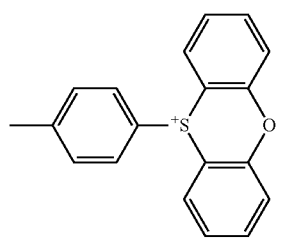
(b2-c-18) 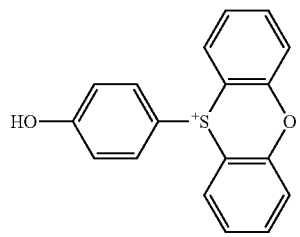
(b2-c-19) 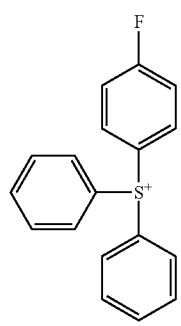
(b2-c-20) 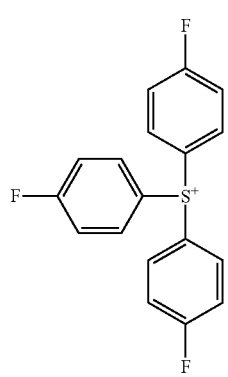
(b2-c-21) 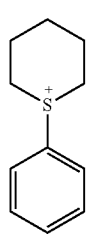
(b2-c-22) 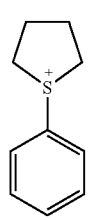
(b2-c-23) 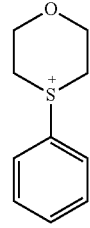
(b2-c-24) 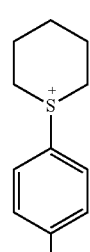
(b2-c-25)
(b2-c-26)
(b2-c-27)
Examples of the cation represented by the formula (b2-2) include the following ones.

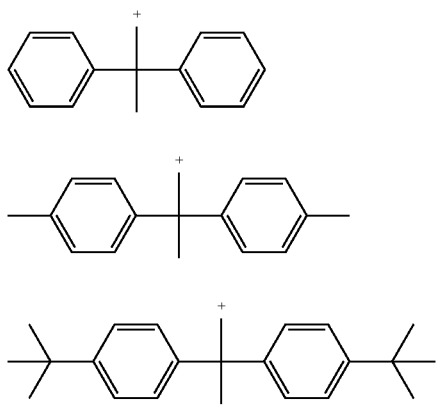
(b2-c-28)
(b2-c-29)
(b2-c-30)
Examples of the cation represented by the formula (b2-3) include the following ones.
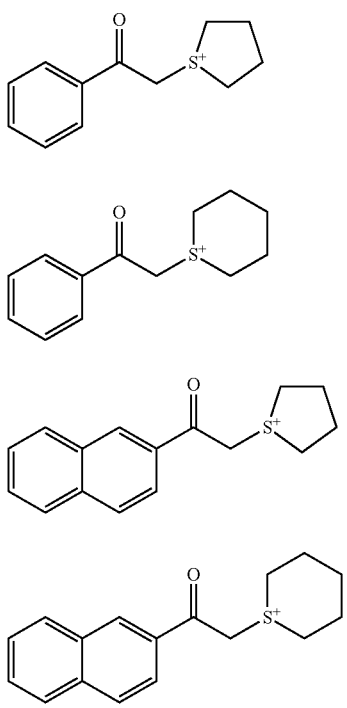
(b2-c-31)
(b2-c-32)
(b2-c-33)
(b2-c-34)
Examples of the cation represented by the formula (b2-4) include the following ones.
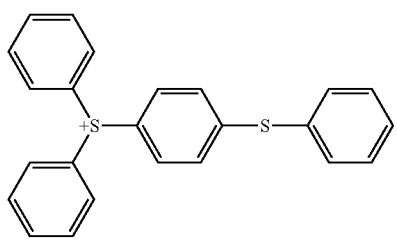
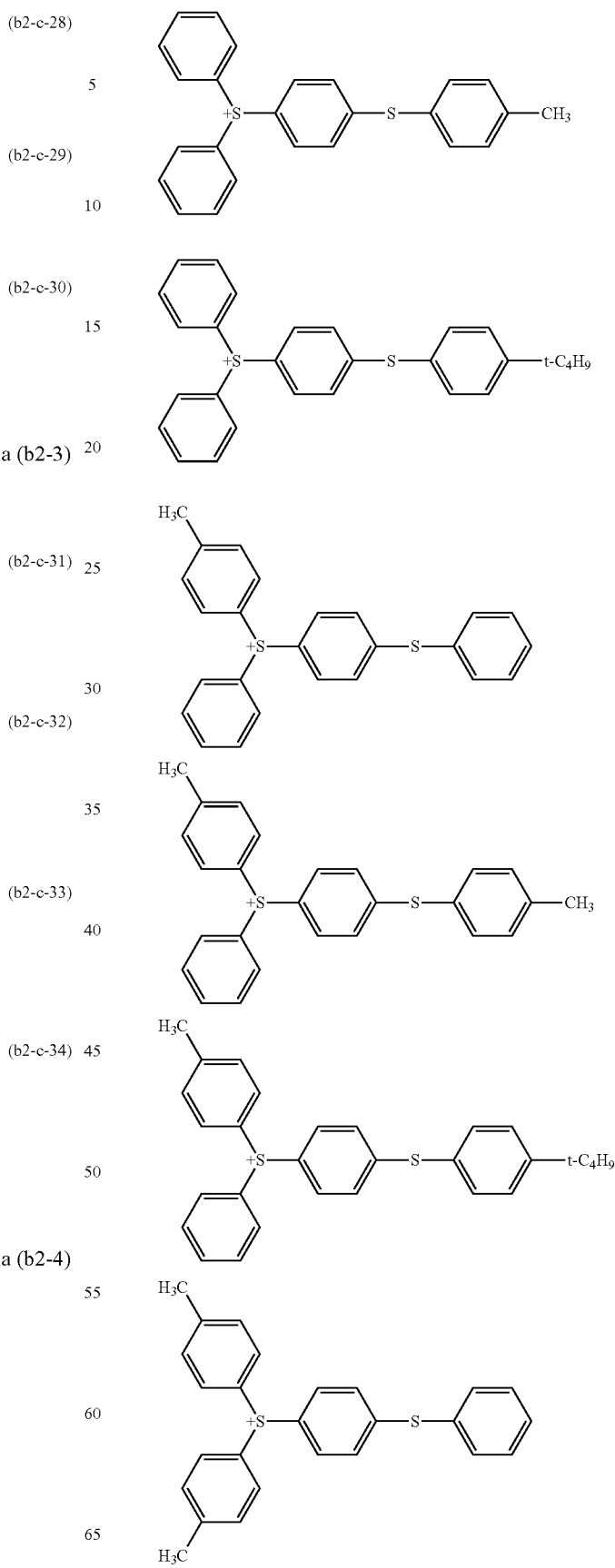

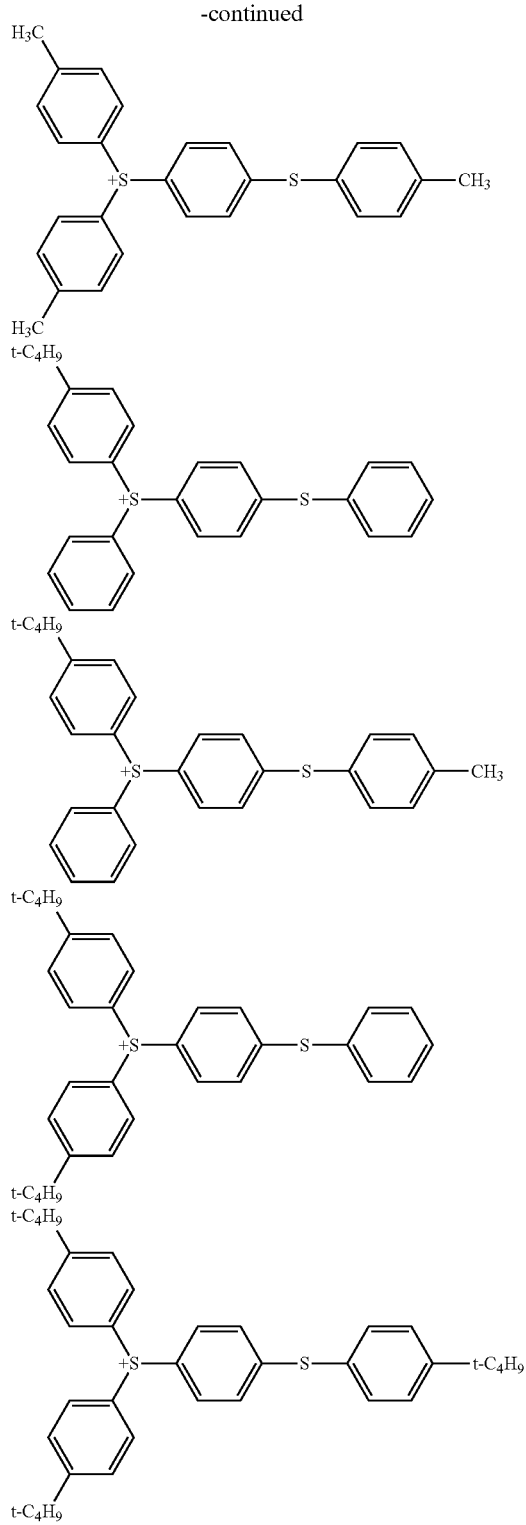

by formulae (B1-1), (B1-2), (B1-3), (B1-5), (B1-6), (B1-7), (B1-11), (B1-12), (B1-13), (B1-14), (B1-17), (B1-20), (B1-21), (B1-22), (B1-23), (B1-24), (B1-25), (B1-26) and (B1-29).

(B1-1)

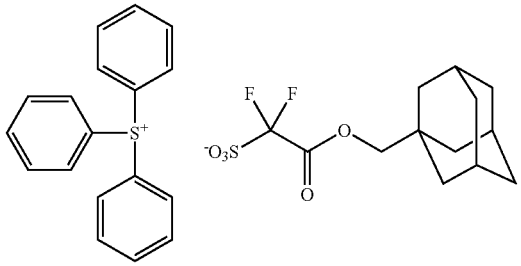

(B1-2)

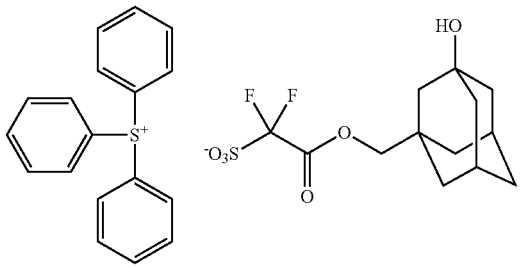

(B1-3)

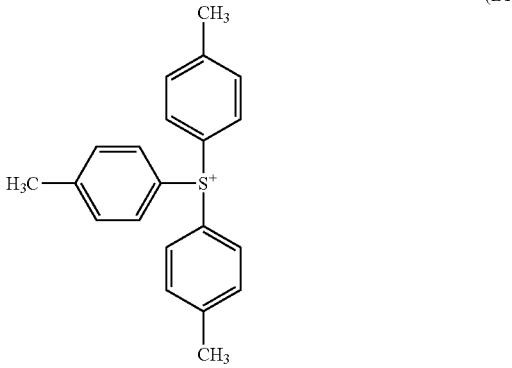

(B1-4)

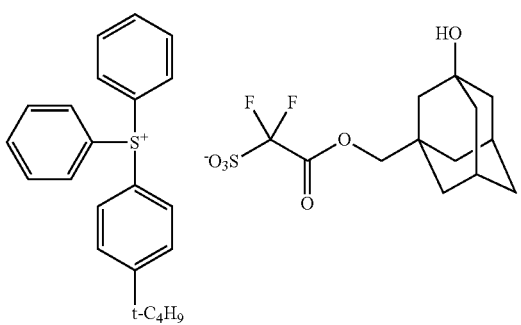

The acid generator for the photoresist composition of the disclosure is preferably those having an anion represented by any one of the formulae (B1a-1) to (B1a-3) and (B1a-7) to (B1a-15) and a cation represented by any one of the formulae (b2-1) and (b2-3).

The acid generator is preferably those represented by formulae (B1-1) to (B1-30), more preferably those having an arylsulfonium cation, still more preferably those represented -continued
(B1-5)
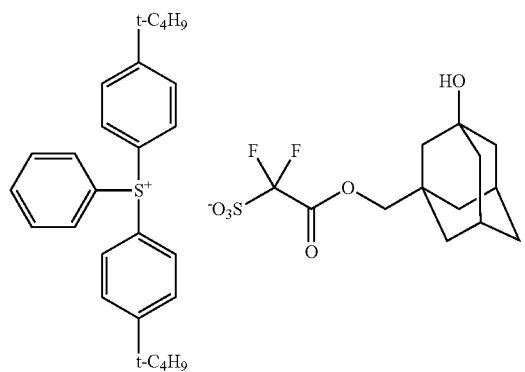
(B1-6)
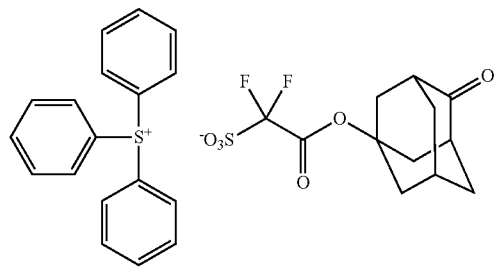
(B1-7)
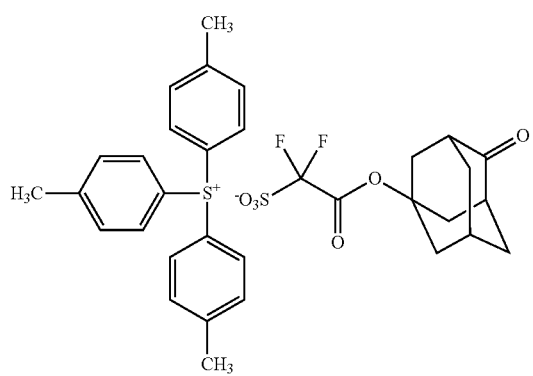
(B1-8)
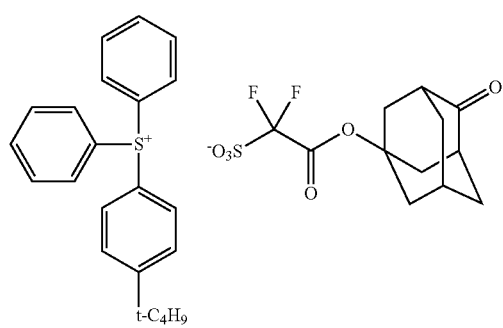
-continued
(B1-9)
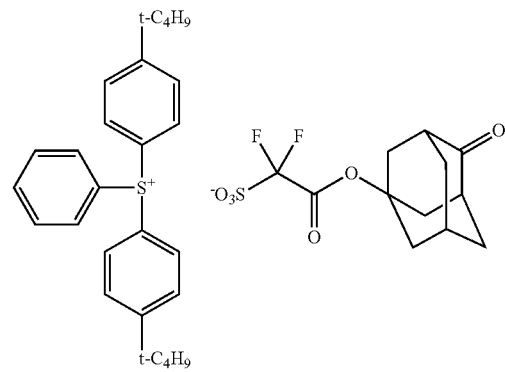
(B1-9)
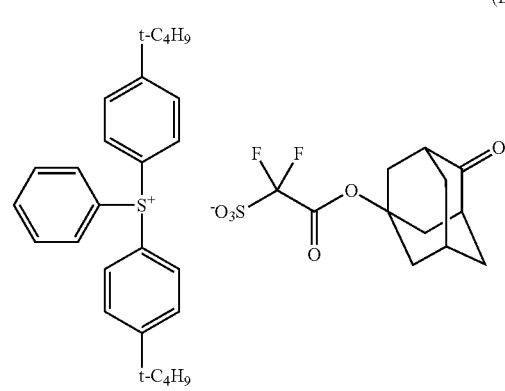
(B1-10)
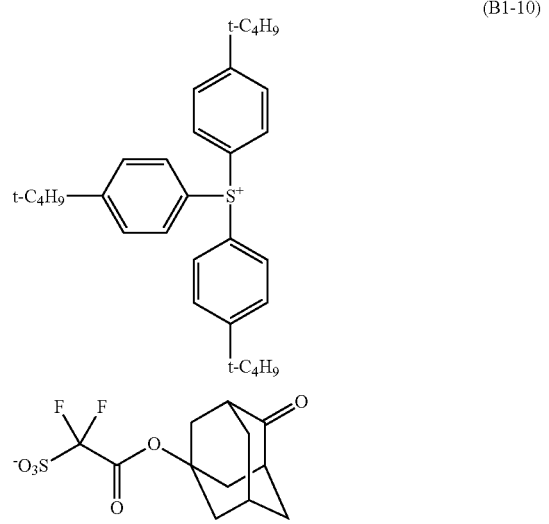
(B1-11)
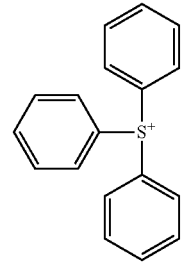

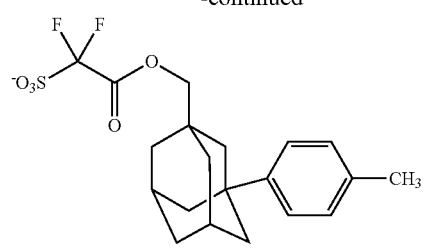
(B1-12)
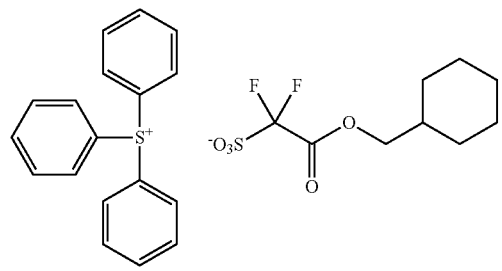
(B1-13)
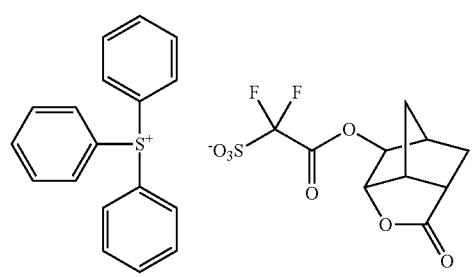
(B1-14)
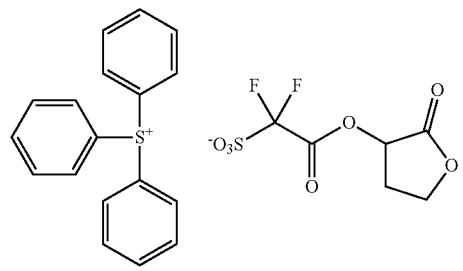
(B1-15)
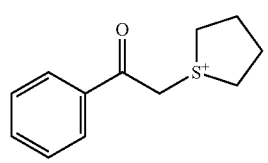
(B1-16)
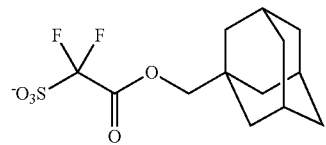
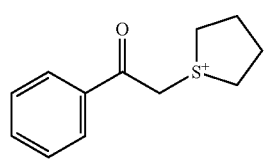
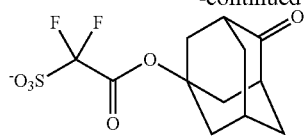
(B1-17)
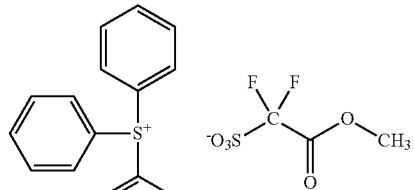
(B1-18)
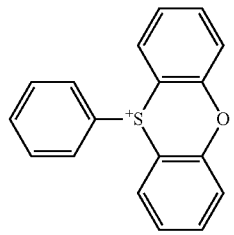
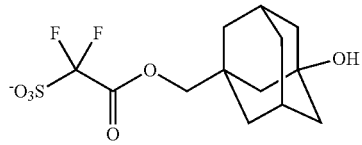
(B1-19)
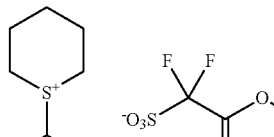
(B1-20)
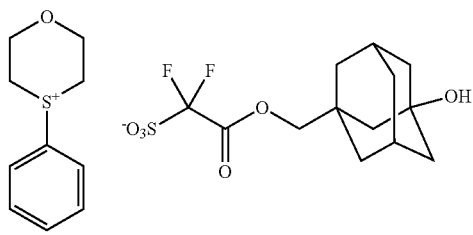
(B1-21)
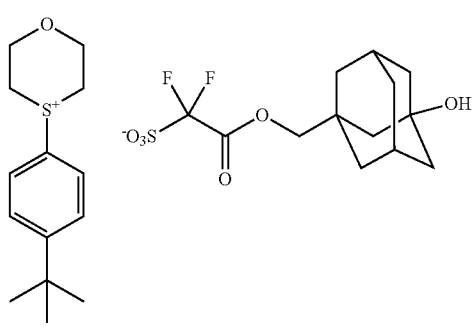

(B1-22) 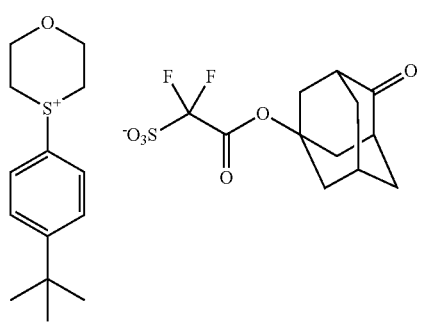
(B1-25) 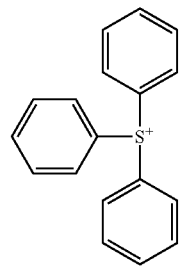
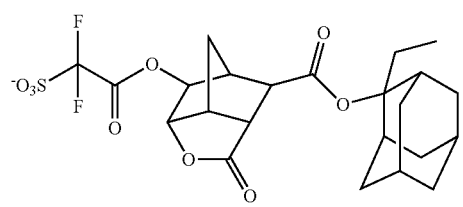
(B1-23) 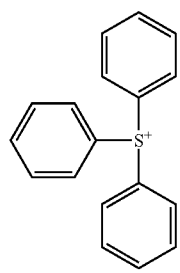
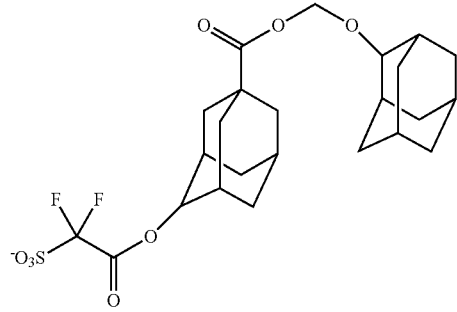
(B1-26) 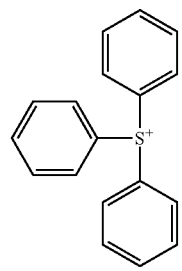
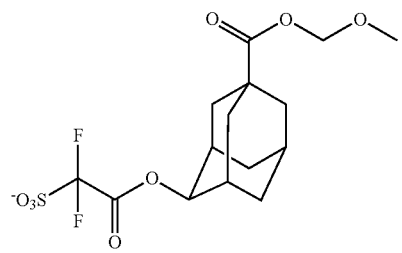
(B1-24) 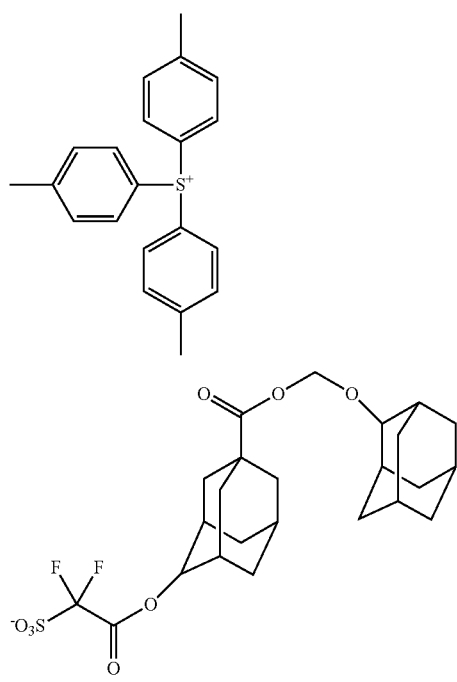
(B1-27) 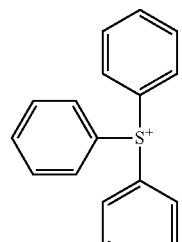
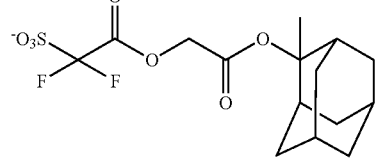

-continued

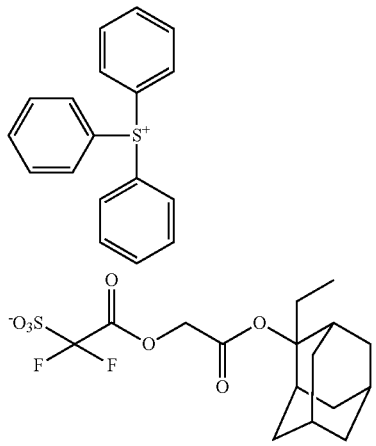
(B1-28)

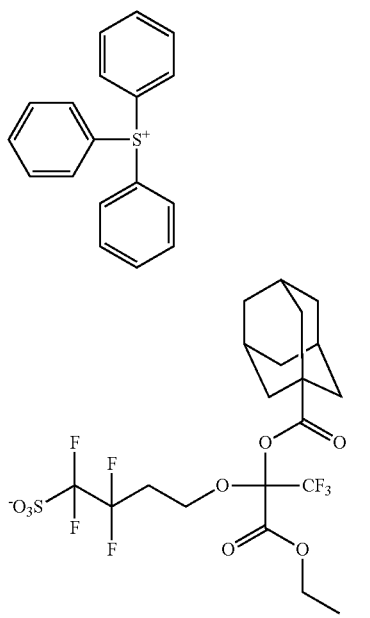
(B1-29)

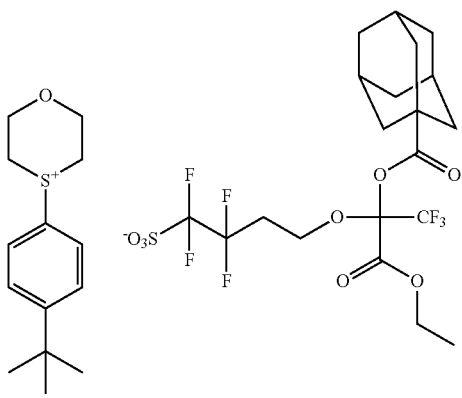
(B1-30)

The amount of the acid generator represented by formula (B1) is preferably 30% by mass or more, and 100% by mass or less, more preferably 50% by mass or more, and 100% by mass or less, and still more preferably substantially 100% by mass with respect to total amount of the acid generator in the photoresist composition.

The amount of the acid generator is preferably 1 weight parts or more, more preferably 3 weight parts or more, and preferably 30 weight parts or less, and more preferably 25 weight parts or less, relative to 100 weight parts of the resin (A).

The photoresist compositions of the disclosure may further contain a quencher. The "quencher" has the property that it can trap an acid, especially an acid generated from the acid generator by applying a radiation.

Examples of the quencher include a basic nitrogen-containing organic compound and a salt lower in acidity than an acid generated from the acid generator.

Examples of the basic nitrogen-containing organic compound include an amine compound such as an aliphatic amine, an aromatic amine and an ammonium salt. Examples of the aliphatic amine include a primary amine, a secondary amine and a tertiary amine. Examples of the aromatic amine include an aromatic amine in which an aromatic ring has an amino group such as aniline and a heteroaromatic amine such as pyridine. Examples of the quencher include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, pentylamine, dioctylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyidihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris [2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenyl methane, piperazine, morpholine, piperidine, hindered amine compound having a piperidine structure, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl) propane, 1,2-di(4-pyridyloxy) ethane, di(2-pyridyl)ketone, 4,4'-dipyridyl sulfide, 4,4'-dipyridyl disulfide, 2,2'-dipyridylamine, 2, 2'-dipicolylamine and bipyridine. Examples of the ammonium salts include quaternary ammonium salts such as tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl) trimethylammonium hydroxide (so-called "choline").

For the photoresist composition, the salt lower in acidity than an acid generated from the acid generator can be selected according to the acid generator to be used, examples of which include the salts as shown below and those as mentioned in JP2012-229206A1, JP2012-6908A1, JP2012-72109A1, JP2011-39502A1 and JP2011-191745A1.

The acidity in the weak acid salt is shown by the acid dissociation constant (pKa). The acid dissociation constant of acid generated from the weak acid salt is usually $-3<pKa$. The weak acid salt is preferably a salt of $-1<pKa<7$, and more preferably a salt of $0<pKa<5$.

Specific examples of the weak acid salt include the following ones. Among them, the quencher is preferably a salt represented by formula (D).

125
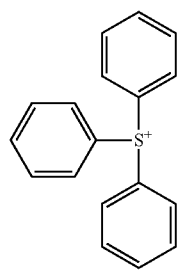
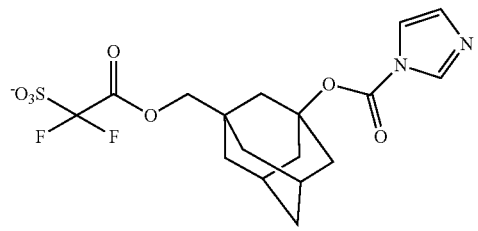
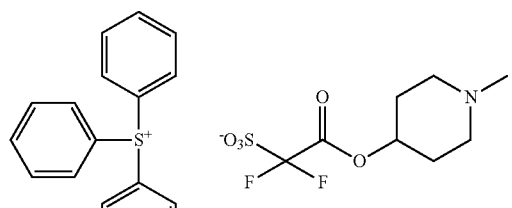
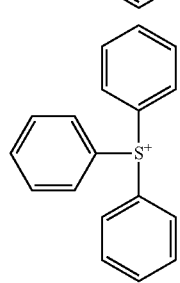
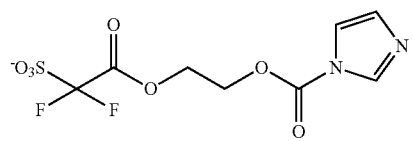
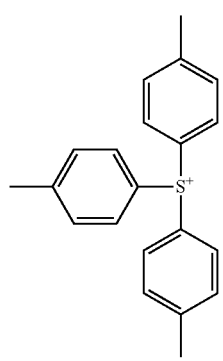
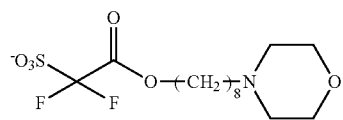
126
-continued
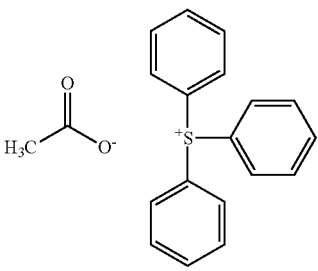
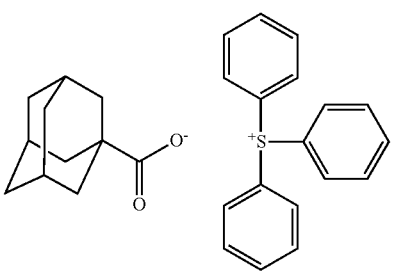
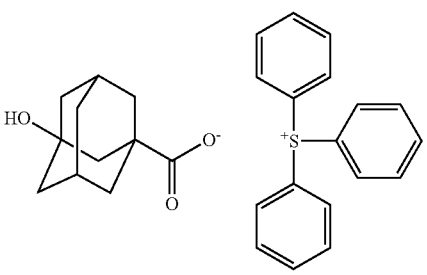
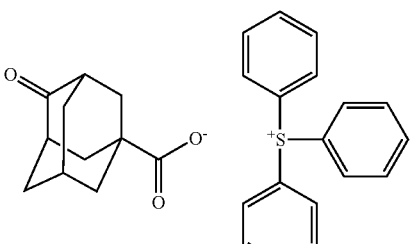
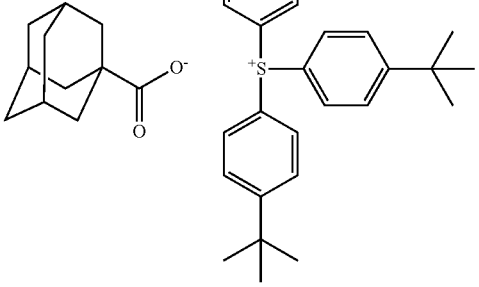

-continued

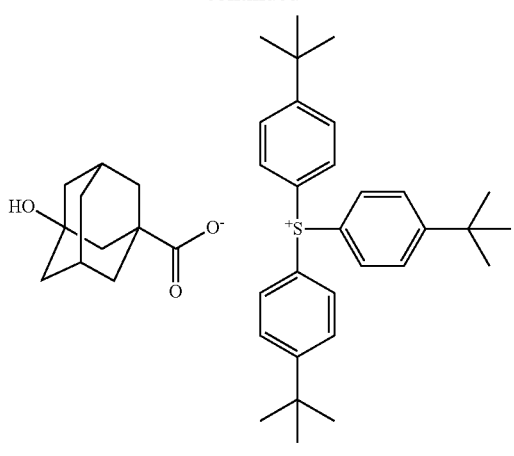

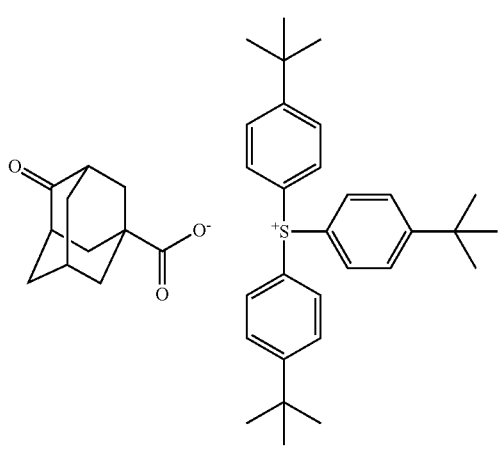

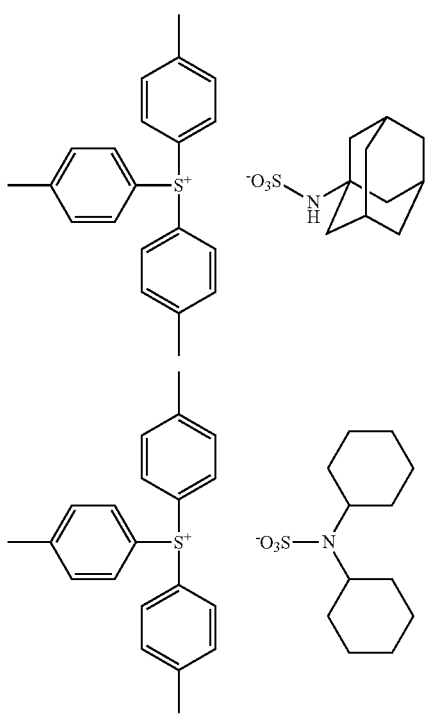

-continued

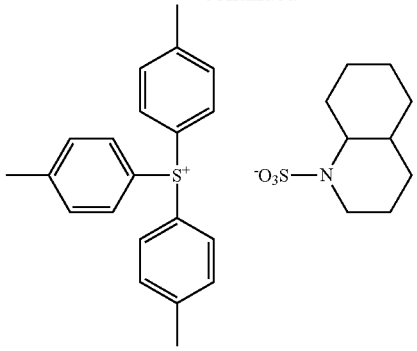

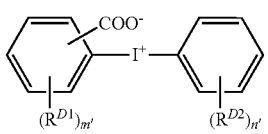

(D)

In the formula (D), $R^{D1}$ and $R^{D2}$ in each occurrence independently represent a C1-C12 hydrocarbon group, a C1-C6 alkoxyl group, a C2-C7 acyl group, a C2-C7 acyloxy group, a C2-C7 alkoxycarbonyl group, a nitro group or a halogen atom;

m' and n' each independently represent an integer of 0 to 4.

Examples of the hydrocarbon group for $R^{D1}$ and $R^{D2}$ include any of an aliphatic hydrocarbon group, an alicyclic hydrocarbon group, an aromatic hydrocarbon group and a combination thereof.

Examples of the aliphatic hydrocarbon group include an alkyl group such as methyl, ethyl, propyl, isopropyl, butyl, isobutyl, tert-butyl, pentyl, hexyl and nonyl groups.

The alicyclic hydrocarbon group is any one of monocyclic or polycyclic hydrocarbon group, and saturated or unsaturated hydrocarbon group. Examples thereof include a cycloalkyl group such as cyclopropyl, cyclobutyl, cyclopentyl, cyclohexyl, cyclononyl and cyclododecyl groups; adamantyl and norbornyl groups.

Examples of the aromatic hydrocarbon group include an aryl group such as phenyl, 1-naphthyl, 2-naphthyl, 2-methylphenyl, 3-methylphenyl, 4-methylphenyl, 4-ethylphenyl, 4-propylphenyl, 4-isopropylphenyl, 4-butylphenyl, 4-tert-butylphenyl, 4-hexylphenyl, 4-cyclohexylphenyl, anthryl, p-adamantylphenyl, tolyl, xylyl, cumenyl, mesityl, biphenyl, phenanthryl, 2,6-diethylphenyl and 2-methyl-6-ethylphenyl groups.

Examples of the combination thereof include an alkyl-cycloalkyl group, a cycloalkyl-alkyl group and an aralkyl group (e.g., phenylmethyl, 1-phenylethyl, 2-phenylethyl, 1-phenyl-1-propyl, 1-phenyl-2-propyl, 2-phenyl-2-propyl, 3-phenyl-1-propyl, 4-phenyl-1-butyl, 5-phenyl-1-pentyl and 6-phenyl-1-hexyl groups). Examples of the alkoxyl group include methoxy and ethoxy groups.

Examples of the acyl group include acetyl, propanoyl, benzoyl and cyclohexanecarbonyl groups.

Examples of the acyloxy group include a group in which oxy group (—O—) bonds to an acyl group.

Examples of the alkoxycarbonyl group include a group in which the carbonyl group (—CO—) bonds to the alkoxy group.

Example of the halogen atom is a chlorine atom, a fluorine atom and bromine atom.

In the formula (D), $R^{D1}$ and $R^{D2}$ in each occurrence independently preferably represent a C1-C8 alkyl group, a C3-C10 cycloalkyl group, a C1-C6 alkoxyl group, a C2-C4 acyl group, a C2-C4 acyloxy group, a C2-C4 alkoxycarbonyl group, a nitro group or a halogen atom. m' and n' independently preferably represent an integer of 0 to 3, more preferably an integer of 0 to 2, and more preferably 0. Specific examples of the salt of the formula (D) include compounds below.

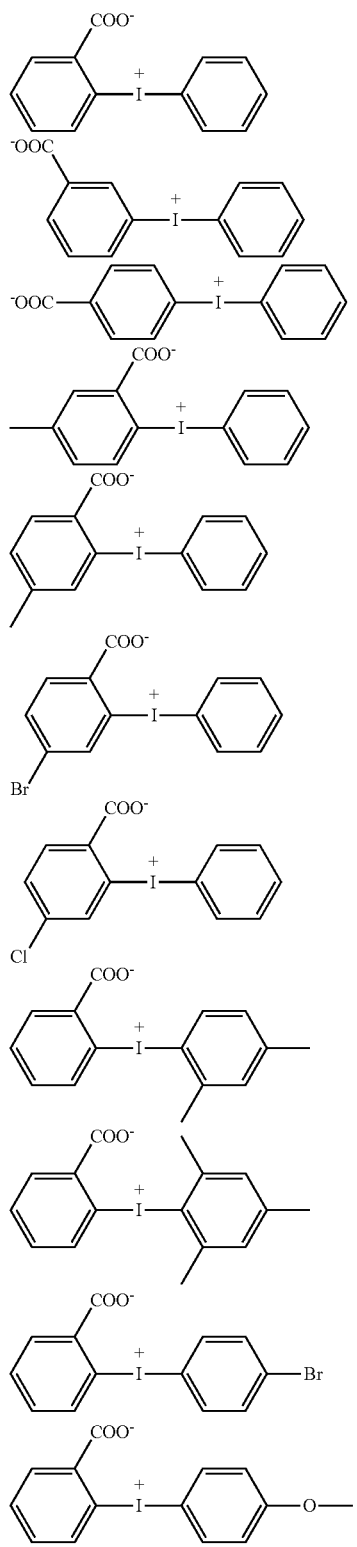

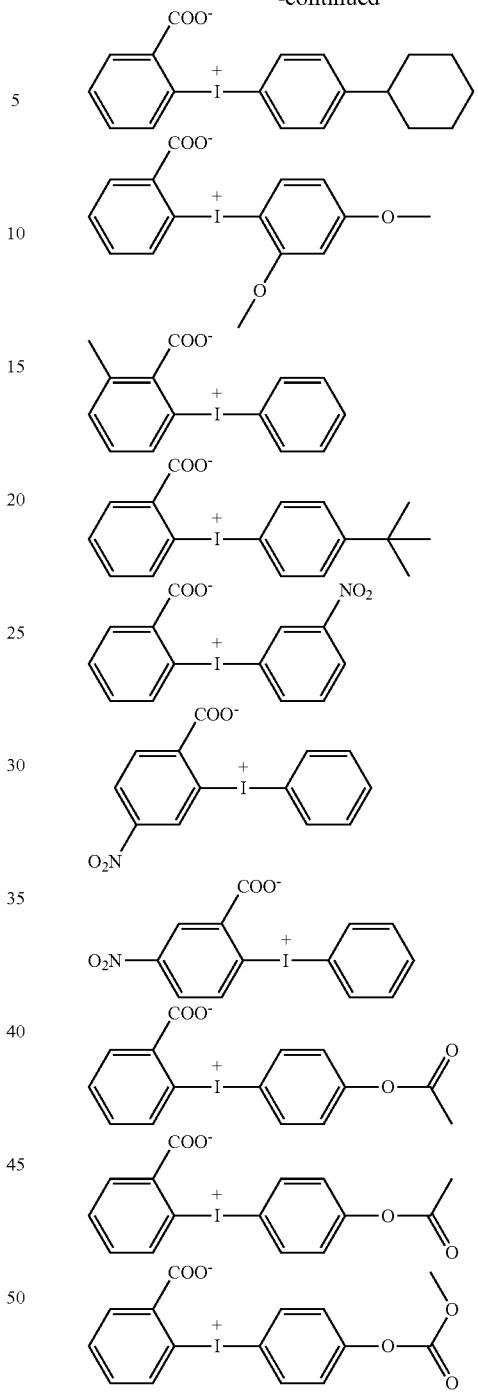

The amount of quencher is preferably 0.01 to 5% by mass, more preferably 0.01 to 4% by mass, and still more preferably 0.01 to 3% by mass, based on sum of the solid components.

The photoresist compositions of the disclosure may further contain a solvent.

The amount of the solvent is usually 90% by weight or more, preferably 92% by weight or more preferably 94% by weight or more based on total amount of the photoresist composition of the disclosure.

The amount of the solvent is usually 99.9% by weight or less and preferably 99% by weight or less based on total amount of the photoresist composition of the disclosure.

Examples of the solvent include a glycoletherester such as ethylcellosolve acetate, methylcellosolve acetate and propyleneglycolmonomethylether acetate; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The photoresist compositions of the disclosure can contain, if necessary, a small amount of various additives such as a sensitizer, a dissolution inhibitor, other polymers, a surfactant, a stabilizer and a dye as long as the effect of the disclosure is not prevented.

The photoresist compositions of the disclosure can usually be prepared by mixing, in a solvent, resin (A), resin (X) and an acid generator, and if necessary resin (Y), a quencher and/or additives at a suitable ratio for the composition, optionally followed by filtrating the mixture with a filter having 0.003 μm to 0.2 μm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the disclosure are useful for a chemically amplified photoresist composition.

A photoresist pattern can be produced using the photoresist composition of the disclosure by the following steps (1) to (5):

(1) a step of applying the photoresist composition of the disclosure on a substrate,
(2) a step of forming a composition film by drying the composition,
(3) a step of exposing the composition film to radiation,
(4) a step of baking the exposed composition film, and
(5) a step of developing the baked composition film.

The applying of the photoresist composition on a substrate is usually conducted using a conventional apparatus such as spin coater. Examples of the substrate include a silicon wafer or other inorganic material. The substrate may be coated with a reflect-preventing layer such as one containing hexamethyldisilazane.

For forming the reflect-preventing layer, such composition for organic reflect-preventing layer as available on the market can be used.

The composition film is usually formed by heating the coat layer with a heating apparatus such as hot plate or a decompressor, to thereby dry off the solvent. The heating temperature is preferably 50 to 200° C., the time of heating is preferably 10 to 180 seconds, and the operation pressure is preferably 1 to $1.0*10^5$ Pa. These conditions can be selected in view of the solvent.

The composition film obtained is exposed to radiation using an exposure system. The exposure is usually conducted through a mask having a pattern corresponding to the desired photoresist pattern.

Examples of the exposure source include a light source radiating laser light in a UV-region such as a KrF excimer laser (wavelength: 248 nm), an ArF excimer laser (wavelength: 193 nm) and a F2 laser (wavelength: 157 nm), and a light source radiating harmonic laser light in a far UV region or a vacuum UV region by wavelength conversion of laser light from a solid laser light source (such as YAG or semiconductor laser). The exposure source may be electric beam or extremely ultraviolet (EUV).

The step of baking of the exposed composition film is so called post-exposure bake, which is conducted with heating means such as hot plates. The temperature of baking of the exposed composition film is preferably 50 to 200° C., and more preferably 70 to 150° C. The deprotection reaction further proceeds by post-exposure bake.

The development of the baked composition film is usually carried out with a developer using a development apparatus. The development method includes dipping methods, paddle methods, spray methods and dynamic dispense method. The developing temperature is preferably 5 to 60° C., and the developing time is preferably 5 to 300 seconds. Photoresist patterns can be formed by development.

When a positive type photoresist pattern is prepared from the photoresist composition of the disclosure, the development can be conducted with an alkaline developer. The alkaline developer to be used may be any one of various alkaline aqueous solution used in the art. Generally, an aqueous solution of tetramethylammonium hydroxide or (2-hydroxyethyl) trimethylammonium hydroxide (commonly known as "choline") is often used. The alkaline developer may comprise a surfactant.

After development, the photoresist film having photoresist pattern is preferably washed with ultrapure water, and the remained water on the photoresist film and the substrate is preferably removed therefrom.

When a negative type photoresist pattern is prepared from the photoresist composition of the disclosure, the development can be conducted with a developer containing an organic solvent, such developer is sometimes referred to as "organic developer". Examples of an organic solvent for organic developer include ketone solvents such as 2-hexanone, 2-heptanone; glycolether ester solvents such as propyleneglycolmonomethylether acetate; ester solvents such as butyl acetate; glycolether solvents such as propyleneglycolmonomethylether; amide solvents such as N,N-dimethylacetamide; and aromatic hydrocarbon solvents such as anisole.

The content of organic solvent is preferably from 90% to 100% by weight, more preferably from 95% to 100% by weight, in an organic developer. Preferred is that the organic developer essentially consists of an organic solvent.

Among them, the organic developer is preferably a developer comprising butyl acetate and/or 2-heptanone.

The total content of butyl acetate and 2-heptanone is preferably from 50% to 100% by weight, more preferably from 90% to 100% by weight.

Preferred is that the organic developer essentially consists of butyl acetate and/or 2-heptanone.

The organic developer may comprise a surfactant or a very small amount of water.

Development with an organic developer can be stopped by replacing the developer by other solvent than it such as alcohol.

After development, the photoresist film having a photoresist pattern is preferably washed with a rinse agent. Such agent is not limited to specific one provided that it dissolve the film to be washed, example of which include a solvent containing a general organic solvent, preferably alcohol or ester solvents.

After washing, the remained rinse agent on the photoresist film and the substrate is preferably removed therefrom.

The photoresist composition of the disclosure is suitable for KrF excimer laser lithography, ArF excimer laser lithography, EB (electron beam) lithography and EUV exposure lithography, particularly for ArF excimer laser lithography. The photoresist composition is suitable for the fine processing of the semiconductor.

EXAMPLES

The photoresist composition of the disclosure will be described more specifically by Examples, which are not construed to limit the scope of the invention.

The "%" and "part(s)" used to represent the content of any component and the amount of any material used in the following examples and comparative examples are on a weight basis unless otherwise specifically noted.

The weight-average molecular weight of any material used in the following examples is a value found by gel permeation chromatography under the following conditions.

Equipment: HLC-8120GPC type, manufactured by TOSOH CORPORATION

Column: Three of TSKgel Multipore HXL-M with guard column, manufactured by TOSOH CORPORATION Solvent: tetrahydrofuran, Flow rate: 1.0 mL/min.

Detector: RI Detector

Column temperature: 40° C.

Injection volume: 100 μL

Standard reference material: standard polystyrene, manufactured by TOSOH CORPORATION.

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.). Here, the values at the peaks of spectrum are referred to as "MASS."

Example 1

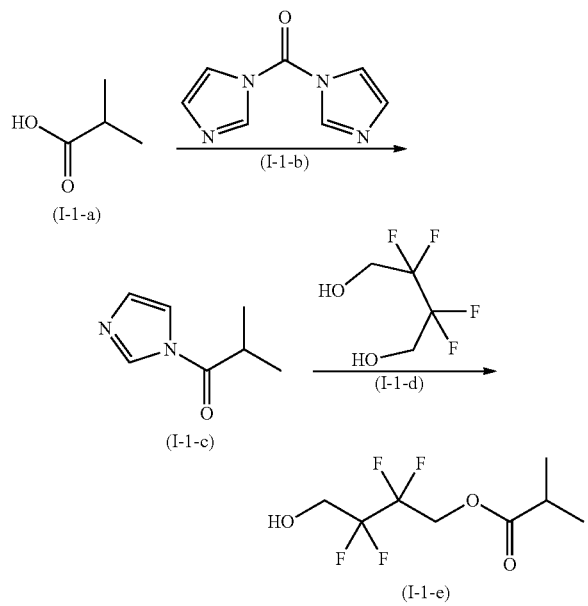

To the reactor, 6.8 parts of the compound represented by formula (I-1-a) and 50 parts of acetonitrile were added and stirred at 23° C. for 30 minutes. To the obtained mixture, 13.77 parts of the compound represented by formula (I-1-b) was added and then stirred at 70° C. for 2 hours to thereby obtain a solution which contained the compound represented by formula (I-1-c).

To the obtained solution, 25.03 parts of the compound represented by formula (I-1-d) was added and then stirred at 23° C. for 48 hours, followed by being concentrated. To the obtained concentrates, 200 parts of chloroform and 170 parts of 10% aqueous oxalic acid solution were added and then stirred at 23° C. for 30 minutes, followed by being filtrated. The organic layer was collected from the filtrated solution by separation.

To the organic layer, 100 parts of ion exchanged water was added and stirred at 23° C. for 30 minutes, followed by standing the mixture still to separate into an organic layer: These operations were conducted five times.

The washed organic layer was concentrated to obtain 12.89 parts of the compound represented by formula (I-1-e)

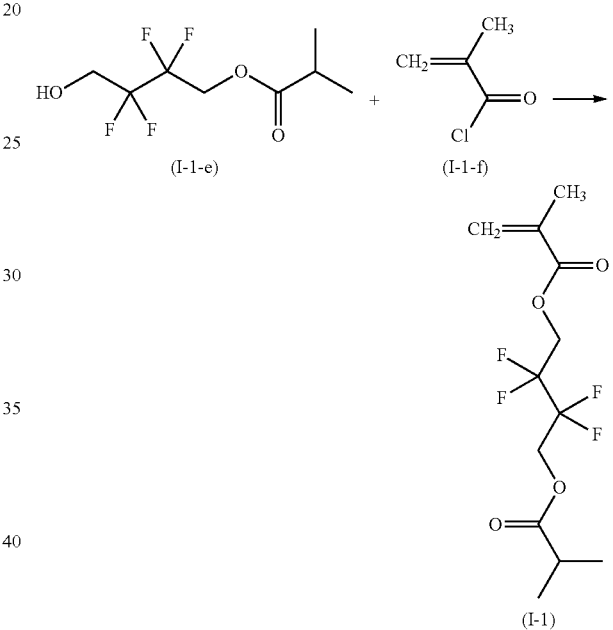

Then into a reactor, 11.61 parts of the compound represented by formula (I-1-e), 50 parts of tetrahydrofuran and 6.07 parts of trimethylamine were fed and then stirred at 23° C. for 30 minutes, followed by being cooled to 0° C.

To the obtained mixture, 5.75 parts of the compound represented by formula (I-1-f) was added over an hour and further stirred at 23° C. for an hour.

To the obtained mixture, 50 parts of ion exchanged water and 100 parts of chloroform were added and then stirred at 23° C. for 30 minutes, followed by standing the mixture still to separate into an organic layer.

To the collected organic layer, 50 parts of saturated aqueous potassium carbonate solution were added and then stirred at 23° C. for 30 minutes, followed by standing the mixture still to separate into an organic layer.

To the washed organic layer, 50 parts of ion exchanged water was added and stirred at 23° C. for 30 minutes, followed by standing the mixture still to separate into an organic layer. These operations were conducted five times.

The washed organic layer was concentrated, followed by separating the obtained concentrates using column [silica gel 60N (spherical shape, neutral), made by Kanto chemical, Co., Ltd., 100 to 210 μm, eluent: n-heptane/ethyl acetate-10/1] to obtain 11.68 parts of the compound represented by the formula (I-1).

MASS (Mass spectrography): 300.1 (molecular ion peak)

Example 2

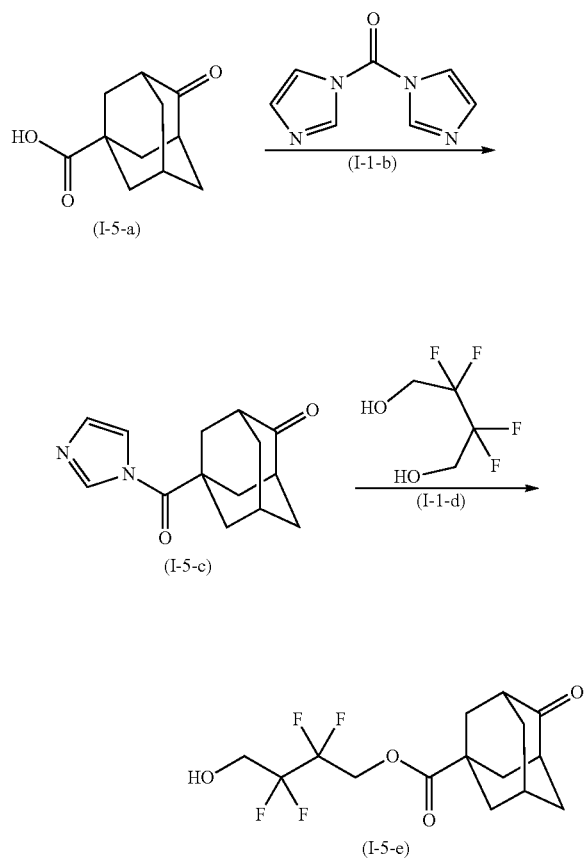

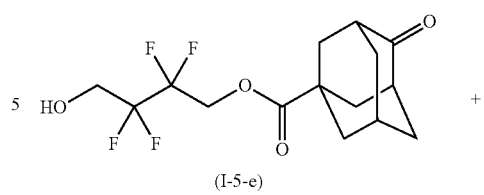

To the reactor, 15 parts of the compound represented by formula (I-5-a) and 75 parts of acetonitrile were added and stirred at 23° C. for 30 minutes. To the obtained mixture, 13.77 parts of the compound represented by formula (I-1-b) was added and then stirred at 70° C. for 2 hours to thereby obtain a solution which contained the compound represented by formula (I-5-c).

To the obtained solution, 25.03 parts of the compound represented by formula (I-1-d) was added and then stirred at 23° C. for 48 hours, followed by being concentrated. To the obtained concentrates, 170 parts of chloroform and 170 parts of 10% aqueous oxalic acid solution were added and then stirred at 23° C. for 30 minutes, followed by being filtrated. The organic layer was collected from the filtrated solution by separation.

To the organic layer, 170 parts of ion exchanged water was added and stirred at 23° C. for 30 minutes, followed by standing the mixture still to separate into an organic layer: These operations were conducted five times.

The washed organic layer was concentrated to obtain 24.74 parts of the compound represented by formula (I-5-e)

Then into a reactor, 16.92 parts of the compound represented by formula (I-5-e), 50 parts of tetrahydrofuran and 6.07 parts of trimethylamine were fed and then stirred at 23° C. for 30 minutes, followed by being cooled to 0° C.

To the obtained mixture, 5.75 parts of the compound represented by formula (I-1-f) was added over an hour and further stirred at 23° C. for an hour.

To the obtained mixture, 50 parts of ion exchanged water and 100 parts of chloroform were added and then stirred at 23° C. for 30 minutes, followed by standing the mixture still to separate into an organic layer.

To the collected organic layer, 50 parts of saturated aqueous potassium carbonate solution were added and then stirred at 23° C. for 30 minutes, followed by standing the mixture still to separate into an organic layer.

To the washed organic layer, 50 parts of ion exchanged water was added and stirred at 23° C. for 30 minutes, followed by standing the mixture still to separate into an organic layer: These operations were conducted five times.

The washed organic layer was concentrated, followed by separating the obtained concentrates using column [silica gel 60N (spherical shape, neutral), made by Kanto chemical, Co., Ltd., 100 to 210 μm, eluent: n-heptane/ethyl acetate=1/1] to obtain 12.42 parts of the compound represented by the formula (I-5).

MASS (Mass spectrography): 406.1 (molecular ion peak)

Example 3

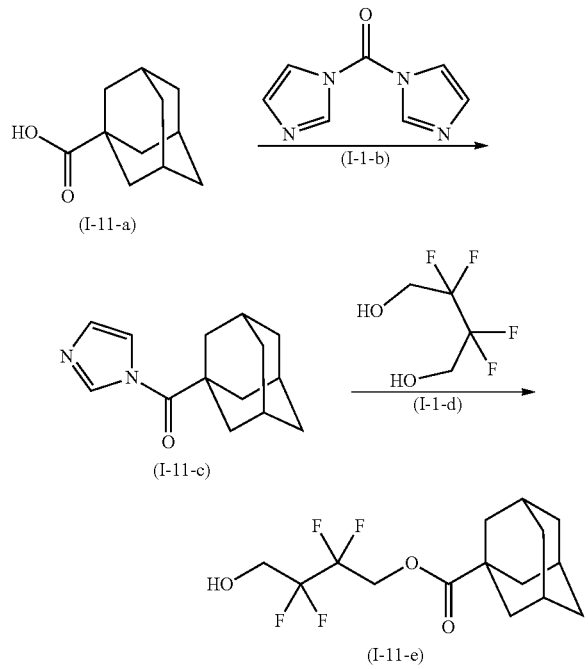

To the reactor, 13.92 parts of the compound represented by formula (I-11-a) and 75 parts of acetonitrile were added and stirred at 23° C. for 30 minutes. To the obtained mixture, 13.77 parts of the compound represented by formula (I-1-b) was added and then stirred at 70° C. for 2 hours to thereby obtain a solution which contained the compound represented by formula (I-11-c).

To the obtained solution, 25.03 parts of the compound represented by formula (I-1-d) was added and then stirred at 23° C. for 48 hours, followed by being concentrated. To the obtained concentrates, 170 parts of chloroform and 170 parts of 10% aqueous oxalic acid solution were added and then stirred at 23° C. for 30 minutes, followed by being filtrated. The organic layer was collected from the filtrated solution by separation.

To the organic layer, 170 parts of ion exchanged water was added and stirred at 23° C. for 30 minutes, followed by standing the mixture still to separate into an organic layer: These operations were conducted five times.

The washed organic layer was concentrated to obtain 20.19 parts of the compound represented by formula (I-11-e)

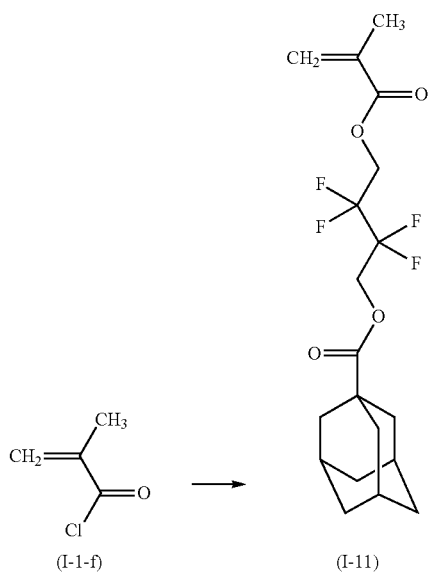

Then into a reactor, 16.22 parts of the compound represented by formula (I-11-e), 50 parts of tetrahydrofuran and 6.07 parts of trimethylamine were fed and then stirred at 23° C. for 30 minutes, followed by being cooled to 0° C.

To the obtained mixture, 5.75 parts of the compound represented by formula (1-1-f) was added over an hour and further stirred at 23° C. for an hour.

To the obtained mixture, 50 parts of ion exchanged water and 100 parts of chloroform were added and then stirred at 23° C. for 30 minutes, followed by standing the mixture still to separate into an organic layer.

To the collected organic layer, 50 parts of saturated aqueous potassium carbonate solution were added and then stirred at 23° C. for 30 minutes, followed by standing the mixture still to separate into an organic layer.

To the washed organic layer, 50 parts of ion exchanged water was added and stirred at 23° C. for 30 minutes, followed by standing the mixture still to separate into an organic layer.

The washed organic layer was concentrated, followed by separating the obtained concentrates using column [silica gel 60N (spherical shape, neutral), made by Kanto chemical, Co., Ltd., 100 to 210 μm, eluent: n-heptane/ethyl acetate=5/1] to obtain 14.28 parts of the compound represented by the formula (I-11).

MASS (Mass spectrography): 392.2 (molecular ion peak)

Synthesis Example 1

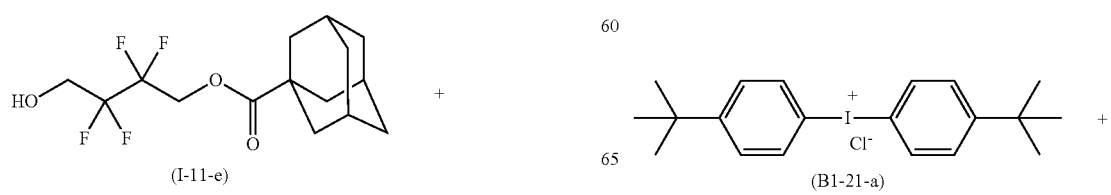

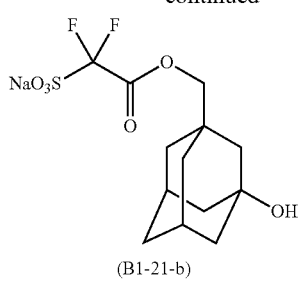

(B1-21-b)

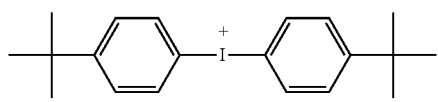

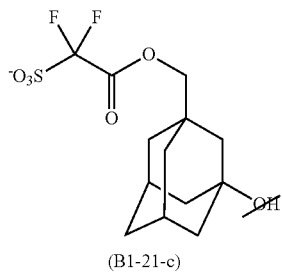

(B1-21-c)

The compound represented by the formula (B1-21-b) was produced according to a method recited in JP2008-209917A1.

Into a reactor, 30.00 parts of the compound represented by the formula (B1-21-b), 35.50 parts of a salt represented by the formula (B1-21-a), 100 parts of chloroform and 50 parts of ion-exchanged water were charged and stirred at 23° C. for about 15 hours. From the obtained solution which had two layers, a chloroform layer was collected and then 30 parts of ion-exchanged water was added thereto for washing. These steps were conducted five times. Then the organic layer was concentrated, and then, 100 parts of tert-butylmethylether was added to the obtained residues, and the obtained mixture was stirred at 23° C. for about 30 minutes. The resulting mixture was filtrated to obtain 48.57 parts of the salt represented by the formula (B1-21-c).

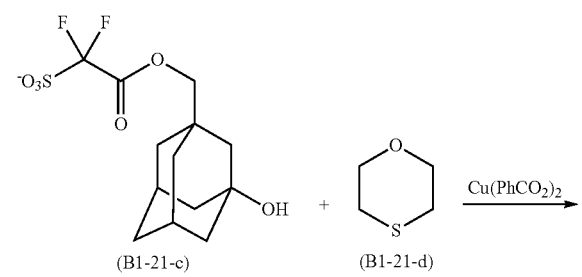

(B1-21-c)      (B1-21-d)

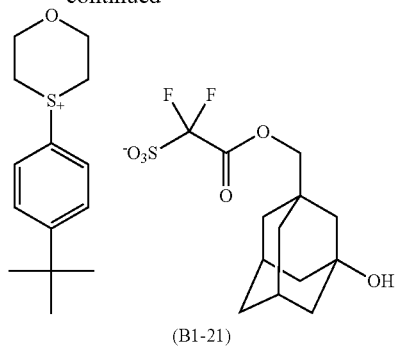

(B1-21)

Into a reactor, 20.00 parts of salt represented by the formula (B1-21-c), 2.84 parts of compound represented by the formula (B1-21-d) and 250 parts of monochlorobenzene were charged and stirred at 23° C. for 30 minutes. To the resulting mixture, 0.21 parts of copper (II) dibenzoate was added and the obtained mixture was stirred at 100° C. for 1 hour. The reaction mixture was concentrated, and then, 200 parts of chloroform and 50 parts of ion-exchanged water were added to the obtained residues and the obtained mixture was stirred at 23° C. for 30 minutes, followed by separating an organic layer. 50 parts of ion-exchanged water was added to the obtained organic layer, and the obtained mixture was stirred at 23° C. for 30 minutes, followed by separating an organic layer. The washing step with water was conducted five times. The obtained organic layer was concentrated, and then the obtained residues were dissolved in 53.51 parts of acetonitrile. Then the mixture was concentrated, and 113.05 parts of tert-butylmethylether was added thereto and the obtained mixture was stirred, followed by filtrating it to obtain 10.47 parts of the salt represented by the formula (B1-21).

MASS (ESI(+) Spectrum): M$^+$ 237.1
MASS (ESI(−) Spectrum): M$^−$ 339.1

Synthesis Example 2

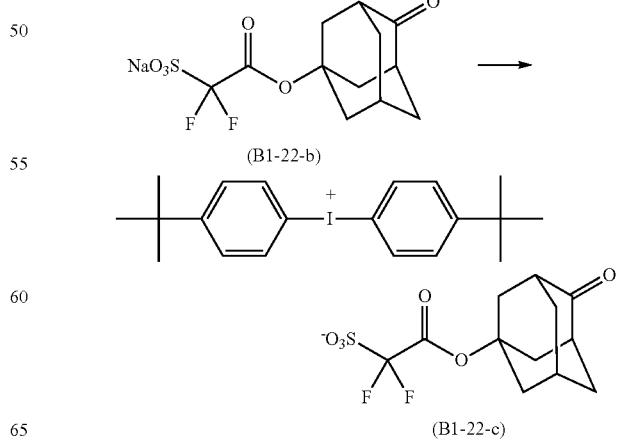

Into a reactor, 11.26 parts of the salt represented by the formula (B1-21-a), 10 parts of the compound represented by the formula (B1-22-b), 50 parts of chloroform and 25 parts of ion-exchanged water were charged and stirred at 23° C. for about 15 hours. From the obtained solution which had two layers, a chloroform layer was collected and then 15 parts of ion-exchanged water were added thereto for washing. These steps were conducted five times. Then the organic layer was concentrated, and then 50 parts of tert-butylmethylether was added to the obtained residues, and the obtained mixture was stirred at 23° C. for about 30 minutes. The resulting mixture was filtrated to obtain 11.75 parts of the salt represented by the formula (B1-22-c).

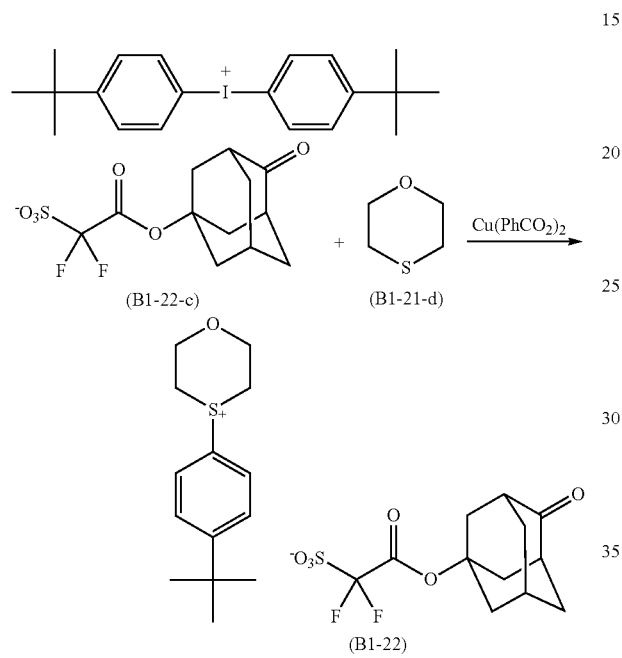

Into a reactor, 11.71 parts of a salt represented by the formula (B1-22-c), 1.70 parts of a compound represented by the formula (B1-21-d) and 46.84 parts of monochlorobenzene were charged and stirred at 23° C. for 30 minutes. To the resulting mixture, 0.12 parts of copper (II) dibenzoate was added and the obtained mixture was stirred at 100° C. for 30 minutes. The reaction mixture was concentrated, and then 50 parts of chloroform and 12.50 parts of ion-exchanged water were added to the obtained residues, and the obtained mixture was stirred at 23° C. for 30 minutes, followed by separating an organic layer. 12.50 parts of ion-exchanged water was added to the obtained organic layer and the obtained mixture was stirred at 23° C. for 30 minutes, followed by separating an organic layer to wash with water. The washing step with water was conducted eight times. Then the obtained organic layer was concentrated, and 50 parts of tert-butylmethylether were added thereto and the obtained mixture was stirred, followed by being filtrated it to obtain 6.84 parts of the salt represented by the formula (B1-22).

MASS (ESI(+) Spectrum): M⁺ 237.1

MASS (ESI(−) Spectrum): M⁻ 323.0

Synthesis of Resin

The compounds used in the syntheses of the resin are as follow.

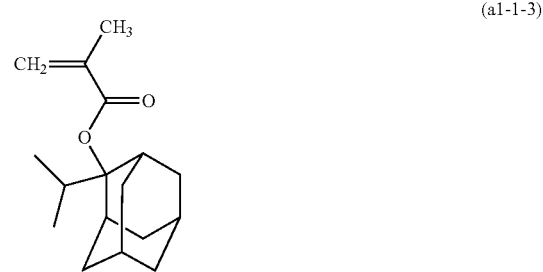

(a1-1-3)

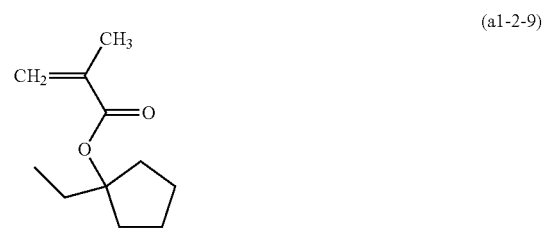

(a1-2-9)

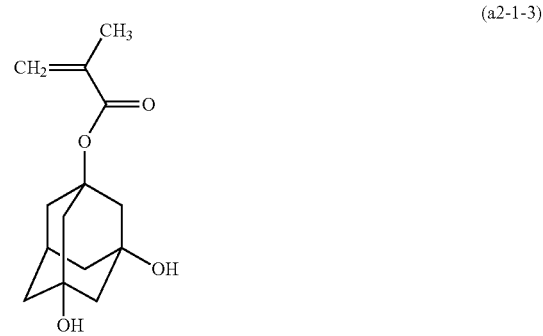

(a2-1-3)

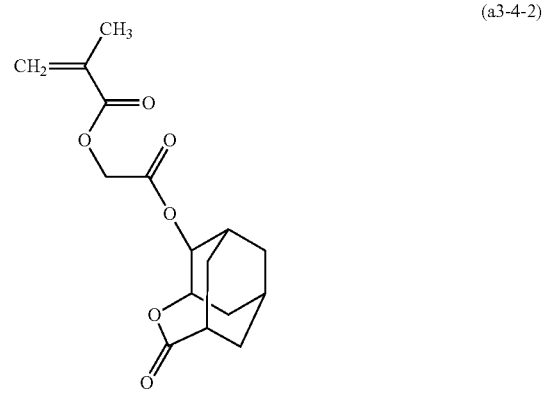

(a3-4-2)

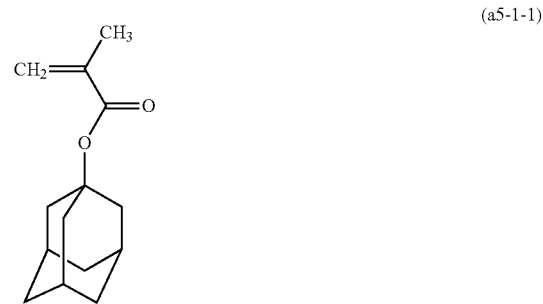

(a5-1-1)

(I-1)

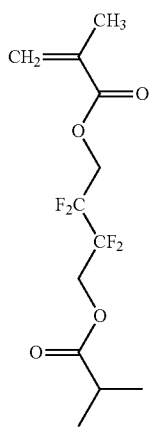

(I-5)

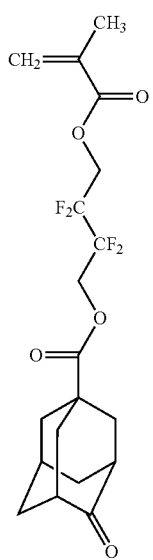

(I-11)

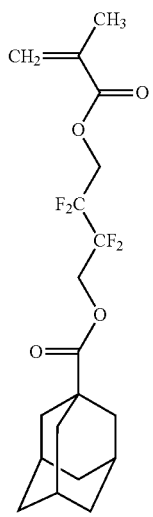

(IX-1)

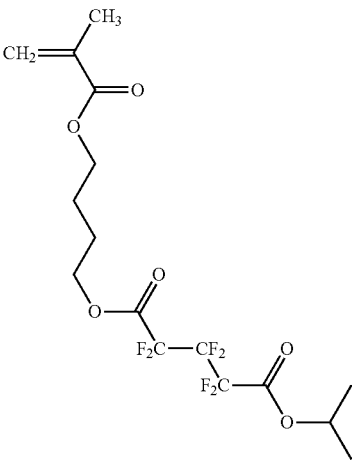

Hereinafter, these compounds are referred to as "monomer (X)" where "(X)" is the symbol of the formula representing the structure of each compound.

Synthesis Example 3

Monomer (a1-1-3), monomer (a1-2-9), monomer (a2-1-3) and monomer (a3-4-2) were mixed together with a mole ratio of monomer (a1-1-3), monomer (a1-2-9), monomer (a2-1-3) and monomer (a3-4-2)=45:14:2.5:38.5, and propylene glycol monomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1% by mole and 3% by mole respectively with respect to the total amount of monomers, and the resultant mixture was heated at 73° C. for about 5 hours. Then, the obtained reaction mixture was poured into a large amount of a mixture of methanol and water to precipitate a resin. The obtained resin was filtrated. The obtained resin was dissolved in propyleneglycolmonomethylether acetate, and the obtained solution was poured into a large amount of a mixture of methanol and ion-exchanged water (methanol/ion-exchanged water=4/1), followed by being filtrated to obtain the copolymer: This reprecipitation step was conducted twice. A resin having a weight average molecular weight of about 7600 in 68% yield was obtained. This resin, which had the structural units of the following formulae, was referred to as Resin A1.

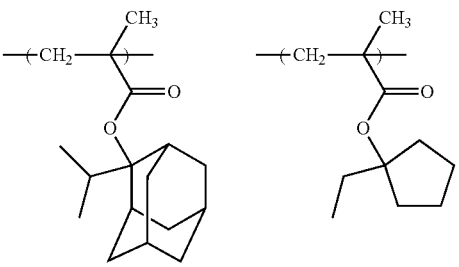

-continued

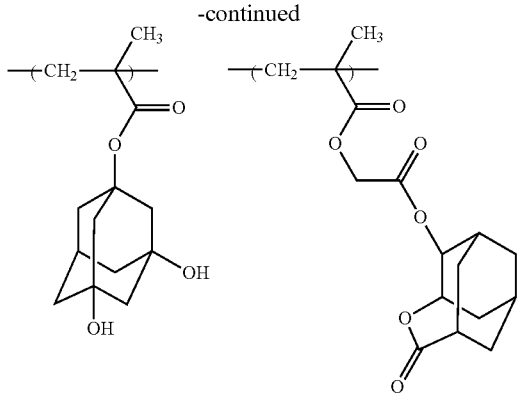

Example 4

Monomer (I-1) was dissolved in propyleneglycolmonomethylether acetate in the amount equal to 1.5 times by mass of the total amount of the monomer to obtain a solution. Azobisisobutyronitrile and azobis(2,4-dimethylvaleronitrile) were added as initiators to the solution in the amounts of 0.7% by mole and 2.1% by mole respectively with respect to the total amount of the monomer, and the resultant mixture was heated at 75° C. for about 5 hours. Then, the obtained reaction mixture was poured into a large amount of a mixture of methanol and water to precipitate a resin. The obtained resin was filtrated. The obtained resin was dissolved in propyleneglycolmonomethylether acetate, and the obtained solution was poured into a large amount of a mixture of methanol and ion-exchanged water (methanol/ion-exchanged water=4/1), followed by being filtrated to collect the resin: This reprecipitation step was conducted twice.

The resin, which was a copolymer obtained in 71% yield, had a weight average molecular weight of about 17000 and the structural unit of the following formula. The resin was referred to as Resin X1.

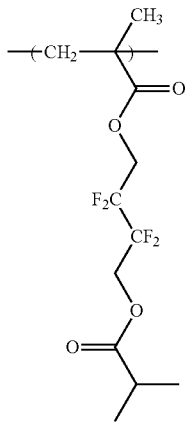

Example 5

Monomer (I-1) and monomer (a5-1-1) were mixed together with a mole ratio of monomer (I-1) and monomer (a5-1-1)=75:25, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated at 75° C. for about 5 hours. Then, the obtained reaction mixture was poured into a large amount of a mixture of methanol and ion-exchanged water (methanol/ion-exchanged water=4/1), followed by being filtrated to obtain a copolymer having a weight average molecular weight of about 15000 in 82% yield. This copolymer, which had the structural units of the following formulae, was referred to as Resin X2.

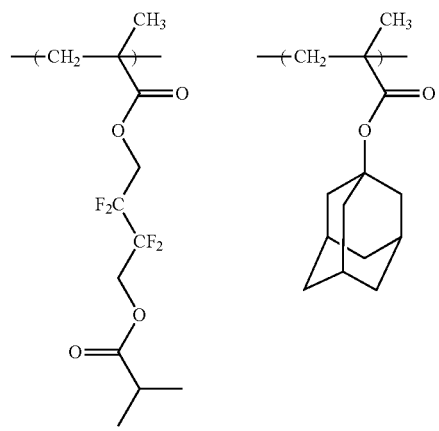

Example 6

Monomer (1-5) and monomer (a5-1-1) were mixed together with a mole ratio of monomer (1-5) and monomer (a5-1-1)=50:50, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1% by mole and 3% by mole respectively with respect to the total amount of monomers, and the resultant mixture was heated at 75° C. for about 5 hours. Then, the obtained reaction mixture was poured into a large amount of a mixture of methanol and ion-exchanged water (methanol/ion-exchanged water=4/1), followed by being filtrated to obtain a resin having a weight average molecular weight of about 8800 in 76% yield. This resin had the structural units of the following formulae, which was referred to as Resin X3.

147

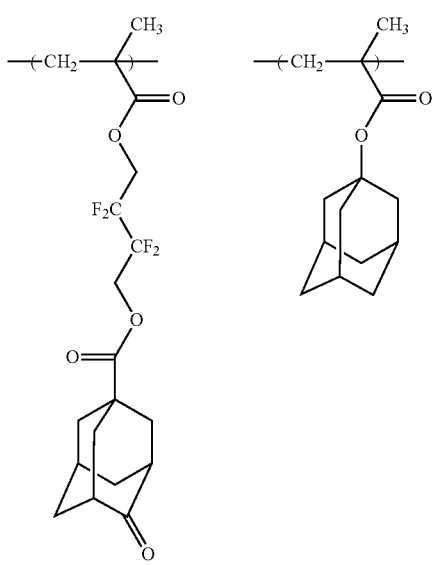

Example 7

Monomer (I-11) was dissolved in propyleneglycolmonomethylether acetate in the amount equal to 1.5 times by mass of the total amount of the monomer to obtain a solution. Azobisisobutyronitrile and azobis(2,4-dimethylvaleronitrile) were added as initiators to the solution in the amounts of 1% by mole and 3% by mole respectively with respect to the total amount of the monomer, and the resultant mixture was heated at 75° C. for about 5 hours. Then, the obtained reaction mixture was poured into a large amount of a mixture of methanol and water to precipitate a resin. The obtained resin was filtrated. The obtained resin was dissolved in propyleneglycolmonomethylether acetate, and the obtained solution was poured into a large amount of a mixture of methanol and ion-exchanged water (methanol/ion-exchanged water=4/1), followed by being filtrated to collect the resin: This reprecipitation step was conducted twice.

The resin, which was obtained in 70% yield, had a weight average molecular weight of about 7900 and the structural unit of the following formula. The resin was referred to as Resin X4.

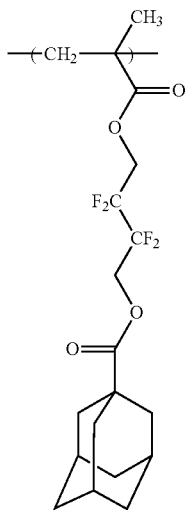

148

Example 8

Monomer (I-11) and monomer (a5-1-1) were mixed together with a mole ratio of monomer (I-11) and monomer (a5-1-1)=50:50, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1% by mole and 3% by mole respectively with respect to the total amount of monomers, and the resultant mixture was heated at 75° C. for about 5 hours. Then, the obtained reaction mixture was poured into a large amount of a mixture of methanol and ion-exchanged water (methanol/ion-exchanged water=4/1), followed by being filtrated to obtain a resin having a weight average molecular weight of about 8900 in 79% yield. This resin had the structural units of the following formulae, which was referred to as Resin X5.

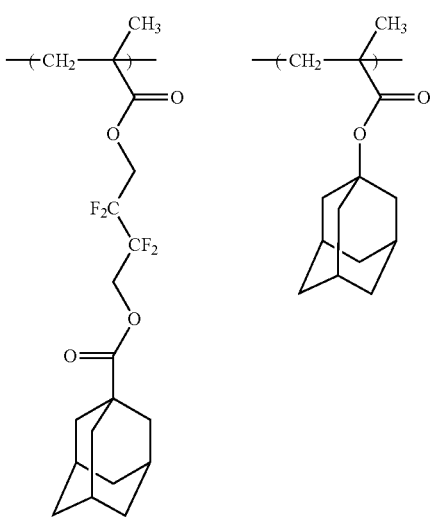

Synthesis Example 4

Monomer (IX-1) was dissolved in propyleneglycolmonomethylether acetate in the amount equal to 1.5 times by mass of the total amount of the monomer to obtain a solution. Azobisisobutyronitrile and azobis(2,4-dimethylvaleronitrile) were added as initiators to the solution in the amounts of 0.7% by mole and 2.1% by mole respectively with respect to the total amount of the monomer, and the resultant mixture was heated at 75° C. for about 5 hours. Then, the obtained reaction mixture was poured into a large amount of a mixture of methanol and water to precipitate a resin. The obtained resin was filtrated. The resin, which was obtained in 80% yield, had a weight average molecular weight of about 15000 and the structural unit of the following formula. The resin was referred to as Resin Xx1.

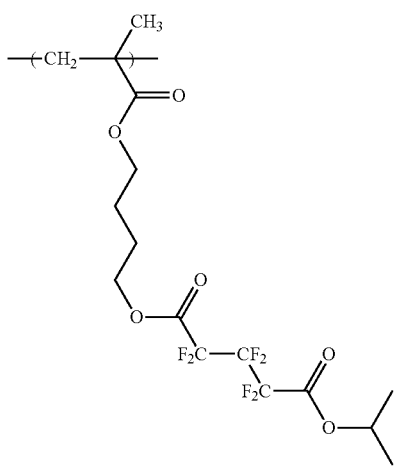

<Preparation of Photoresist Composition>

The following components shown in Table 1 were mixed and dissolved, further, filtrated through a fluorine resin filter having pore diameter of 0.2 μm, to prepare photoresist compositions.

TABLE 1

| No. | Resin (Kind/Parts) | Acid generator (Kind/Parts) | Quencher (Kind/Parts) | PB/PEB |
|---|---|---|---|---|
| Composition 1 | X1/0.4 A1/10 | B1-21/0.9 B1-22/0.4 | D1/0.28 | 90° C./85° C. |
| Composition 2 | X2/0.4 A1/10 | B1-21/0.9 B1-22/0.4 | D1/0.28 | 90° C./85° C. |
| Composition 3 | X3/0.4 A1/10 | B1-21/0.9 B1-22/0.4 | D1/0.28 | 90° C./85° C. |
| Composition 4 | X4/0.4 A1/10 | B1-21/0.9 B1-22/0.4 | D1/0.28 | 90° C./85° C. |
| Composition 5 | X5/0.4 A1/10 | B1-21/0.9 B1-22/0.4 | D1/0.28 | 90° C./85° C. |
| Comparative Composition 1 | Xx1/0.4 A1/10 | B1-21/0.9 B1-22/0.4 | D1/0.28 | 90° C./85° C. |

The symbols shown in Table 1 represent the following components.

<Resin>

A1: Resin A1, X1: Resin X1, X2: Resin X2, X3: Resin X3
X4: Resin X4, X5: Resin X5, Xx1: Resin Xx1

<Acid Generator>

B1-21: Salt represented by formula (B1-21)

B1-22: Salt represented by formula (B1-22)

<Quencher>

D1: Compound represented by formula D1, a product of Tokyo Chemical Industry Co., LTD

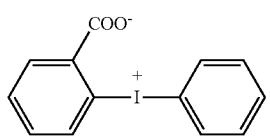

D1

<Solvent>

| Mixture of the following solvents | |
|---|---|
| Propyleneglycolmonomethylether acetate | 265 parts |
| Propyleneglycolmonomethyl ether | 20 parts |
| 2-Heptanone | 20 parts |
| γ-butyrolactone | 3.5 parts |

The following evaluations were conducted after storing the prepared photoresist compositions at 30° C. for 3 weeks.

(Production of Negative Type Photoresist Patterns)

Silicon wafer (12 inches) was coated with "ARC-29", which is an organic anti-reflective coating composition available from Nissan Chemical Industries, Ltd., and then baked at 205° C. for 60 seconds, to form a 78 nm-thick organic anti-reflective coating. One of the photoresist compositions prepared as above was spin-coated over the anti-reflective coating so that the thickness of the resulting film became 100 nm after drying.

The silicon wafer thus coated with the photoresist composition was prebaked on a direct hotplate at a temperature shown in the column "PB" in Table 1 for 60 seconds to form a composition film.

Using an ArF excimer stepper for immersion exposure ("XT: 1900Gi" manufactured by ASML, NA=1.35, Annular $\sigma_{out}$=0.85, $\sigma_{in}$=0.65, XY-pol. illumination) and a mask for preparing trench pattern (pitch: 120 nm, trench width: 40 nm), the wafer having the composition film was subjected to the exposure with the exposure quantity being varied stepwise. Ultrapure water was used for immersion solvent.

After the exposure, the wafer was subjected to post-exposure baking on a hotplate at a temperature shown in the column "PEB" in Table 1 for 60 seconds and then to conduct development in the manner of dynamic dispense method for 20 seconds at 23° C. with butyl acetate, product of Tokyo Chemical Industry, Co., Ltd to thereby obtain a negative type photoresist pattern.

(Line Edge Roughness (LER) Evaluation)

The trench patterns were produced in the above-mentioned manner except that the exposure quantity was set at an effective sensibility.

In this evaluation, the effective sensibility (ES) means the exposure quantity such that the trench patterns with the line width 40 nm were formed.

The wall surface of each obtained pattern was checked using a scanning electron microscope.

The "o" was given when the pattern has a roughness width of 3 nm or less.

The "x" was given when the pattern has a roughness width of more than 3 nm.

Table 2 illustrates the results thereof. The figures in parentheses represent roughness width (nm).

TABLE 2

| Ex. No. | Composition | LER (nm) |
|---|---|---|
| Ex. 9 | Comp. 1 | o (2.78) |
| Ex. 10 | Comp. 2 | o (2.82) |
| Ex. 11 | Comp. 3 | o (2.88) |
| Ex. 12 | Comp. 4 | o (2.69) |
| Ex. 13 | Comp. 5 | o (2.71) |
| Comparative Ex. 1 | Comparative Comp. 1 | x (3.16) |

The compound of the disclosure can provide a photoresist composition capable of forming a photoresist pattern which shows decreased line edge roughness. The photoresist composition is useful for fine processing of semiconductors.

What is claimed is:

1. A photoresist composition which comprises
a resin which comprises a structural unit derived from a compound represented by formula (I):

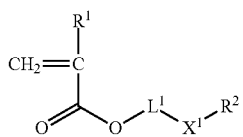

wherein $R^1$ represents a hydrogen atom, a halogen atom or a C1-C6 alkyl group where a hydrogen atom can be replaced by a halogen atom, $L^1$ represents a group represented by —$CH_2$—$(CF_2)_n$—$CH_2$— where "n" represents an integer of 1 to 6, $X^1$ represents *—CO—O—, *—O—CO—, *—O—CO—O— or *—O— where * represents a binding site to $L^1$, and $R^2$ represents a C1-C18 aliphatic hydrocarbon group in which a methylene group can be replaced by an oxygen atom, a carbonyl group or a sulfonyl group and in which a hydrogen atom can be replaced by a hydroxy group, or in which two hydrogen atoms can be each replaced by an oxygen atom forming one ketal structure together with a C1-C8 alkanediyl group bonded to the oxygen atom and a hydrogen atom in said ketal structure can be replaced by a fluorine atom, a resin which has an acid-labile group, and an acid generator.

2. A process for producing a photoresist pattern comprising the following steps (1) to (5):
    (1) a step of applying the photoresist composition according to claim 1 on a substrate,
    (2) a step of forming a composition film by drying the composition,
    (3) a step of exposing the composition film to radiation,
    (4) a step of baking the exposed composition film, and
    (5) a step of developing the baked composition film.

* * * * *